US011154300B2

(12) United States Patent
Nalagatla et al.

(10) Patent No.: US 11,154,300 B2
(45) Date of Patent: Oct. 26, 2021

(54) SURGICAL INSTRUMENT COMPRISING SEPARATE TISSUE SECURING AND TISSUE CUTTING SYSTEMS

(71) Applicant: Ethicon Endo-Surgery, LLC, Guaynabo, PR (US)

(72) Inventors: Anil K. Nalagatla, Mason, OH (US); Sudhir B. Patel, Mason, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 591 days.

(21) Appl. No.: 14/813,259

(22) Filed: Jul. 30, 2015

(65) Prior Publication Data

US 2017/0027572 A1 Feb. 2, 2017

(51) Int. Cl.
| | |
|---|---|
| *A61B 17/068* | (2006.01) |
| *A61B 17/10* | (2006.01) |
| *A61B 17/115* | (2006.01) |
| *A61B 17/072* | (2006.01) |
| *A61B 17/00* | (2006.01) |
| *A61B 17/29* | (2006.01) |
| *A61B 90/00* | (2016.01) |

(52) U.S. Cl.
CPC .......... *A61B 17/105* (2013.01); *A61B 17/068* (2013.01); *A61B 17/072* (2013.01); *A61B 17/1155* (2013.01); *A61B 2017/00017* (2013.01); *A61B 2017/00115* (2013.01); *A61B 2017/00367* (2013.01); *A61B 2017/00398* (2013.01); *A61B 2017/00407* (2013.01); *A61B 2017/07285* (2013.01); *A61B 2017/2922* (2013.01); *A61B 2017/2923* (2013.01); *A61B 2090/034* (2016.02); *A61B 2090/0811* (2016.02)

(58) Field of Classification Search
USPC ...................................................... 227/177.1
See application file for complete search history.

(56) References Cited

U.S. PATENT DOCUMENTS

| | | |
|---|---|---|
| 4,415,112 A | 11/1983 | Green |
| 4,527,724 A | 7/1985 | Chow et al. |
| 4,589,582 A | 5/1986 | Bilotti |
| 4,605,001 A | 8/1986 | Rothfuss et al. |
| 4,617,928 A | 10/1986 | Alfranca |
| 4,930,674 A | 6/1990 | Barak |
| 5,137,198 A | 8/1992 | Nobis et al. |
| 5,330,486 A | 7/1994 | Wilk |
| 5,392,979 A | 2/1995 | Green et al. |
| 5,395,033 A | 3/1995 | Byrne et al. |

(Continued)

FOREIGN PATENT DOCUMENTS

| | | |
|---|---|---|
| EP | 0795298 B1 | 6/2000 |
| JP | 2005080702 A | 3/2005 |

(Continued)

*Primary Examiner* — Anna K Kinsaul
*Assistant Examiner* — Chinyere J Rushing-Tucker

(57) ABSTRACT

A surgical instrument is disclosed which comprises a staple firing system and a tissue cutting system. In various instances, the instrument is configured to prevent the tissue cutting system from being operated before the staple firing system has been fully actuated. In certain instances, the instrument is configured to prevent the tissue cutting system from being operated before the staple firing system has been actuated to sufficiently deform the staples.

21 Claims, 64 Drawing Sheets

(56) References Cited

U.S. PATENT DOCUMENTS

| | | |
|---|---|---|
| 5,397,324 A | 3/1995 | Carroll et al. |
| 5,403,312 A | 4/1995 | Yates et al. |
| 5,405,073 A | 4/1995 | Porter |
| 5,464,144 A | 11/1995 | Guy et al. |
| 5,485,947 A | 1/1996 | Olson et al. |
| 5,605,272 A | 2/1997 | Witt et al. |
| 5,697,543 A | 12/1997 | Burdorff |
| 6,003,517 A | 12/1999 | Sheffield et al. |
| 6,099,537 A | 8/2000 | Sugai et al. |
| 6,179,195 B1 | 1/2001 | Adams et al. |
| 6,520,971 B1 | 2/2003 | Perry et al. |
| 6,805,273 B2 | 10/2004 | Bilotti et al. |
| 7,000,818 B2 | 2/2006 | Shelton, IV et al. |
| 7,237,708 B1 | 7/2007 | Guy et al. |
| 7,422,139 B2 | 9/2008 | Shelton, IV et al. |
| 7,464,847 B2 | 12/2008 | Viola et al. |
| 7,464,849 B2 | 12/2008 | Shelton, IV et al. |
| 7,490,749 B2 | 2/2009 | Schall et al. |
| 7,547,312 B2 | 6/2009 | Bauman et al. |
| 7,588,177 B2 | 9/2009 | Racenet |
| 7,658,311 B2 | 2/2010 | Boudreaux |
| 7,670,334 B2 | 3/2010 | Hueil et al. |
| 7,731,073 B2 | 6/2010 | Wixey et al. |
| 7,753,245 B2 | 7/2010 | Boudreaux et al. |
| 7,819,299 B2 | 10/2010 | Shelton, IV et al. |
| 7,845,537 B2 | 12/2010 | Shelton, IV et al. |
| 7,954,684 B2 | 6/2011 | Boudreaux |
| 7,980,443 B2 | 7/2011 | Scheib et al. |
| 8,109,426 B2 | 2/2012 | Milliman et al. |
| 8,136,712 B2 | 3/2012 | Zingman |
| 8,186,555 B2 | 5/2012 | Shelton, IV et al. |
| 8,210,411 B2 | 7/2012 | Yates et al. |
| 8,220,688 B2 | 7/2012 | Laurent et al. |
| 8,276,801 B2 | 10/2012 | Zemlok et al. |
| 8,308,040 B2 | 11/2012 | Huang et al. |
| 8,353,436 B2 | 1/2013 | Kasvikis |
| 8,393,514 B2 | 3/2013 | Shelton, IV et al. |
| 8,397,971 B2 | 3/2013 | Yates et al. |
| 8,540,131 B2 | 9/2013 | Swayze |
| 8,561,870 B2 | 10/2013 | Baxter, III et al. |
| 8,608,045 B2 | 12/2013 | Smith et al. |
| 8,733,611 B2 | 5/2014 | Milliman |
| 8,733,613 B2 | 5/2014 | Huitema et al. |
| 8,945,163 B2 | 2/2015 | Voegele et al. |
| 8,955,732 B2 | 2/2015 | Zemlok et al. |
| 9,044,227 B2 | 6/2015 | Shelton, IV et al. |
| 9,055,941 B2 | 6/2015 | Schmid et al. |
| 9,072,535 B2 | 7/2015 | Shelton, IV et al. |
| 9,101,358 B2 | 8/2015 | Kerr et al. |
| 9,168,042 B2 | 10/2015 | Milliman |
| 9,186,141 B2 | 11/2015 | Williams |
| 9,204,880 B2 | 12/2015 | Baxter, III et al. |
| 9,226,751 B2 | 1/2016 | Shelton, IV et al. |
| 9,301,763 B2 | 4/2016 | Qiao et al. |
| 9,307,989 B2 | 4/2016 | Shelton, IV et al. |
| 9,345,481 B2 | 5/2016 | Hall et al. |
| 9,386,985 B2 | 7/2016 | Koch, Jr. et al. |
| 9,408,606 B2 | 8/2016 | Shelton, IV |
| 9,517,063 B2 | 12/2016 | Swayze et al. |
| 9,549,735 B2 | 1/2017 | Shelton, IV et al. |
| 9,572,574 B2 | 2/2017 | Shelton, IV et al. |
| 9,572,577 B2 | 2/2017 | Lloyd et al. |
| 9,592,053 B2 | 3/2017 | Shelton, IV et al. |
| 9,629,814 B2 | 4/2017 | Widenhouse et al. |
| 9,662,116 B2 | 5/2017 | Smith et al. |
| 9,757,124 B2 | 9/2017 | Schellin et al. |
| 9,814,462 B2 | 11/2017 | Woodard, Jr. et al. |
| 9,839,422 B2 | 12/2017 | Schellin et al. |
| 9,844,368 B2 | 12/2017 | Boudreaux et al. |
| 9,861,367 B2 | 1/2018 | Williams |
| 9,888,919 B2 | 2/2018 | Leimbach et al. |
| 9,924,941 B2 | 3/2018 | Burbank |
| 9,962,160 B2 | 5/2018 | Petty et al. |
| 10,194,992 B2 | 2/2019 | Robinson |
| 10,265,070 B2 | 4/2019 | Chen et al. |
| 10,456,140 B2 | 10/2019 | Shelton, IV et al. |
| 2005/0145671 A1 | 7/2005 | Viola |
| 2005/0246881 A1 | 11/2005 | Kelly et al. |
| 2006/0201989 A1 | 9/2006 | Ojeda |
| 2007/0175955 A1 | 8/2007 | Shelton et al. |
| 2007/0208359 A1 | 9/2007 | Hoffman |
| 2008/0008425 A1* | 1/2008 | Anderson ............ G02B 6/3825 385/59 |
| 2009/0090763 A1* | 4/2009 | Zemlok ............ A61B 17/07207 227/175.2 |
| 2009/0302092 A1* | 12/2009 | Kasvikis ............ A61B 17/072 227/180.1 |
| 2009/0302093 A1* | 12/2009 | Kasvikis ............ A61B 17/072 227/180.1 |
| 2010/0069942 A1 | 3/2010 | Shelton, IV |
| 2010/0213240 A1* | 8/2010 | Kostrzewski ........ A61B 17/072 227/180.1 |
| 2011/0036891 A1 | 2/2011 | Zemlok et al. |
| 2011/0068147 A1* | 3/2011 | Racenet ............ A61B 17/072 227/180.1 |
| 2012/0080501 A1* | 4/2012 | Morgan ............ A61B 90/92 227/180.1 |
| 2012/0168485 A1* | 7/2012 | Marczyk ............ A61B 17/072 227/176.1 |
| 2014/0012289 A1 | 1/2014 | Snow et al. |
| 2014/0224857 A1 | 8/2014 | Schmid |
| 2014/0263552 A1 | 9/2014 | Hall et al. |
| 2015/0136833 A1* | 5/2015 | Shelton, IV ..... A61B 17/07292 227/177.1 |
| 2015/0351769 A1 | 12/2015 | Lee et al. |
| 2017/0027571 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0348003 A1 | 12/2017 | Chen et al. |

FOREIGN PATENT DOCUMENTS

| | | |
|---|---|---|
| JP | 2013541982 A | 11/2013 |
| RU | 2242183 C2 | 12/2004 |

* cited by examiner

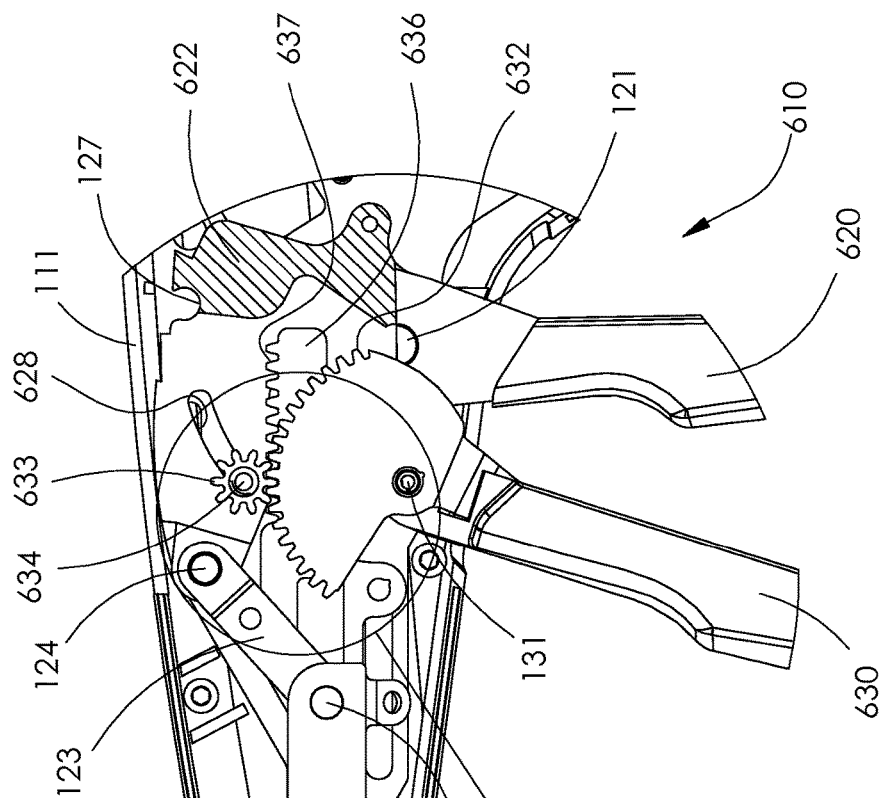
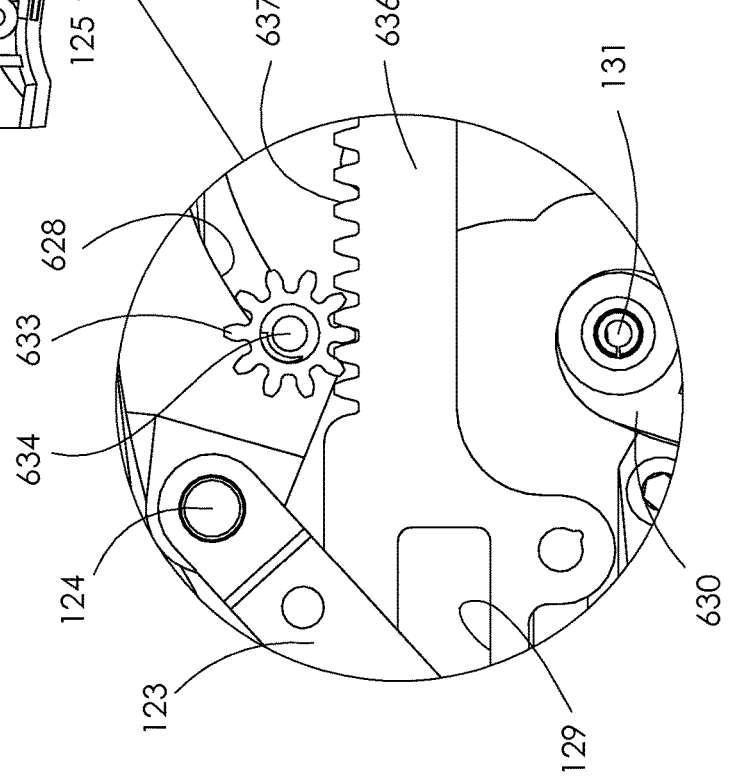
FIG. 23
FIG. 23A

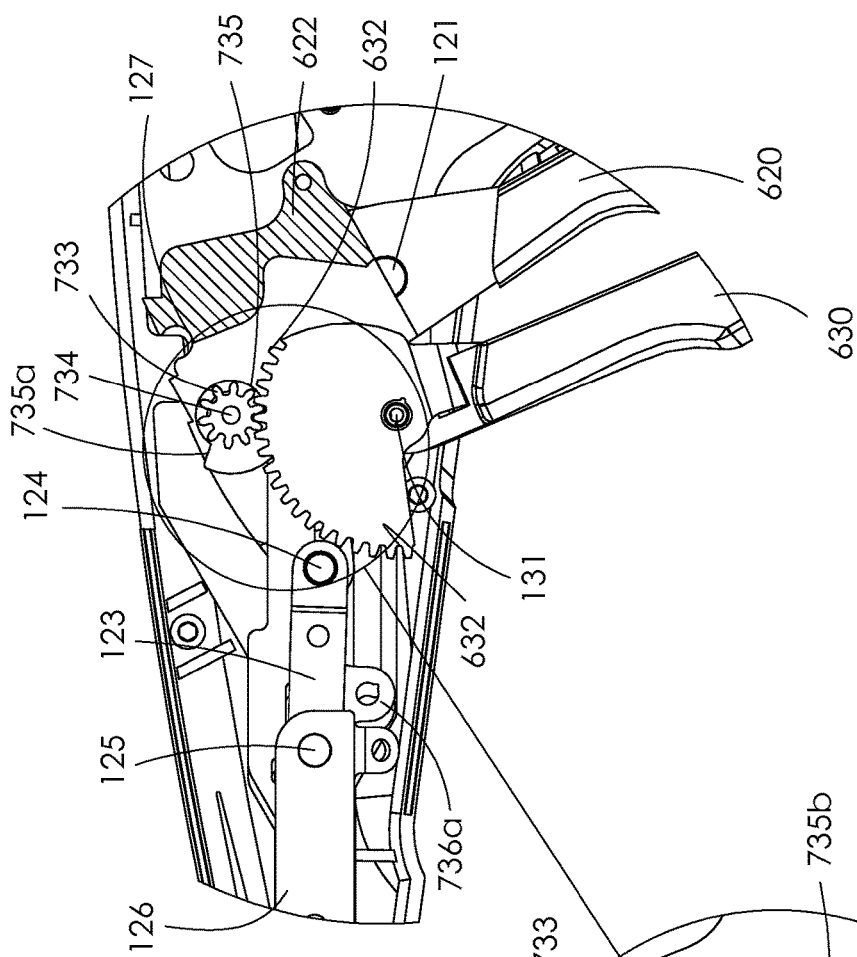
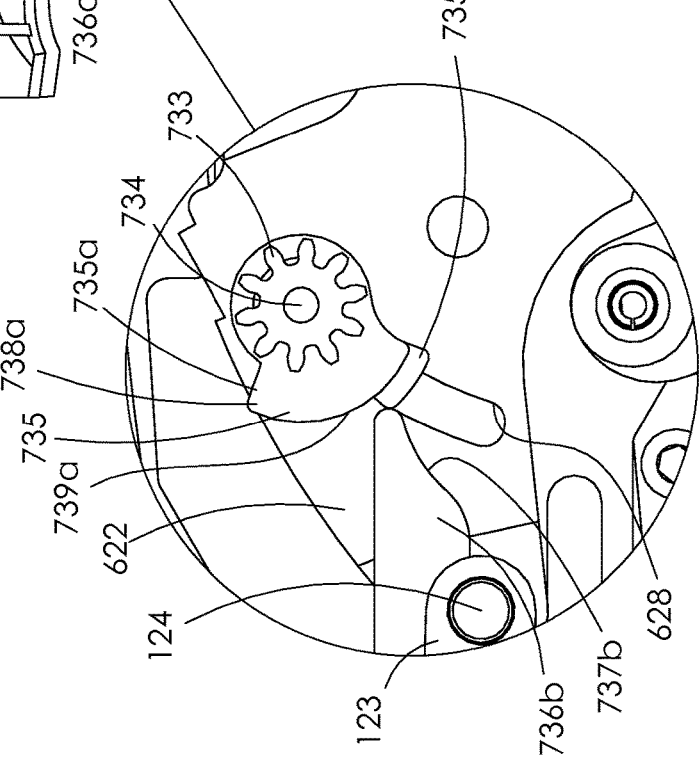
FIG. 33
FIG. 33A

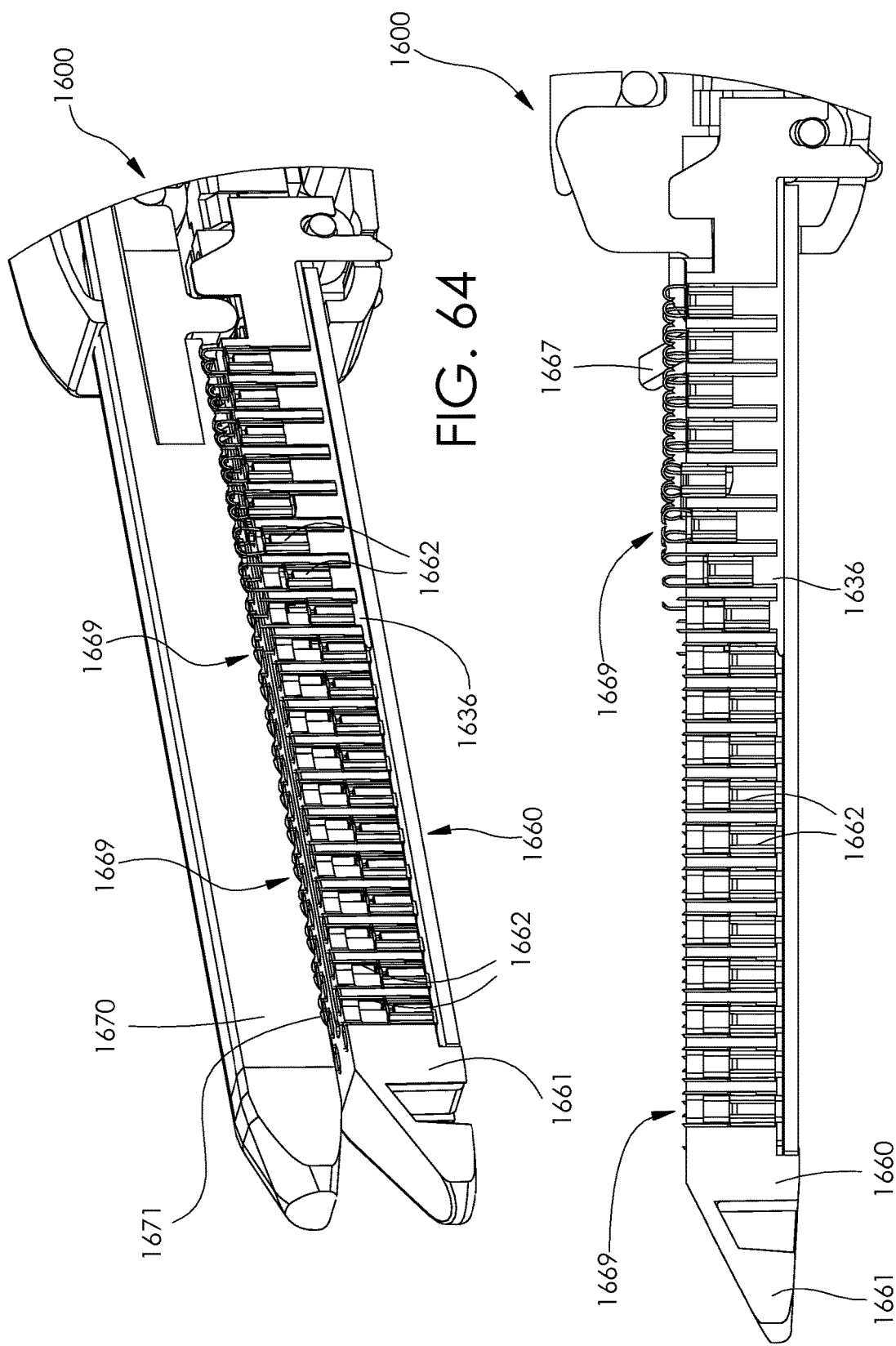

SURGICAL INSTRUMENT COMPRISING SEPARATE TISSUE SECURING AND TISSUE CUTTING SYSTEMS

BACKGROUND

The present invention relates to surgical instruments and, in various embodiments, to surgical stapling and cutting instruments and staple cartridges for use therewith.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein, together with advantages thereof, may be understood in accordance with the following description taken in conjunction with the accompanying drawings as follows:

FIG. 23 is a partial cross-sectional view of the surgical stapling instrument of FIG. 22 illustrated in an unclamped, unfired configuration;

FIG. 23A is a detail view of a transmission of the surgical stapling instrument of FIG. 22;

FIG. 33 is a partial cross-sectional view of the surgical stapling instrument of FIG. 29 illustrated in a clamped configuration in which tissue is being transected by the surgical instrument;

FIG. 33A is a detail view of the transmission of the surgical stapling instrument of FIG. 29 illustrated in a configuration which corresponds to the clamped, fired configuration depicted in FIG. 33;

FIG. 64 is a partial cross-sectional perspective view of a surgical stapling instrument in accordance with at least one embodiment illustrated in a partially fired condition; and FIG. 65 is a partial cross-sectional elevational view of the surgical stapling instrument of FIG. 64 illustrated in a partially fired condition.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
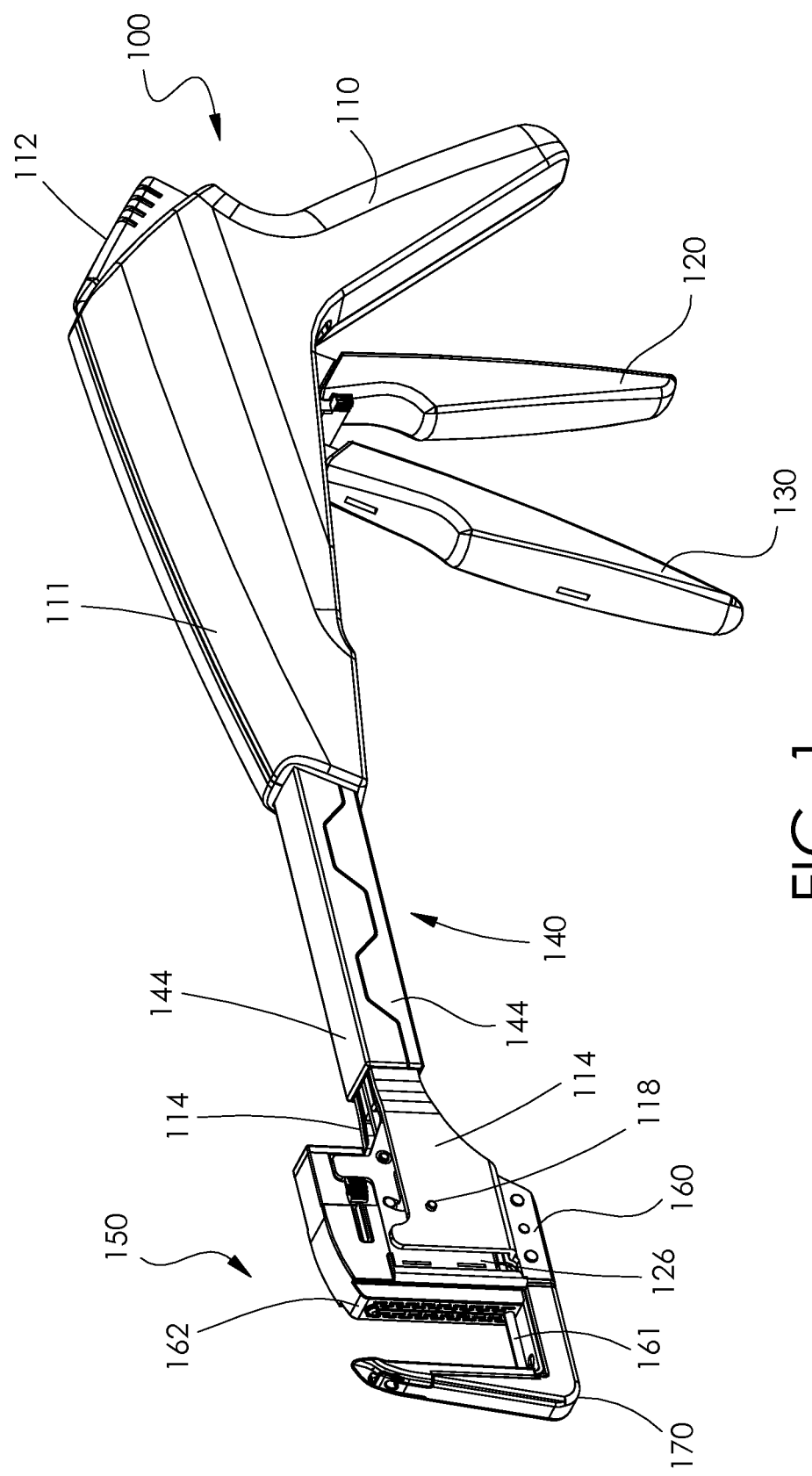
FIG. 1 is a perspective view of a surgical stapling instrument in accordance with at least one embodiment.

Applicant of the present application owns the following patent applications that were filed on Jul. 30, 2015 and which are each herein incorporated by reference in their respective entireties:

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT;

U.S. patent application Ser. No. 14/813,266, entitled SURGICAL INSTRUMENT COMPRISING SYSTEMS FOR PERMITTING THE OPTIONAL TRANSECTION OF TISSUE; and U.S. patent application Ser. No. 14/813,274, entitled SURGICAL INSTRUMENT COMPRISING A SYSTEM FOR BYPASSING AN OPERATIONAL STEP OF THE SURGICAL INSTRUMENT.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Certain previous surgical stapling instruments are disclosed in:

European Patent Application No. EP 795298, entitled LINEAR STAPLER WITH IMPROVED FIRING STROKE, which was filed on Mar. 12, 1997;

U.S. Pat. No. 5,605,272, entitled TRIGGER MECHANISM FOR SURGICAL INSTRUMENTS, which issued on Feb. 25, 1997;

U.S. Pat. No. 5,697,543, entitled LINEAR STAPLER WITH IMPROVED FIRING STROKE, which issued on Dec. 16, 1997;

U.S. Patent Application Publication No. 2005/0246881, entitled METHOD FOR MAKING A SURGICAL STAPLER, which published on Nov. 10, 2005;

U.S. Patent Application Publication No. 2007/0208359, entitled METHOD FOR STAPLING TISSUE, which published on Sep. 6, 2007;

U.S. Pat. No. 4,527,724, entitled DISPOSABLE LINEAR SURGICAL STAPLING INSTRUMENT, which issued on Jul. 9, 1985;

U.S. Pat. No. 5,137,198, entitled FAST CLOSURE DEVICE FOR LINEAR SURGICAL STAPLING INSTRUMENT, which issued on Aug. 11, 1992; and U.S. Pat. No. 5,405,073, entitled FLEXIBLE SUPPORT SHAFT ASSEMBLY, which issued on Apr. 11, 1995, the entire disclosures of which are incorporated by reference herein.

Figure 2:
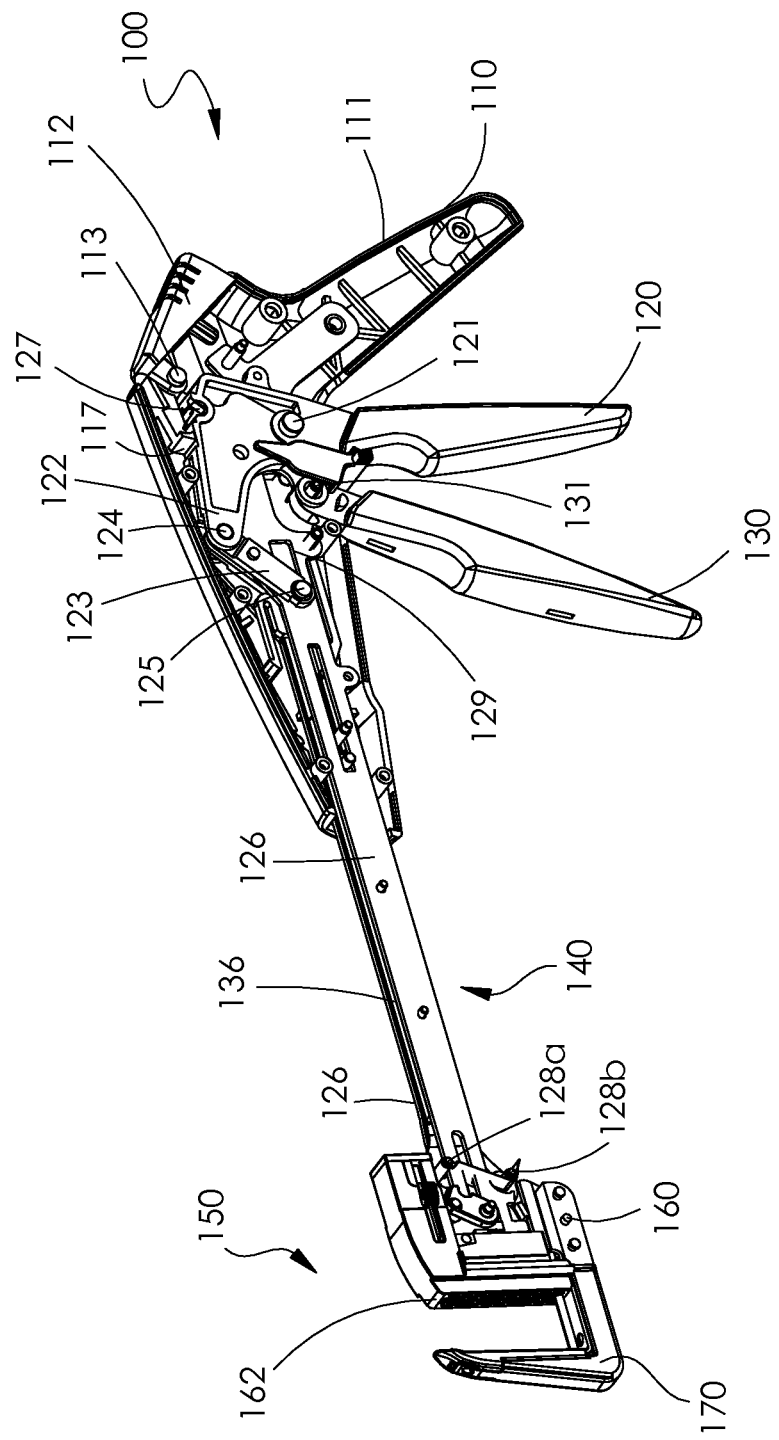
FIG. 2 is a perspective view of the surgical stapling instrument of FIG. 1 with components thereof removed for the purpose of illustration.
Figure 3:
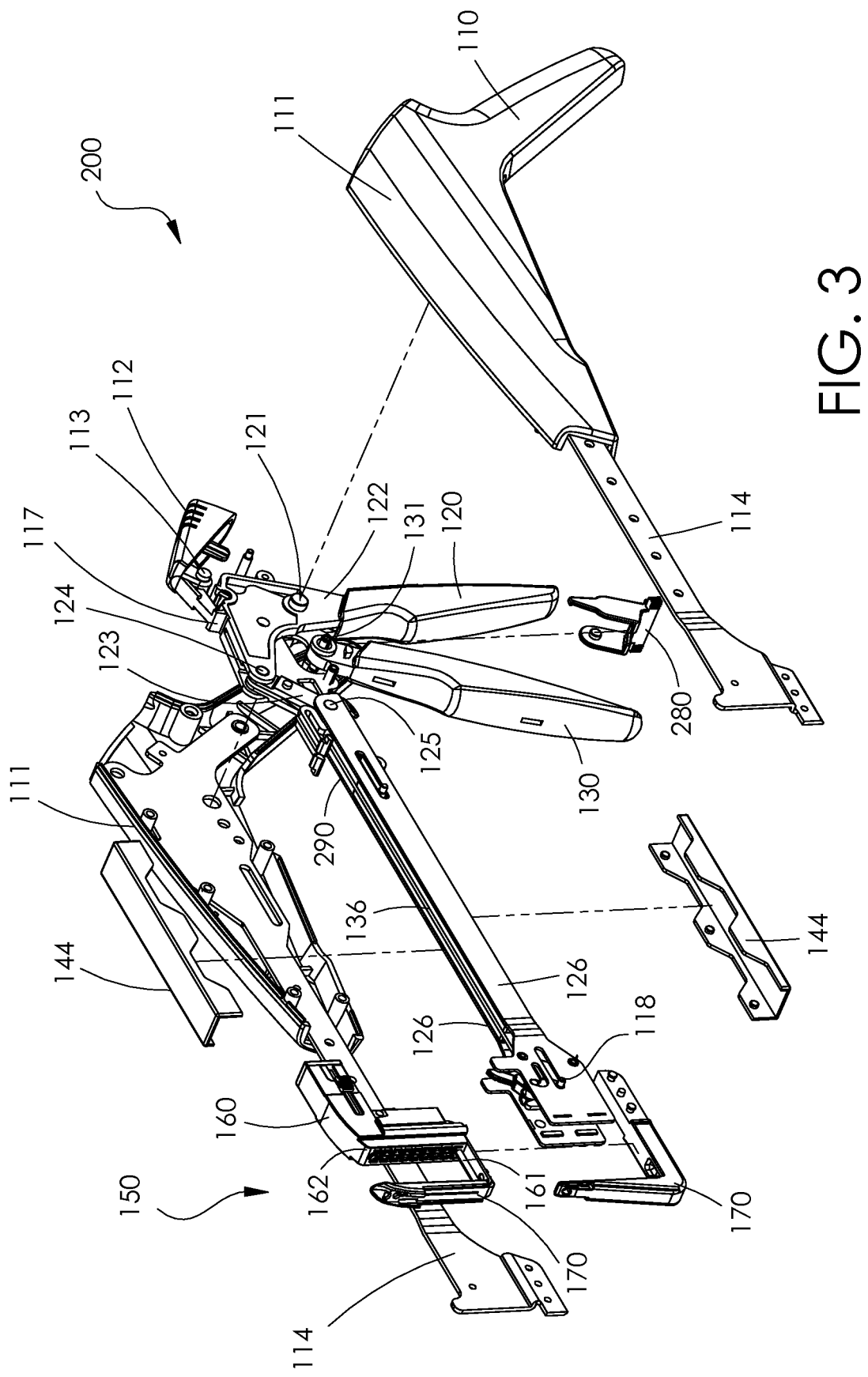
FIG. 3 is an exploded perspective view of a surgical stapling instrument including a handle, a shaft, and an end effector in accordance with at least one embodiment.
Figure 4:
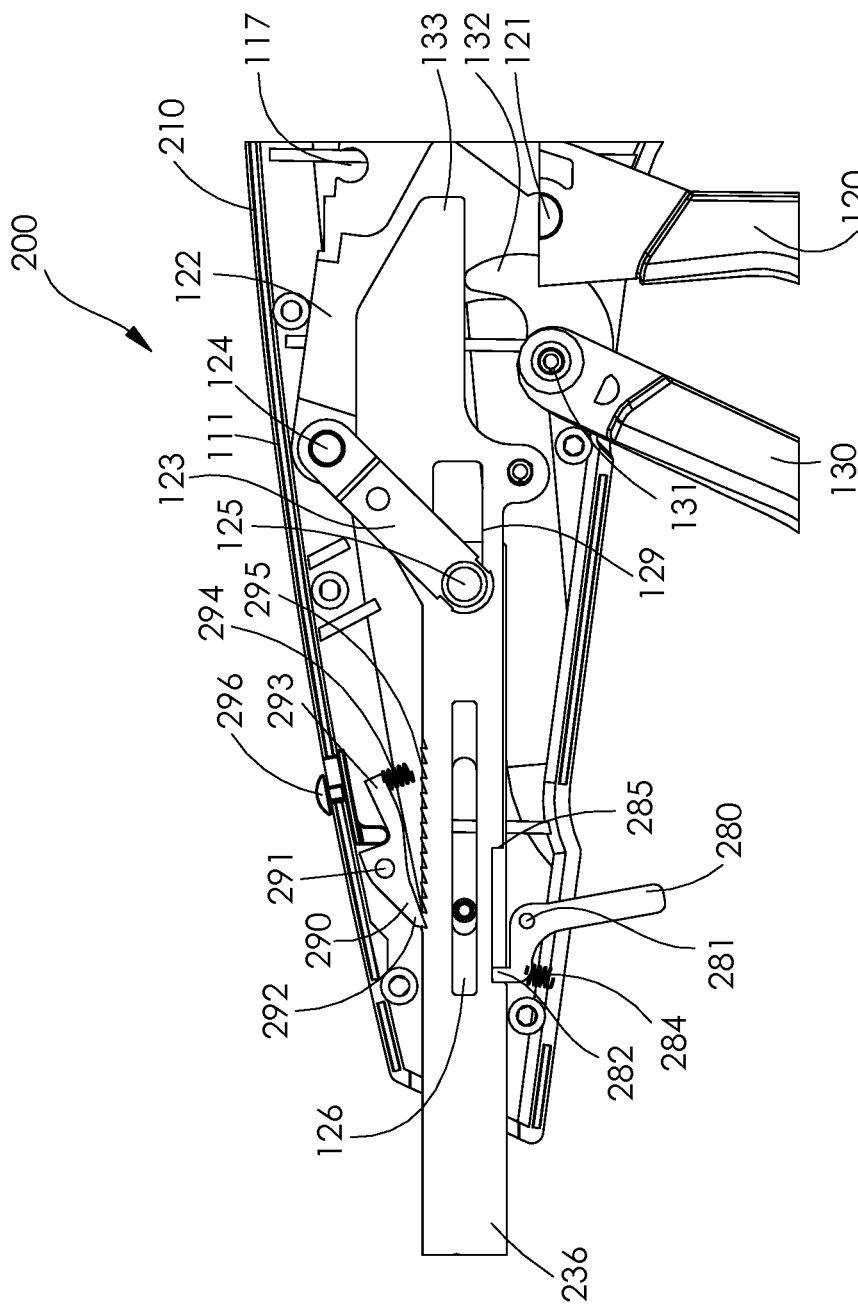
FIG. 4 is a partial cross-sectional elevational view of the handle of FIG. 3 illustrated in an unclamped, unfired configuration.
Figure 5:
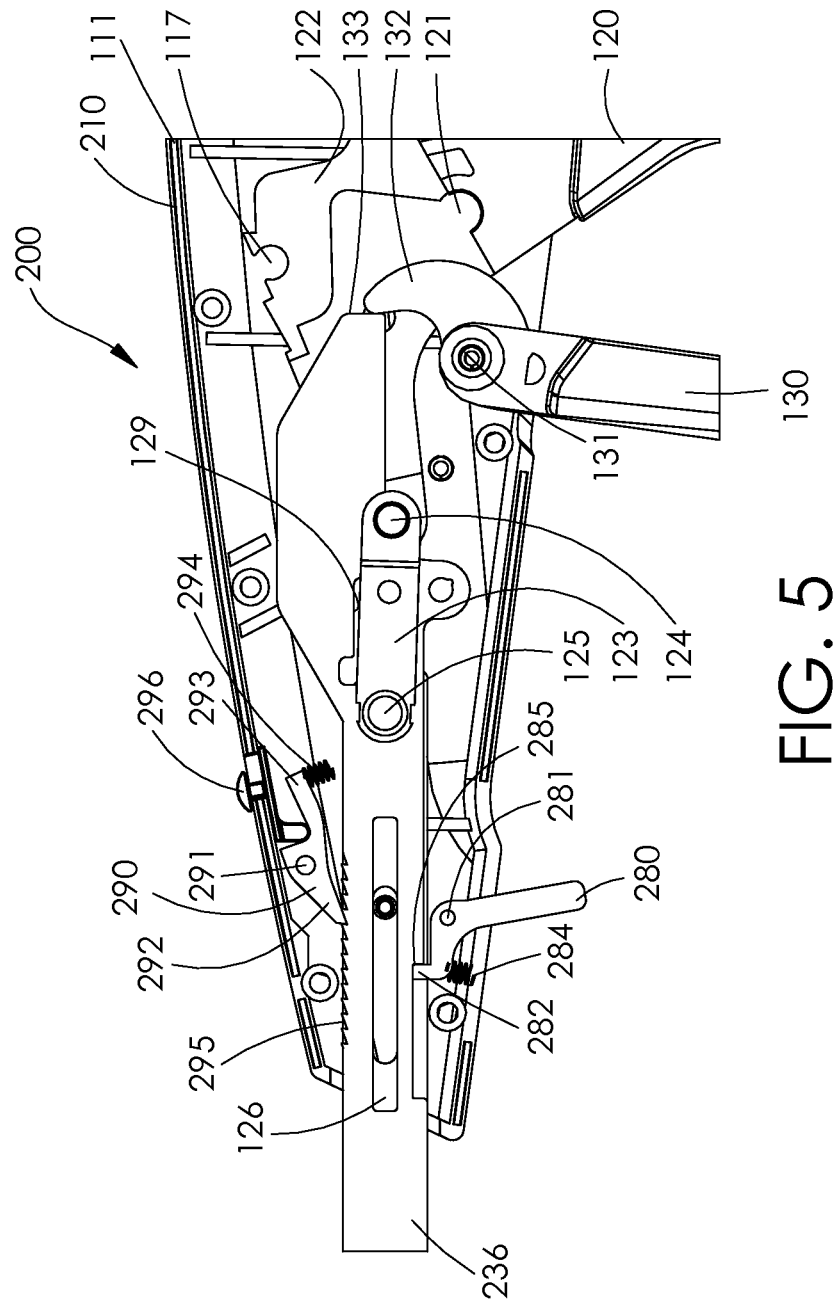
FIG. 5 is a partial cross-sectional elevational view of the handle of FIG. 3 illustrated in a clamped, unfired configuration.

A surgical stapling instrument 100 is disclosed in FIGS. 1 and 2. The instrument 100 comprises a handle 110, a shaft 140 extending from the handle 110, and an end effector 150. The handle 110 comprises a housing 111, a frame 114 extending through the shaft 140, a closure trigger 120, and a firing trigger 130. The operation of the closure trigger 120 moves the end effector 150 between an open configuration (FIG. 1) and a closed configuration. Referring primarily to FIG. 2, the closure trigger 120 is pivotably mounted to the handle housing 111 about a pivot 121 and includes a drive portion 122 which is rotated distally when the closure trigger 120 is moved between an open position (FIG. 1) and a closed position. The closure trigger 120 is part of a closure drive which further includes links 123 and closure bars 126. The links 123 are rotatably pinned to the drive portion 122 of the closure trigger 120 about a pin 124 and the links 123 are rotatably pinned to the closure bars 126 about a pin 125. When the drive portion 122 of the closure trigger 120 is rotated distally, the drive portion 122 drives the closure bars 126 to move a staple cartridge 160 of the end effector 150 toward an anvil 170 of the end effector 150 in order to clamp tissue between the staple cartridge 160 and the anvil 170 during a closure stroke of the closure drive. The drive portion 122 comprises a lock slot 127 defined therein which is configured to receive the distal end 117 of a closure lock 112 when the closure trigger 120 reaches its fully clamped position. The closure lock 112 is rotatably mounted to the handle housing 111 about a pivot pin 113 and is biased against the drive portion 122 of the closure trigger 120 by a biasing member, such as a spring, for example.

The operation of the firing trigger 130 fires the staples removably stored in the staple cartridge 160 toward the anvil 170. Referring primarily to FIG. 2, the firing trigger 130 is pivotably mounted to the handle housing 111 about a pivot 131 and includes a drive portion which is rotated distally when the firing trigger 130 is moved between an unactuated position (FIG. 1) and an actuated position. The firing trigger 130 is part of a firing drive which further includes a firing bar 136 which is driven distally when the firing trigger 130 is moved toward its actuated position. The firing drive also includes a staple driver and a cutting member which are advanced distally by the firing bar 136 during a firing stroke of the firing drive. The frame 114, the closure bars 126, and the firing bar 136 are surrounded, or at least substantially surrounded by a shaft housing 144.

The handle 110 can further comprise a firing return spring configured to return the firing trigger 130 back to its unactuated position to reset the firing system after the firing stroke has been completed and the firing trigger 130 has been released by the clinician. Similarly, the handle 110 can further comprise a closure return spring configured to return the closure trigger 120 back to its open position and reset the closure system after the closure lock 112 has been depressed by the clinician to disengage the closure lock 112 from the lock slot 127.

With regard to the embodiment disclosed in FIGS. 1 and 2, the firing trigger 130 is actuated to staple and incise the tissue clamped in the end effector 150 in a single stroke of the firing trigger 130. Moreover, the embodiment disclosed in FIGS. 1 and 2 does not provide the clinician operating the instrument with the ability to pause between the staple firing and the tissue cutting functions of the firing system. In addition, the instrument does not provide the clinician with any feedback as to whether the instrument is performing the staple forming function or the tissue cutting function. Provided below are various improvements to this instrument.

Figure 6:
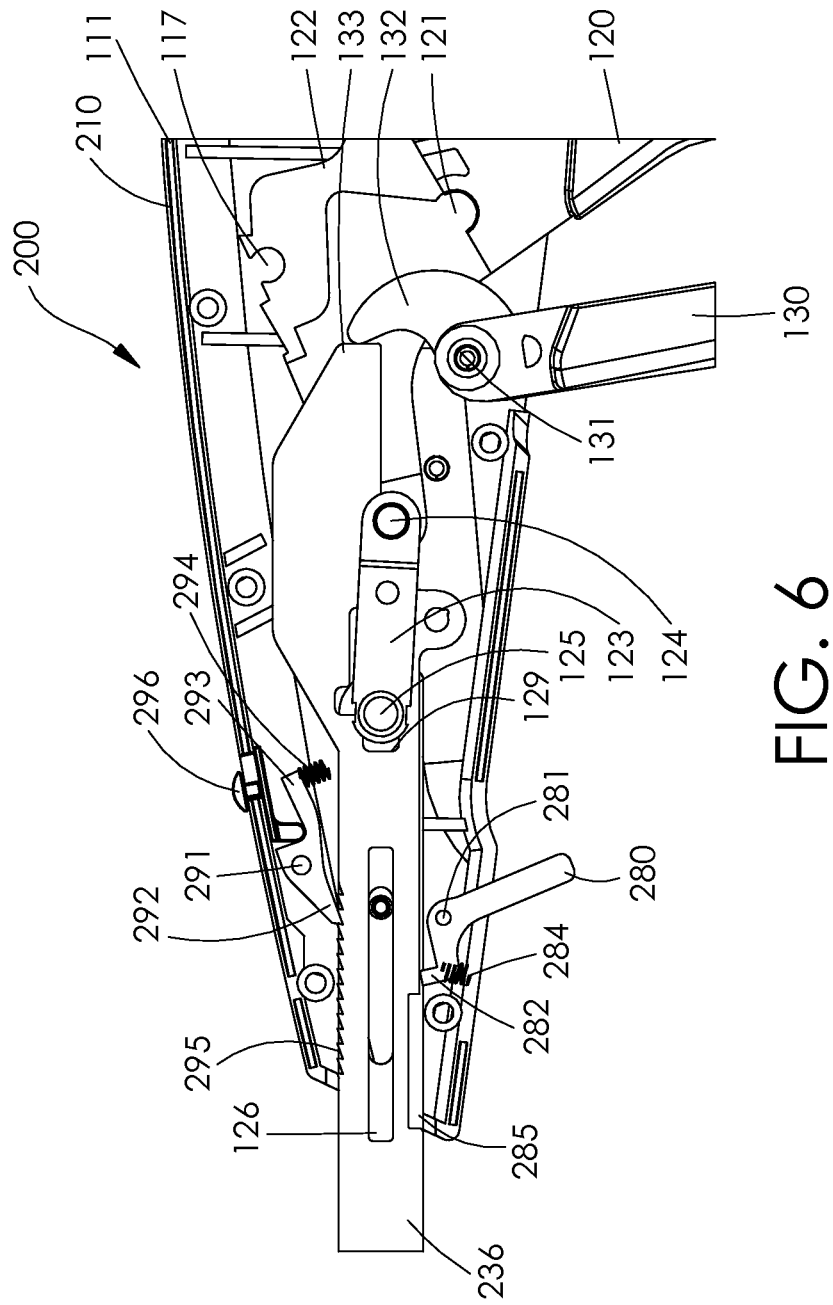
FIG. 6 is a partial cross-sectional elevational view of the handle of FIG. 3 illustrated in a clamped, partially-fired configuration.
Figure 7:
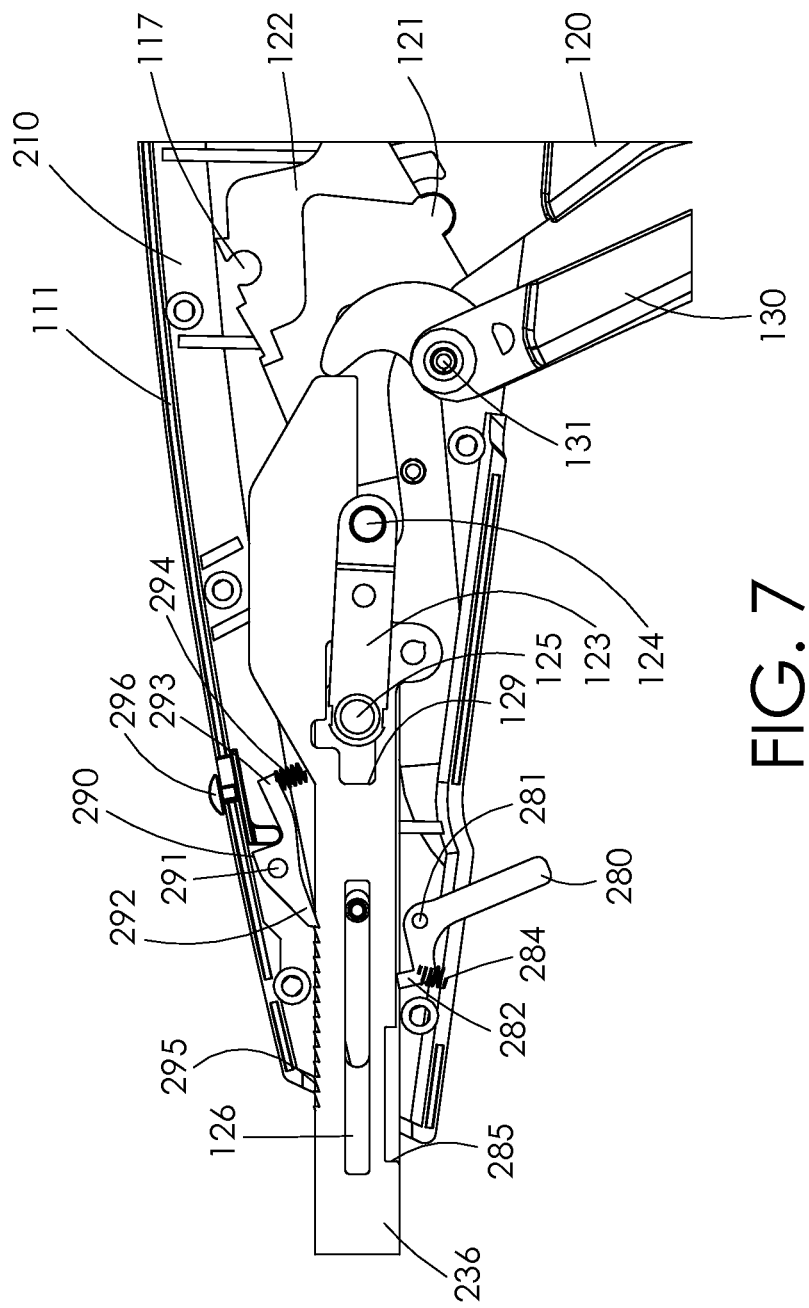
FIG. 7 is a partial cross-sectional elevational view of the handle of FIG. 3 illustrated in a clamped, fully-fired configuration.
Figure 8:
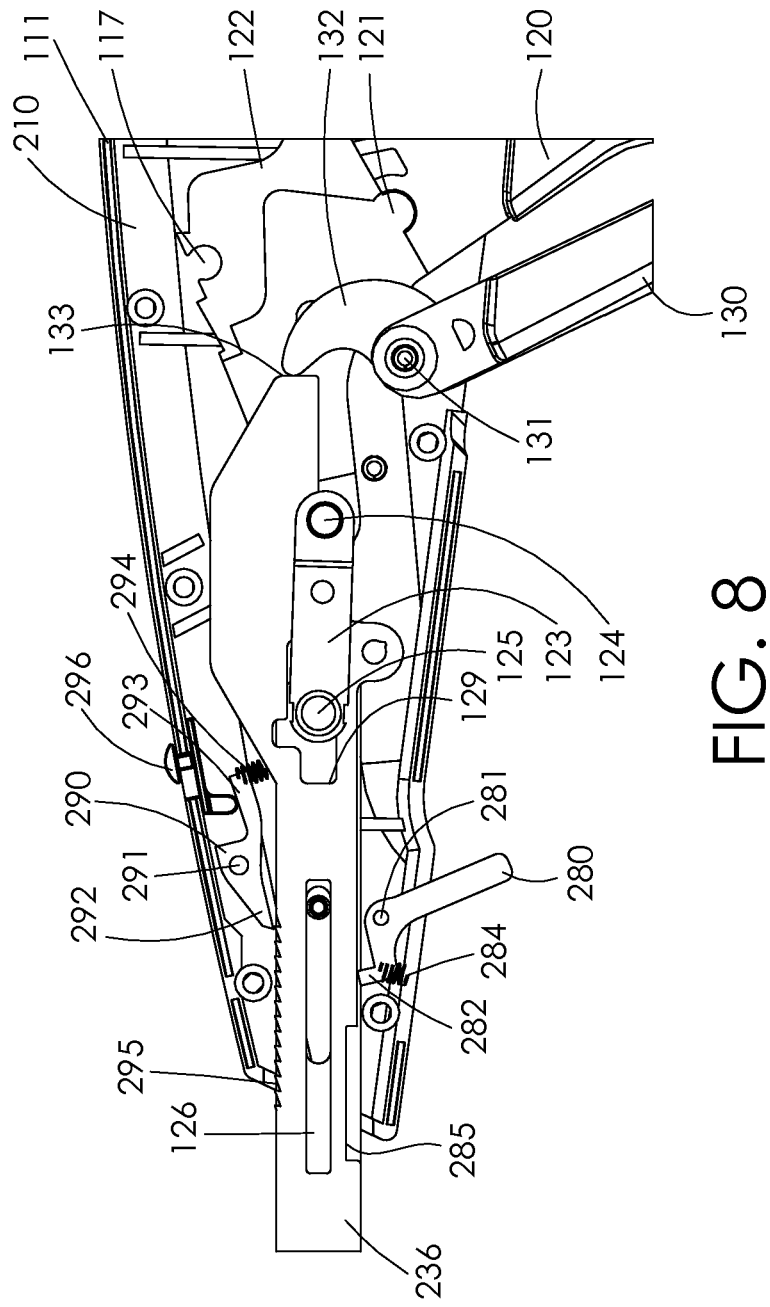
FIG. 8 is a partial cross-sectional elevational view of the handle of FIG. 3 prior to being returned back to an unclamped configuration.

A surgical stapling instrument 200 is illustrated in FIGS. 3-8 and is similar to the instrument 100 and/or the other surgical instruments disclosed herein in many respects. For instance, referring primarily to FIG. 4, the instrument 200 comprises a closure trigger 120 which, when actuated, drives the closure bars 126 distally to close the end effector of the instrument 200. The actuation of the closure trigger 120 also at least partially advances a firing bar 236 of the firing system distally to a pre-staged position in which a firing trigger 130 can then be actuated to fire the staples from a staple cartridge positioned in the end effector. The firing trigger 130 comprises a drive portion 132 which is aligned with a proximal end 133 of the firing bar 236 once the firing bar 236 has been moved into its pre-staged position. At such point, referring now to FIG. 5, the firing trigger 130 can be actuated to move the firing bar 236 distally and fire the staples from the staple cartridge. The actuation of the firing trigger 130 and the distal advancement of the firing bar 236, however, are limited by a stop, or switch, 280. The switch 280 stops the distal advancement of the firing bar 236 before the firing bar 236 transects the tissue captured within the end effector. In order to transect the tissue, the switch 280 is actuated to release the firing bar 236, as illustrated in FIG. 6, so that the firing stroke of the firing actuator 130 can be completed, as illustrated in FIG. 7. In such a way, the firing of the staples and the transection of the tissue can comprise separate and distinct operational steps of the instrument 200. In such instances, the clinician can choose when to cut the tissue and/or whether to cut the tissue.

As discussed above, and referring primarily to FIG. 5, the firing bar 236 is stopped by the switch 280 during the distal advancement of the firing bar 236. The firing bar 236 comprises a slot 285 defined therein and the switch 280 is removably positioned in the slot 285. The switch 280 is pivotably mounted to the handle housing 111 about a pivot pin 281 and comprises a lock arm 282 which is positioned in the slot 285. The firing bar 236 can be advanced distally by the firing trigger 130 until the proximal end of the slot 285 contacts the lock arm 282. At such point, further distal movement of the firing bar 236 is prevented by the lock arm 282. A spring 284 is positioned between the lock arm 282 and the handle housing 111 to bias the lock arm 282 into the slot 285 and hold the lock arm 282 in position until the switch 280 is actuated, as illustrated in FIG. 6. When the switch 280 is actuated, the lock arm 282 is rotated out of the slot 285 and the firing bar 236 can then be advanced distally once again, as illustrated in FIG. 7. When the firing bar 236 is advanced toward the end of its firing stroke, the lock arm 282 is no longer registered with the slot 285 and the spring 284 biases the lock arm 282 against the bottom surface of the firing bar 236. When the firing bar 236 is retracted toward its unfired position after the tissue has been cut, the lock arm 282 can become aligned with the slot 285 once again and the spring 284 can bias the lock arm 282 into the slot 285.

Further to the above, the staples are completely formed at the point when the firing bar 236 is stopped by the switch 280. In such instances, the tissue can be completely secured by the staples before a cutting portion of the firing bar 236 is advanced to cut the tissue. Alternative embodiments are envisioned in which the staples are only partially formed when the firing bar 236 is stopped by the switch 280. In such embodiments, the tissue is cut at the same time that the staple formation is completed. In either event, a pause in the operation of the instrument 200 after a first step is provided which requires the intervention of a clinician to selectively decide whether to perform a second step eventhough both steps are performed by one actuation of a trigger. Stated another way, the switch 280 stops the firing trigger 130 during its actuation stroke and the stopping function of the switch 280 must be defeated before the actuation stroke can be completed. The switch 280 can be operated at a time deemed suitable by the clinician. In certain instances, the switch 280 could be operated right after the switch 280 stops the firing bar 236 or, alternatively, after a period of time. In some instances, the switch 280 can be operated prior to stopping the firing bar 236 thereby permitting the first and second steps to be selectively combined.

Further to the above, the clinician may or may not remove their hand from the firing trigger 130 during the pause provided by the switch 280. In either event, it is desirable to prevent the firing bar 236 from retracting suddenly and/or unintentionally. To this end, the instrument 200 further comprises a lock 290 which is configured to releasably hold the firing bar 236 in position. The lock 290 comprises a ratchet system; however, any suitable lock may be utilized. The lock 290 is rotatably mounted to the housing 111 about a pivot pin 291 and comprises a pawl 292 extending therefrom which is configured to engage ratchet teeth 295 defined in the firing bar 236. The lock 290 further comprises a proximal arm 293 and a spring 294 positioned intermediate the proximal arm 293 and the housing 111 configured to bias pawl 292 into engagement with the teeth 295. When the pawl 292 is engaged with the teeth 295, the lock 290 is configured to permit the firing bar 236 to move distally but prevent the firing bar 236 from moving proximally. The handle 210 of the instrument 200 further comprises a switch 296 configured to engage the proximal arm 293 of the lock 290 and rotate the pawl 292 away from the firing bar 236 and disengage the pawl 292 from the teeth 295. At such point, the firing bar 236 can be retracted.

In order to retract the firing bar 236, the clinician can push the closure lock 112 to disengage the closure lock 112 from the closure trigger 120 and move the closure trigger 120 to its unactuated position (FIG. 4) and/or the handle 210 can include a return spring configured to bias the closure trigger 120 toward its unactuated position. In either event, the movement of the closure trigger 120 toward its unactuated position can pull the links 123 proximally which can, in turn, pull the closure bars 126 and the firing bar 236 proximally. More particularly, the pin 125 which connects the links 123 also extends through longitudinal apertures defined in the closure bars 126 and the firing bar 236, such as longitudinal aperture 129 defined in the firing bar 236, for example, and, when the links 123 are pulled proximally by the closure trigger 120, the pin 125 can contact the proximal end of the aperture 129, and the proximal end of the longitudinal apertures defined in the closure bars 126, and pulls the firing bar 236 and the closure bars 126 proximally. The proximal movement of the firing bar 236 can also push the firing actuator 120 back to its unactuated position and/or the firing actuator 120 can be returned to its unactuated position by a return spring. In either event, the lock 290 can be reset by pushing the switch 296 distally to permit the pawl 292 to be re-engaged with the teeth 295 once the firing bar 236 has been returned to its unactuated position.

Further to the above, the pawl 292 can be configured to generate audible sounds, such as clicks, for example, as the teeth 295 of the firing bar 236 slide under the pawl 292. Such audible sounds can provide feedback to the surgeon that the firing bar 236 is moving distally. Such audible sounds can also provide feedback to the surgeon regarding the speed of the firing bar 236, as sounds emitted at a faster pace would indicate that the firing bar 236 is moving at a faster speed while sounds emitted at a lower pace would indicated that the firing bar 236 is moving at a slower speed.

A surgical stapling instrument 300 is illustrated in FIGS. 9-15 and is similar to the instruments 100, 200, and/or the other surgical instruments disclosed herein, in many respects. The instrument 300 comprises an end effector 350 including a staple cartridge 360 and an anvil 170. In use, tissue is positioned between the staple cartridge 360 and the anvil 170 and then trapped in the end effector 350 by a deployable tissue pin 379. The tissue pin 379 is stored in the staple cartridge 360 in a pin cavity 378 and moved distally toward the anvil 170. The tissue pin 379 can be pushed distally when the staple cartridge 360 is moved into a closed position, as discussed in greater detail further below. The tissue pin 379 comprises lateral gripping members 377 which are configured to permit the clinician to push the pin 379 toward the anvil 170 and/or retract the pin 379 into the staple cartridge 360. The staple cartridge 360 comprises lateral slots 375 defined therein configured to guide the longitudinal movement of the gripping members 377 and the tissue pin 379. The movement of the tissue pin 379 is limited by the anvil 170 and a proximal end plate 376.

Figure 9:
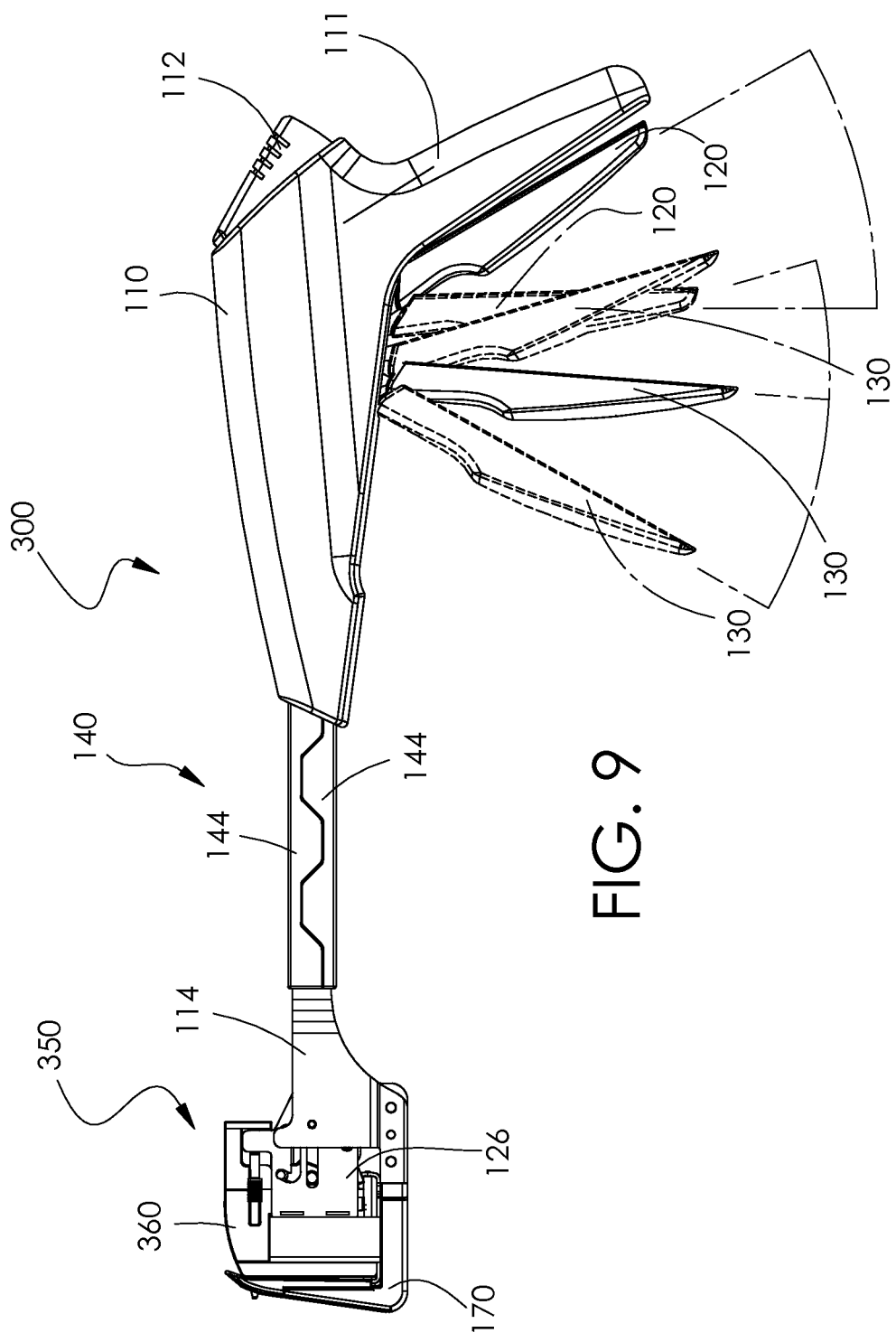
FIG. 9 is an elevational view of a surgical stapling instrument including a handle, a shaft, and an end effector in accordance with at least one embodiment.
Figure 10:
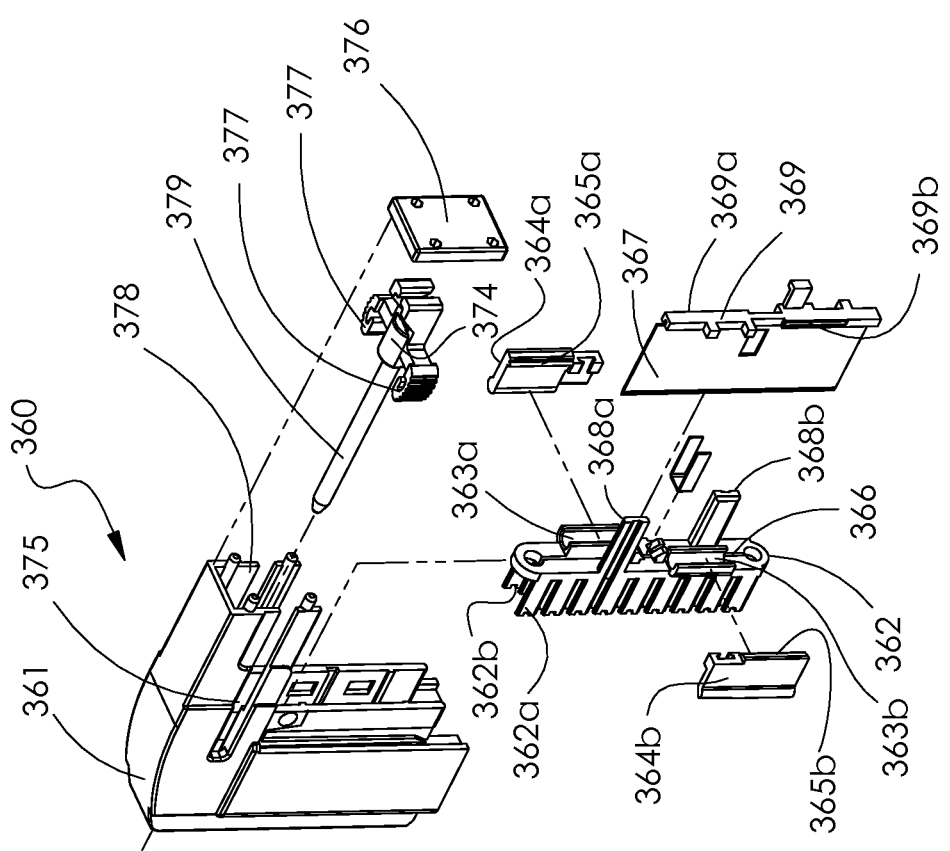
FIG. 10 is an exploded perspective view of a staple cartridge for use with the surgical stapling instrument of FIG. 9.

Referring primarily to FIG. 9, the instrument 300 further comprises a closure trigger 120 which, when actuated, drives closure bars 126 distally to close the end effector 350 of the instrument 300 and clamp the tissue between the staple cartridge 360 and the anvil 170. The instrument 300 also comprises a firing trigger 130 which, when actuated, pushes a firing bar 336 distally to eject the staples from the staple cartridge 360 positioned in the end effector 350. Referring to FIGS. 10-15, the staple cartridge 360 comprises a cartridge body 361 including a plurality of staple cavities 361a, 361b and a knife slot 366 defined therein. The staple cavities 361a are positioned on a first side of the knife slot 366 and the staple cavities 361b are positioned on a second side of the knife slot 366. Although not illustrated, staples are stored in the staple cavities 361a, 361b and are ejected from the staple cavities 361a, 361b when a staple driver 362 is moved toward the anvil 170 by the firing bar 336. The staple driver 362 comprises a plurality of staple supports, or cradles, 362a configured to drive the staples stored in the staple cavities 361a and a plurality of staple supports, or cradles, 362b configured to drive the staples stored in the staple cavities 361b. The staple driver 362 further comprises longitudinal guides 368a and 368b which are configured to control and/or constrain the movement of the staple driver 362 to a longitudinal path.

Further to the above, the staple cartridge 360 comprises a cutting member, or knife, 367 which is slidably positioned in the knife slot 366. The staple driver 362 comprises a first knife latch 364a and a second knife latch 364b which are configured to releasably hold the knife 366 and the staple driver 362 together, as described in greater detail below. The staple driver 362 comprises a first pivot joint 363a and a second pivot joint 363b. The first knife latch 364a is rotatably positioned in the first pivot joint 363a and the second knife latch 364b is rotatably positioned in the second pivot joint 363b. The first knife latch 364a and the second knife latch 364b are rotatable between a clamped position (FIGS. 12 and 13) in which they are engaged with the knife 367 and an unclamped position (FIGS. 14 and 15) in which they are disengaged from the knife 367. When the first knife latch 364a and the second knife latch 364b are in their clamped position, the staple driver 362 and the knife 367 move together. In use, the staple driver 362 and the knife 367 are pushed distally by the firing bar 336 to move the staples between an unfired position (FIG. 12) and a fired position (FIG. 13). As can be appreciated from FIG. 13, the cutting edge of the knife 367 does not emerge from the cartridge body 361 to cut the tissue captured between the cartridge body 361 and the anvil 170 when the staple driver 362 is moved into its fired position. Instead, the knife 367 is in a staged position below the deck surface of the cartridge body 361.

Figure 11:
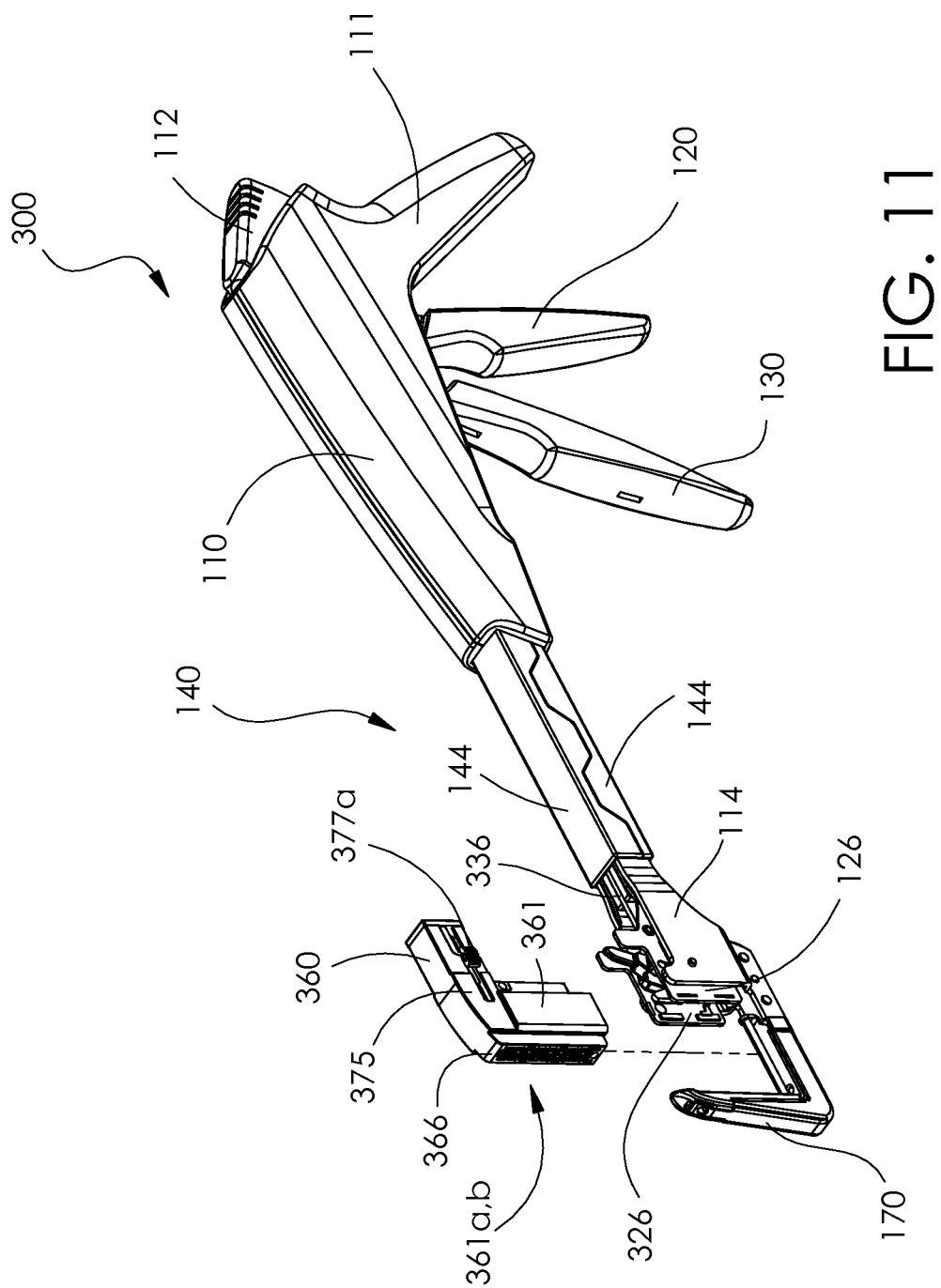
FIG. 11 is a perspective view illustrating the staple cartridge of FIG. 10 being assembled to the surgical stapling instrument of FIG. 9.
Figure 12:
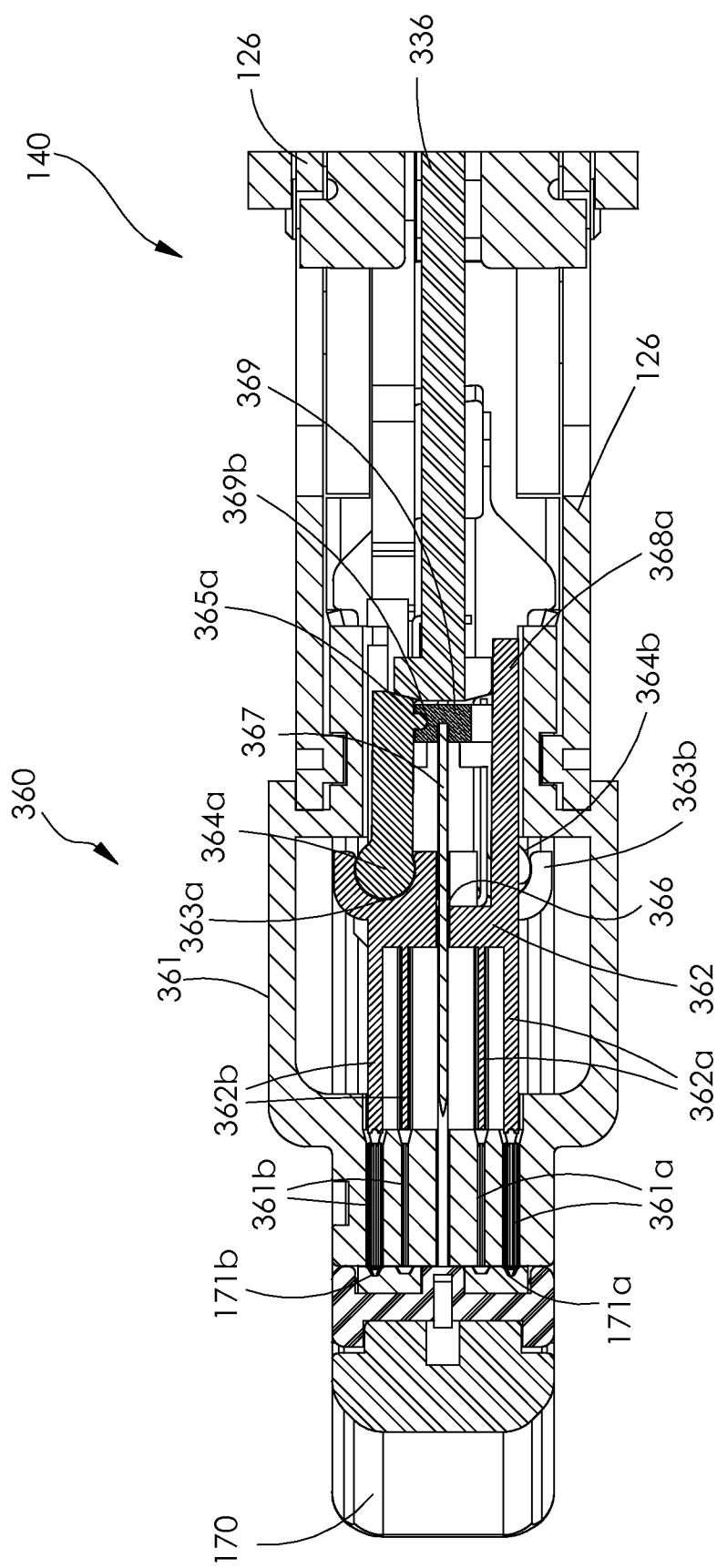
FIG. 12 is a cross-sectional view illustrating the staple cartridge of FIG. 10 positioned in the end effector of the surgical instrument of FIG. 9 and illustrating the end effector in a clamped configuration.
Figure 13:
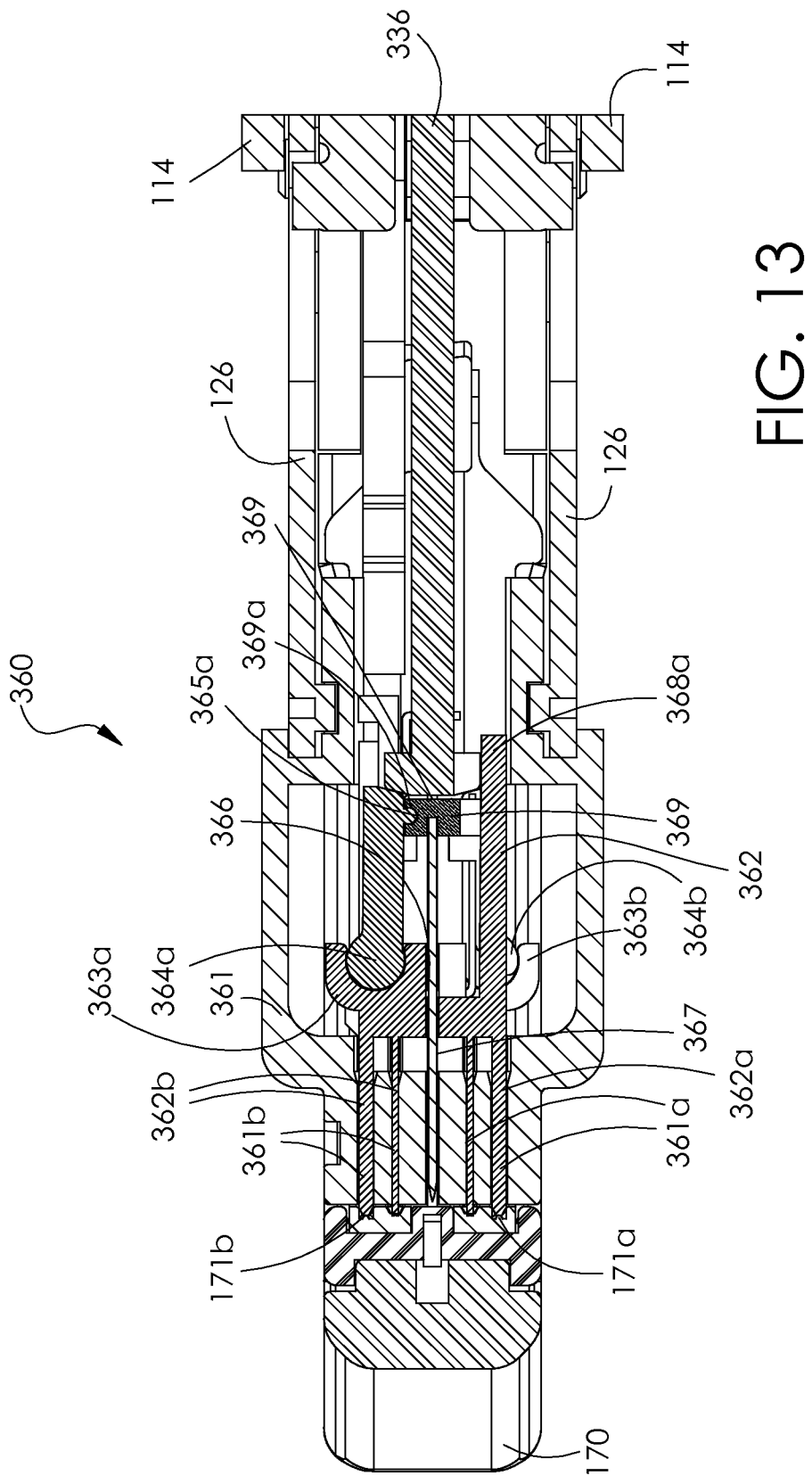
FIG. 13 is a cross-sectional view illustrating the staple cartridge of FIG. 10 positioned in the end effector of the surgical instrument of FIG. 9 and illustrating staple drivers of the end effector being moved into a fired configuration by a firing system.
Figure 14:
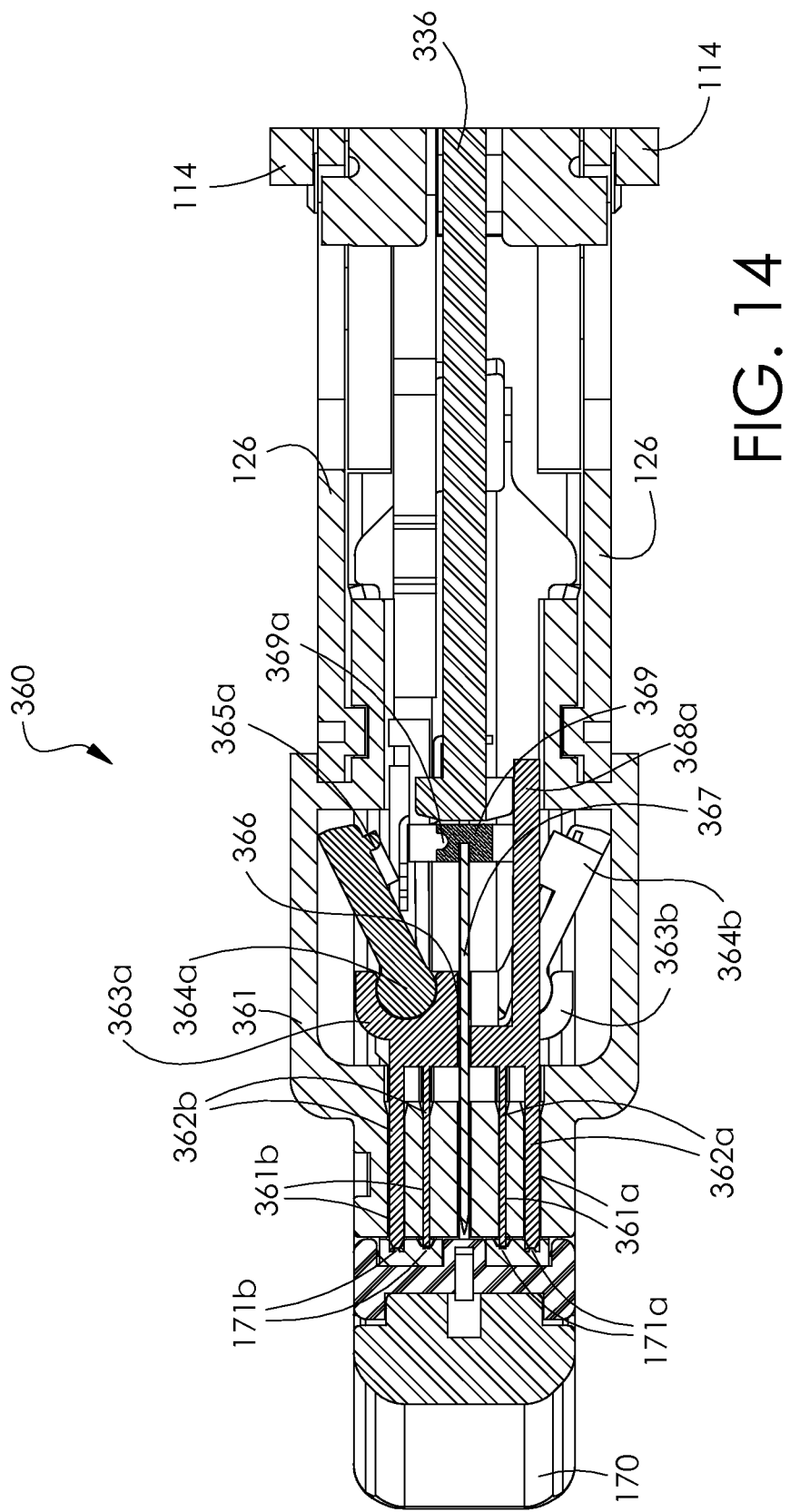
FIG. 14 is a cross-sectional view illustrating the staple cartridge of FIG. 10 positioned in the end effector of the surgical instrument of FIG. 9 and illustrating the staple drivers operably disengaged from the firing system.
Figure 15:
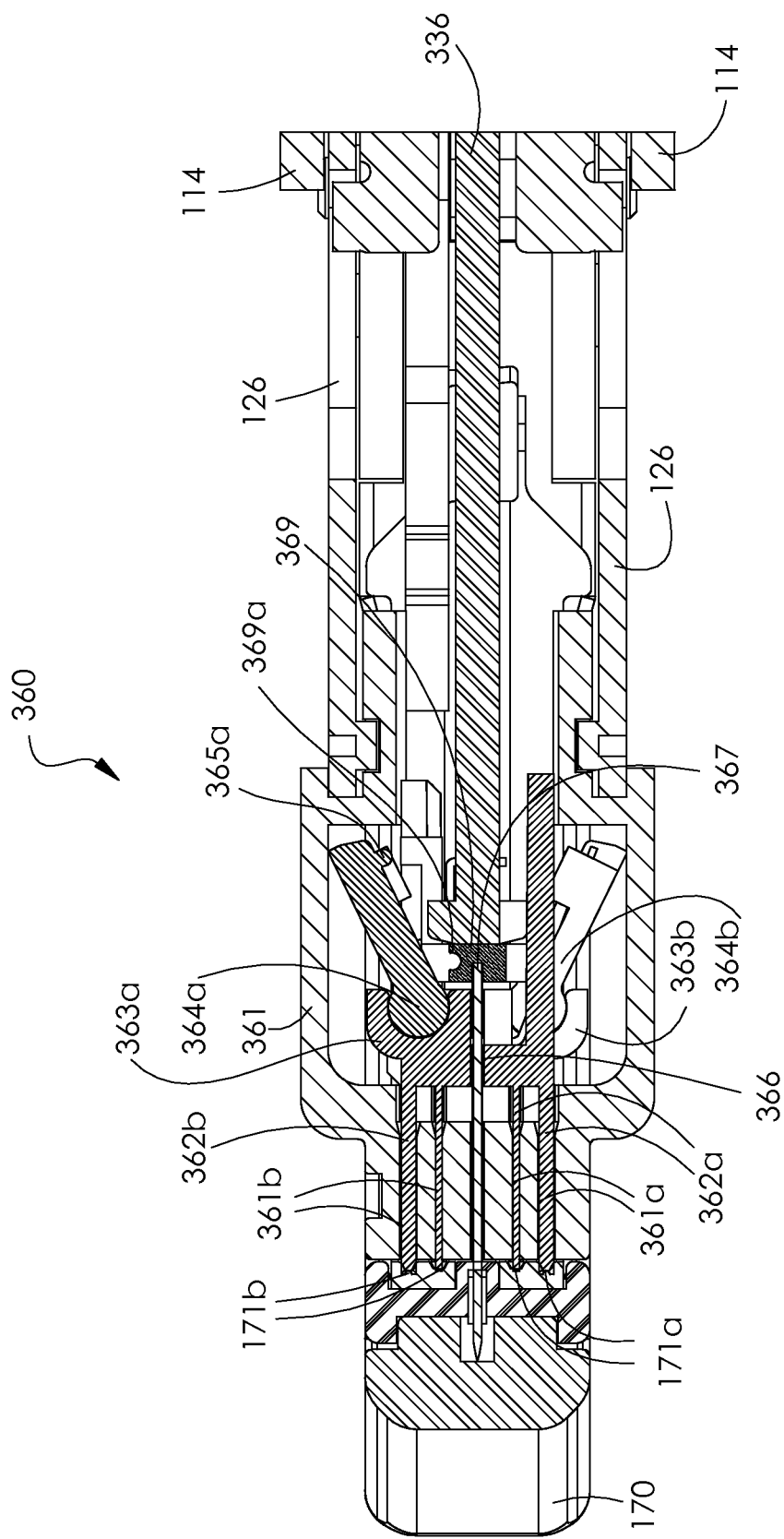
FIG. 15 is a cross-sectional view illustrating the staple cartridge of FIG. 10 positioned in the end effector of the surgical instrument of FIG. 9 and illustrating a cutting member being actuated by the firing system.

As can be seen in FIGS. 12 and 13, the firing bar 336 contacts the first knife latch 364a and the second knife latch 364b to push the staple driver 362 distally. Referring to FIGS. 11-13, the first knife latch 364a is releasably engaged with a knife support 369 such that the motion of the staple driver 362 can be transferred to the knife 367. More specifically, the first knife latch 364a comprises a ridge 365a positioned in a recess 369a defined in the knife support 369 and, similarly, the second knife latch 364b comprises a ridge 365b positioned in a recess 369b defined the knife support 369. The ridges 365a, 365b are securely received within their respective recesses 369a, 369b such that the driving force delivered by the firing bar 336 is transferred to the staple driver 362 and the knife 367 to deform the staples against the anvil 170. The ridges 365a, 365b and the recesses 369a, 369b are configured such that the ridges 365a, 365b remain engaged with the recesses 369a, 369b until a threshold force is reached wherein, at such point, the knife latches 364a, 364b displace outwardly away from the knife support 369, as illustrated in FIGS. 14 and 15. The threshold force can comprise the force needed to fully form the staples, for example. At such point, the firing bar 336 is no longer operably engaged with the staple driver 362 and the firing bar 336 can move distally relative to the staple driver 362. The firing bar 336 can then contact the knife support 369 directly to drive the knife 367 toward the anvil 170 and transect the tissue. As can be seen in FIG. 15, the knife 367 moves relative to the staple driver 362 after the staple driver 362 has decoupled from the knife 367.

Further to the above, the firing system of the instrument 300 comprises two separate and distinct stages—a first, or staple-firing, stage and a second, or tissue-cutting, stage. The operation of the knife latches 364a, 364b define the boundary between the two stages. When the knife latches 364a, 364b are clamped to the knife 367, the firing system is in its staple-firing state. When the knife latches 364a, 364b are unclamped from the knife 367, the firing system is in its tissue-cutting stage. These two stages are separate and distinct and there is no overlap between them; however, embodiments are envisioned in which at least some overlap between the two stages could exist.

Figure 16:
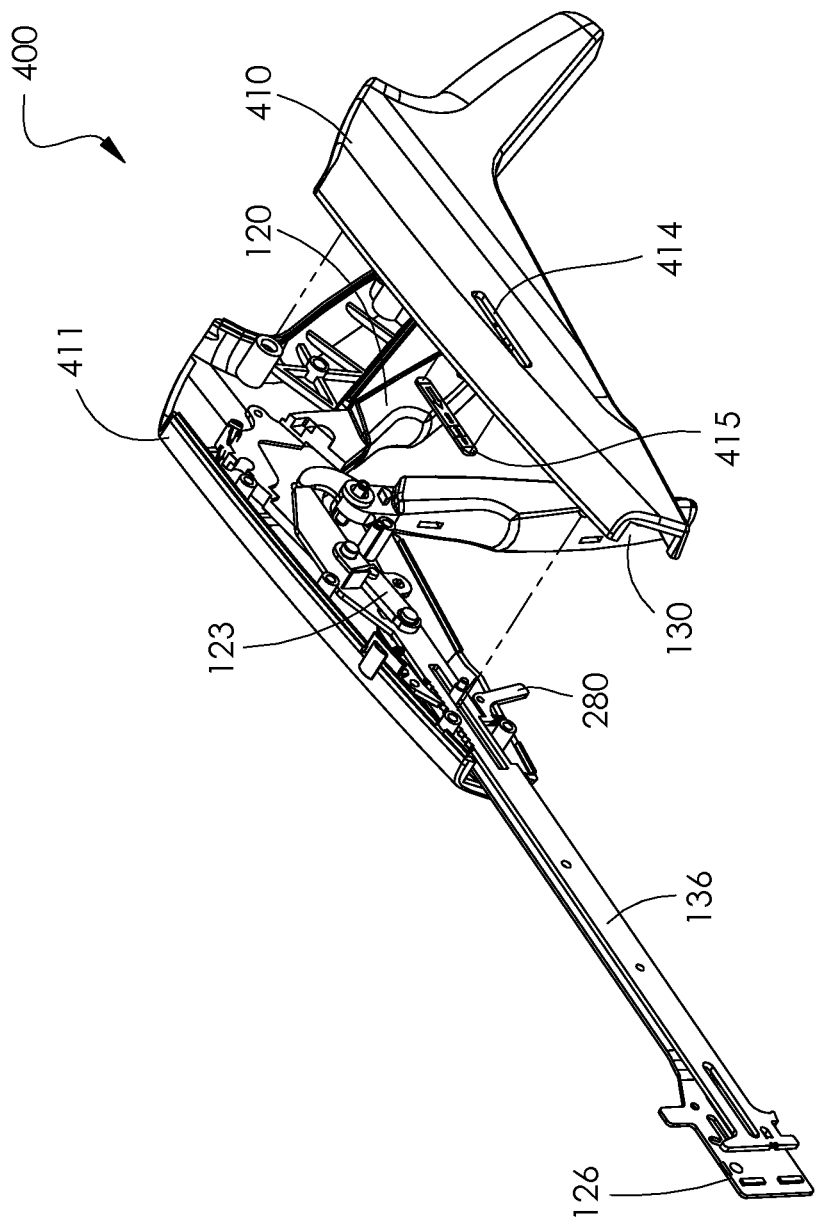
FIG. 16 is an exploded view of a surgical stapling instrument in accordance with at least one embodiment illustrated with components removed for the purpose of illustration.
Figure 17:
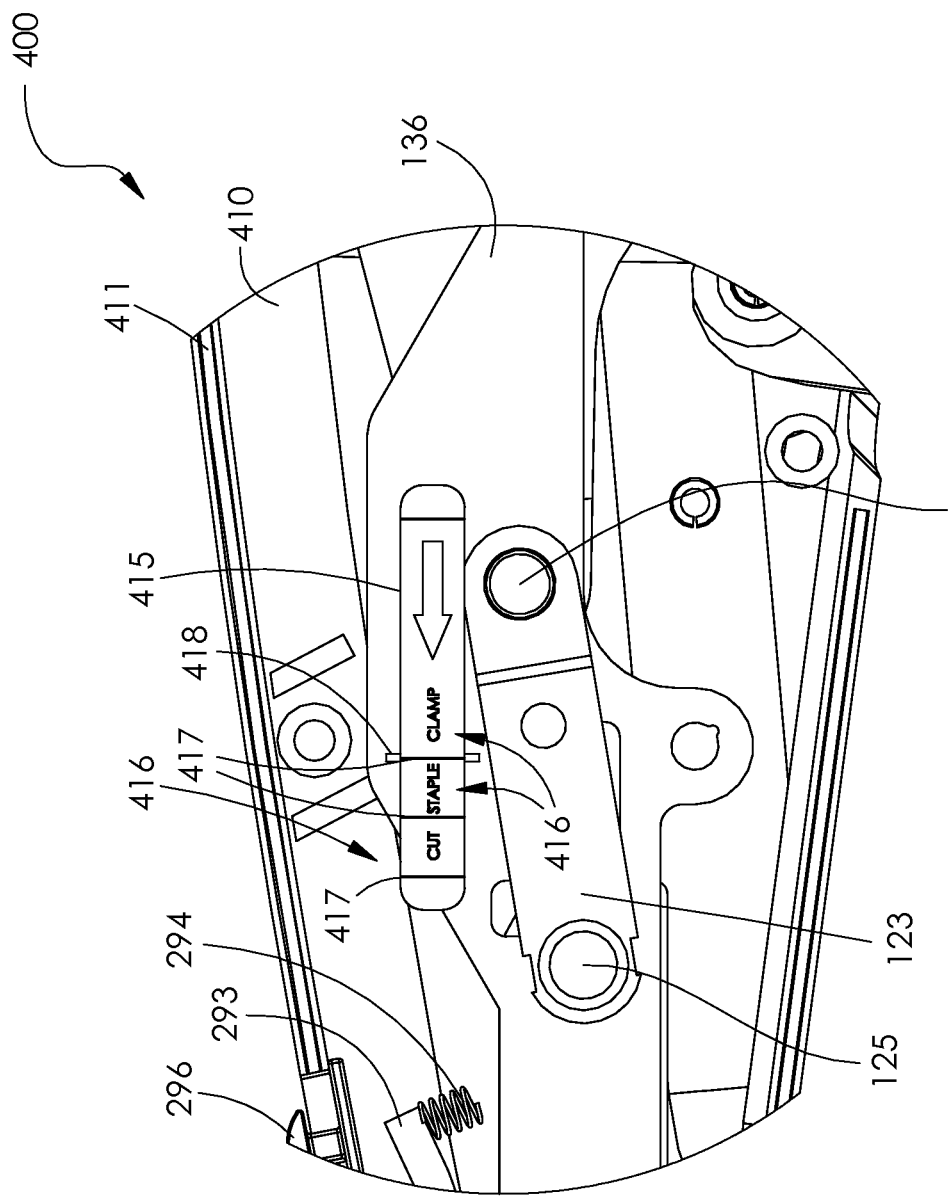
FIG. 17 is a detail view of a progress indicator of the surgical stapling instrument of FIG. 16.

A surgical stapling instrument 400 is illustrated in FIGS. 16 and 17 and is similar to the instrument 100, 200, 300 and/or the other surgical instruments disclosed herein in many respects. For instance, the instrument 400 comprises a handle 410 including a housing 411 which is similar to the housing 111 in many respects. The instrument 400 further comprises closure bars 126 which, further to the above, move a staple cartridge toward an anvil to clamp tissue therebetween. As discussed above, the closure trigger 120 is actuated to move the closure bars 126 distally. As also discussed above, the closure trigger 120 also advances the firing bar 136 into a pre-staged position when the closure trigger 120 is actuated. The firing trigger 130 can then be actuated to move the firing bar 136 distally and fire the staples from the staple cartridge and, subsequently, incise the tissue. Thus, it can be said that firing bar 136 is moved distally during all three operating states—the closure operating state, the staple-firing operating state, and the tissue-incising operating state. The instrument 400 further comprises a progress indicator which reveals the operating state of the instrument 400, as discussed in greater detail below.

Further to the above, referring primarily to FIG. 17, the progress indicator comprises demarcations 418 on the firing bar 136. The demarcations 418 comprise projections extending laterally from the firing bar 136; however, in various other instances, the demarcations 418 could comprise indicia printed on the firing bar 136, for example. The progress indicator further comprises a progress bar 415 positioned in a window 414 defined in the handle housing 411. The progress bar 415 comprises indicia 416 which corresponds to the three operating states of the instrument 400. For instance, the indicia 416 comprises a first indicia "clamp" which corresponds to the tissue clamping operating state, a second indicia "staple" which corresponds to the staple-firing operating state, and a third indicia "cut" which corresponds to the tissue-incising operating state. The progress bar 415 further comprises three lines 417 which correspond to the completion of operating states. In use, the demarcations 418 on the firing bar 136 are aligned with a first line 417 when the closure stroke has been completed, as illustrated in FIG. 17, a second line 417 when the staples have been fully fired, and a third line 417 when the cutting stroke has been completed. Stated another way, the demarcations 418 move distally along the progress bar 415 as the firing bar 136 advances distally to indicate the progress of the firing bar 136. Such movements of the demarcations 418 is observable by the operator of the surgical instrument 400 through the window 414 defined in the handle housing 411. In at least one embodiment, the portion of the progress bar 415 associated with the clamping operating state can be a first color, such as green, for example, the portion of the progress bar 415 associated with the staple-firing operating state can be a second color, such as yellow, for example, and the portion of the progress bar 415 associated with the tissue-incising operating state can be a third color, such as red, for example.

In alternative embodiments, the progress bar 415 can be mounted to the firing bar 136 and the demarcations 418 can extend from the handle housing 411.

Figure 18:
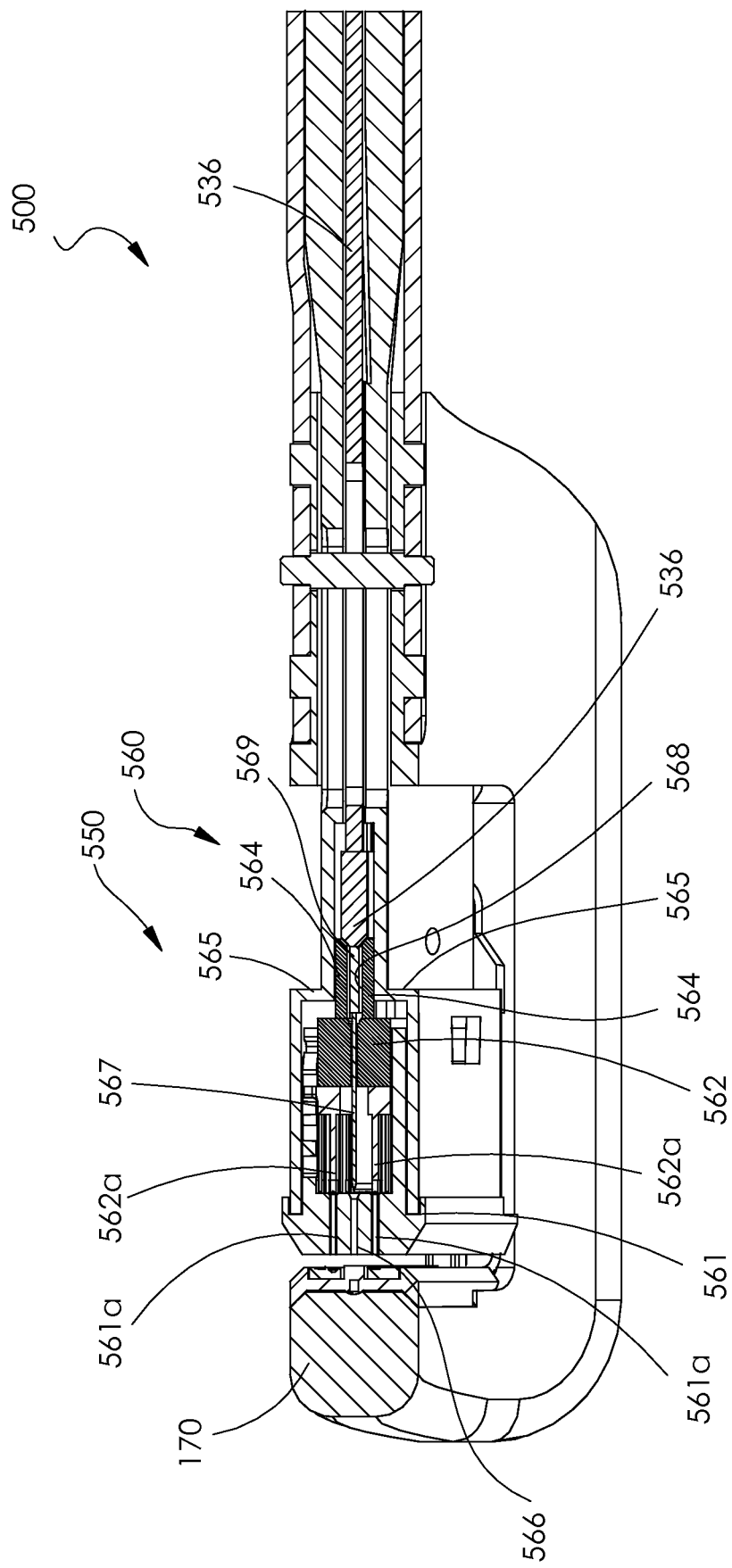
FIG. 18 is a cross-sectional view of an end effector of a surgical stapling instrument illustrated in a clamped, but unfired configuration.
Figure 19:
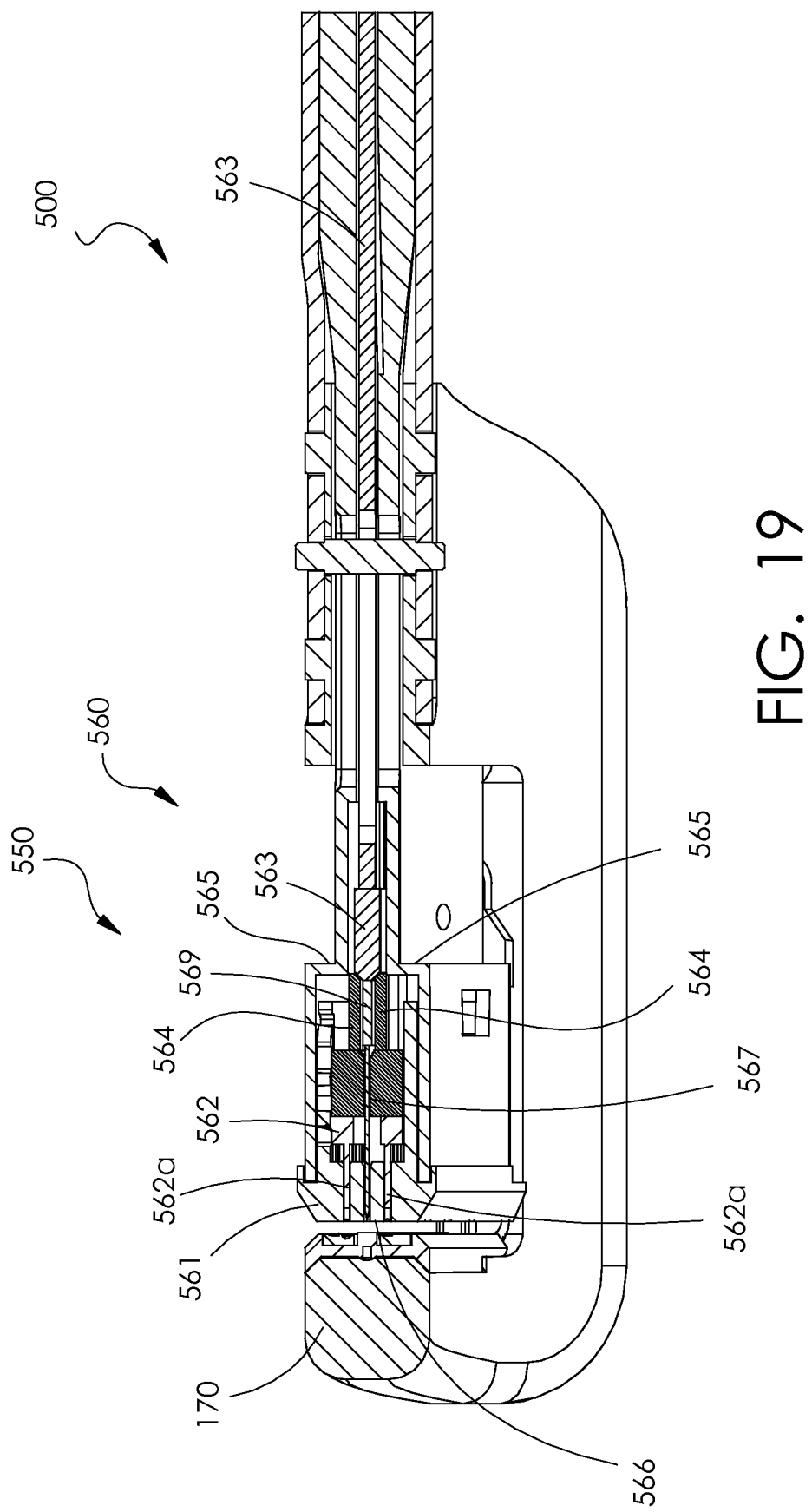
FIG. 19 is a cross-sectional view of the end effector of FIG. 18 illustrated in a staple firing mode.

A surgical stapling instrument 500 is illustrated in FIGS. 18-21. The instrument 500 is similar to the instrument 100, 200, 300, and/or 400 in many respects. The instrument 500 comprises an end effector 550 comprising a staple cartridge 560 and an anvil 170. The staple cartridge 560 comprises a cartridge body 561 including staple cavities 561a defined therein. Staples are removably stored in the staple cavities 561a. The staple cartridge 560 further comprises a staple driver 562 comprising pushers 562a which are configured to move the staples toward the anvil 170 and eject the staples from the staple cavities 561a. The instrument 500 further comprises a firing bar 536 configured to push the staple driver 562 distally toward the anvil 170. The staple driver 562 comprises proximally-extending flanges 564 which are engaged by the firing bar 536 as the firing bar 536 is advanced distally. When the end effector 550 is in an unclamped, but unfired, configuration as illustrated in FIG. 18, the flanges 564 are positioned within a channel 568 defined in the cartridge 561. In fact, the flanges 564 are flexed, or biased, inwardly by the sidewalls of the channel 568 and slide along the sidewalls as the staple driver 562 moves distally. The flanges 564 are engaged with and held in their inwardly-flexed position by the channel sidewalls throughout the firing stroke of the staples. The end of the staple firing stroke is depicted in FIG. 19.

Figure 20:
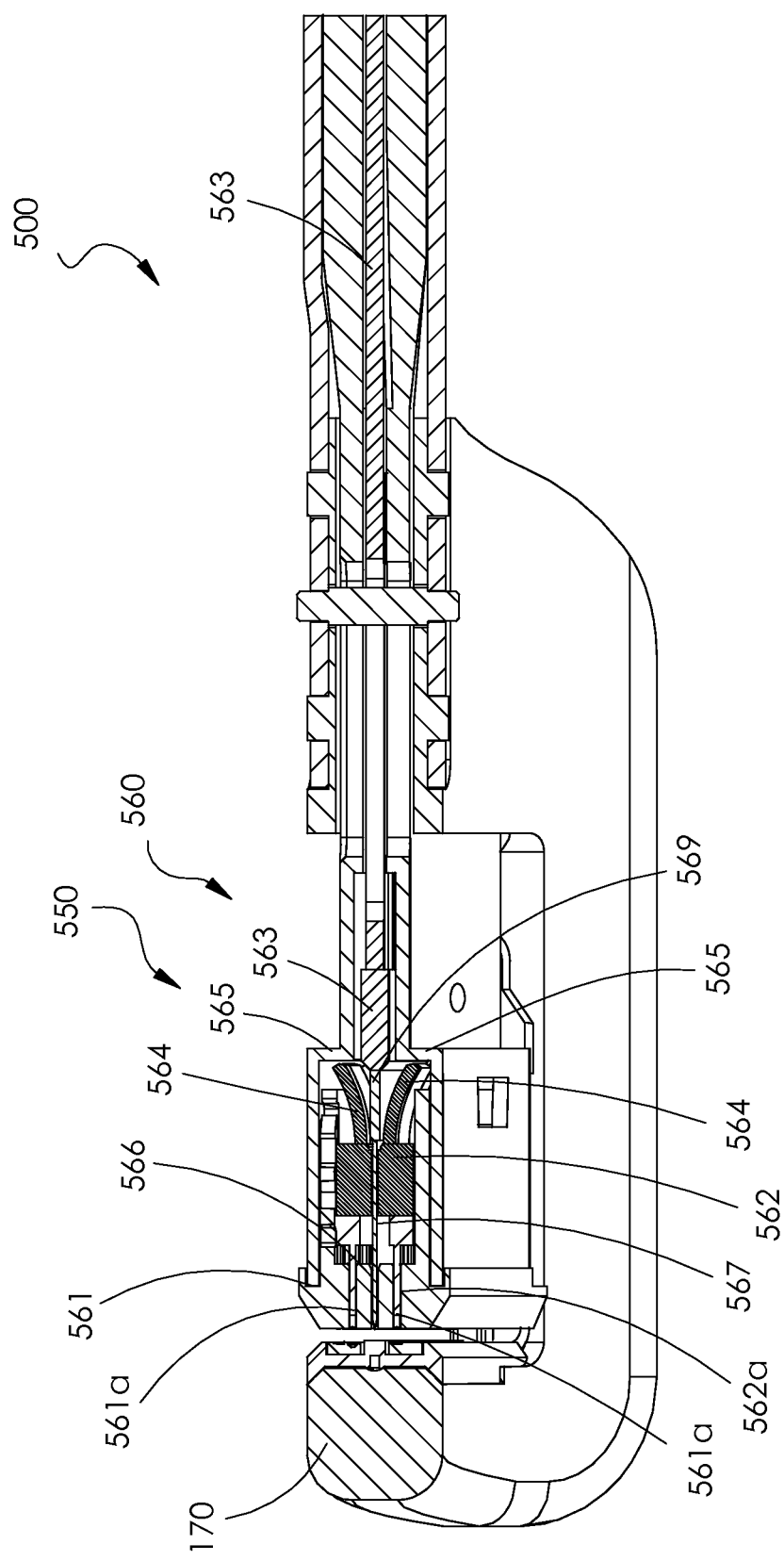
FIG. 20 is a cross-sectional view of the end effector of FIG. 18 illustrating a shift between its staple firing mode and a tissue cutting mode.
Figure 21:
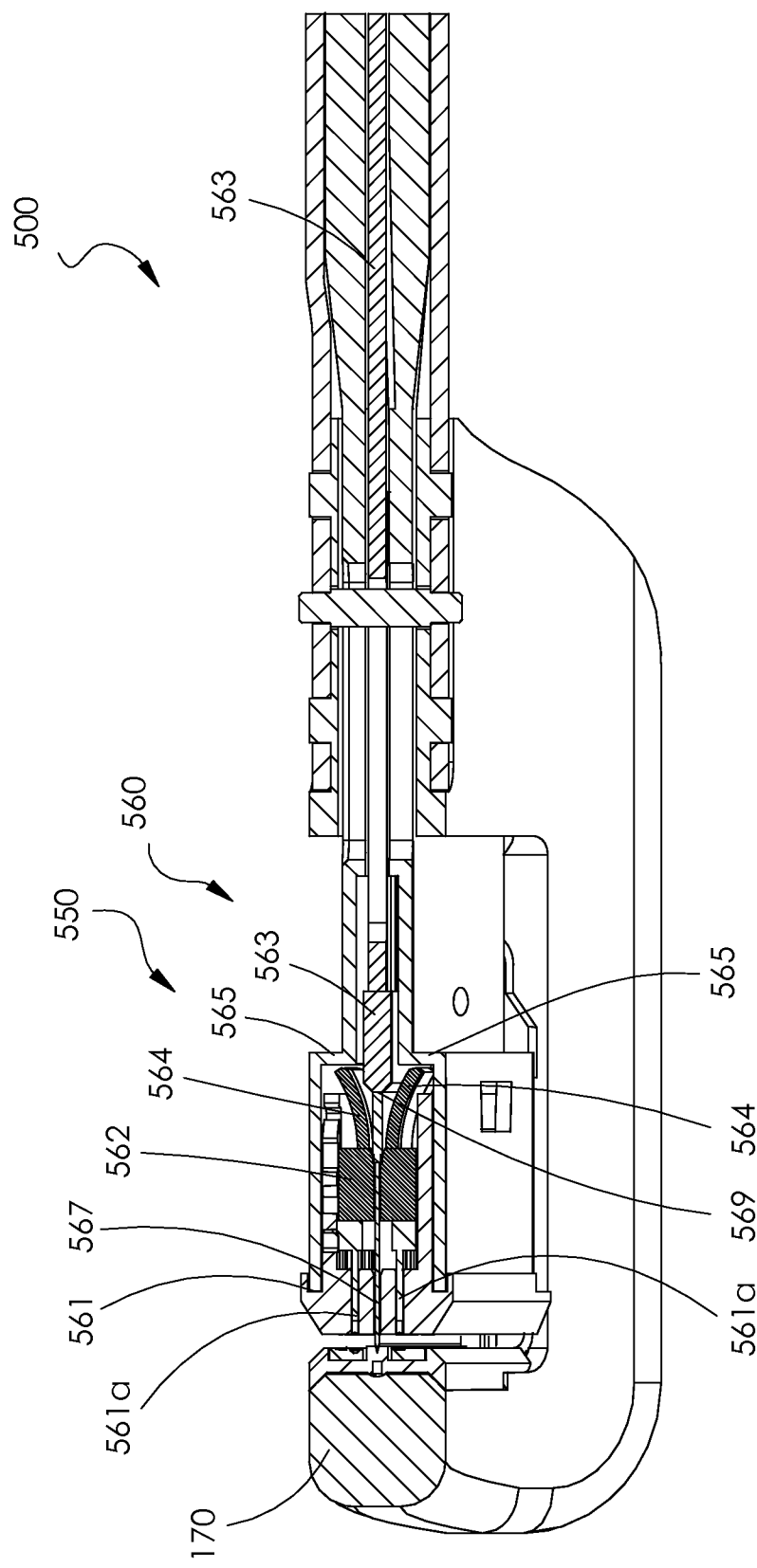
FIG. 21 is a cross-sectional view of the end effector of FIG. 18 illustrated in its tissue cutting mode.
Figure 22:
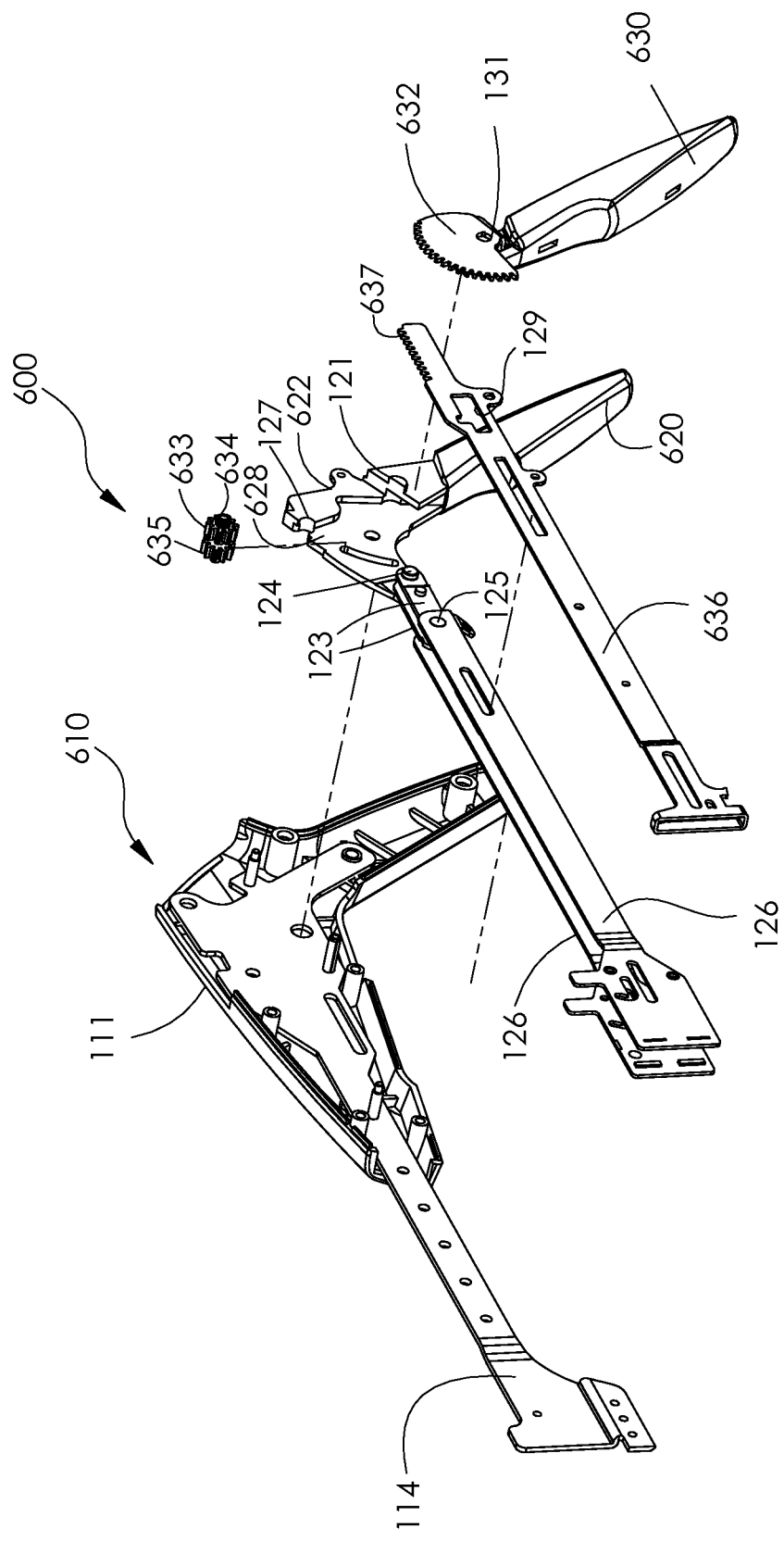
FIG. 22 is an exploded view of a surgical stapling instrument in accordance with at least one embodiment illustrated with components removed for the purpose of illustration.
Figure 24:
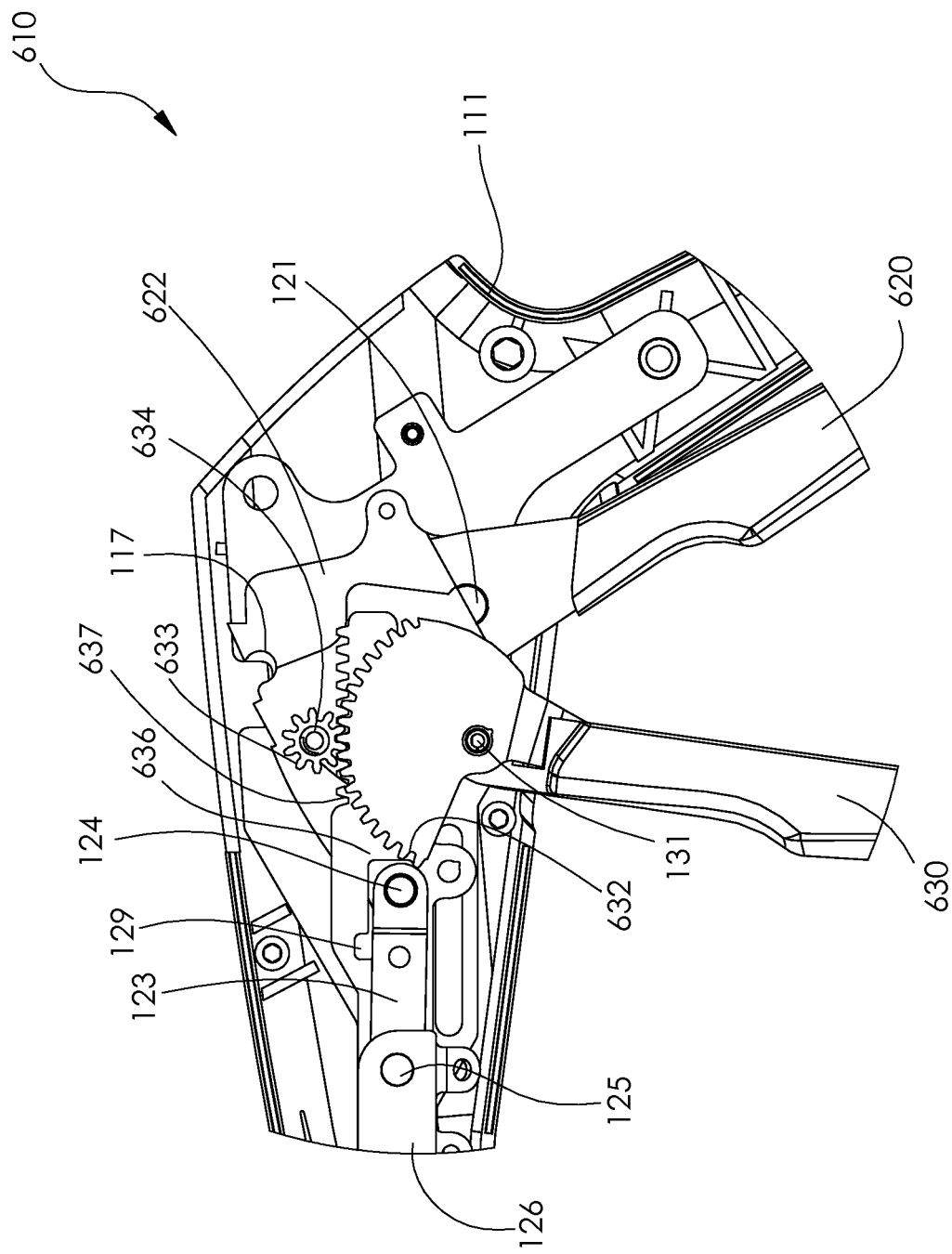
FIG. 24 is a partial cross-sectional view of the surgical stapling instrument of FIG. 22 illustrated in a clamped configuration prior to a firing stroke.

The staple cartridge 560 further comprises a cutting member 567 movably positioned in a knife slot 566 defined in the cartridge body 561. The cutting member 567 comprises a base 569 which is gripped between the flanges 564 such that, as the staple driver 562 is driven distally by the firing bar 563, the cutting member 567 moves with the staple driver 562. Referring again to FIG. 19 which depicts the end of the staple firing stroke, it should be appreciated that the cutting member 567 has not yet emerged from the cartridge body 561. Thus, the staple firing operation of the instrument 500 is separate and distinct from the tissue incising operation of the instrument 500. The instrument 500 transitions between its staple firing operation and its tissue incising operation when the flanges 564 release the cutting member 567. Upon comparing FIGS. 19 and 20, is should be appreciated that the flanges 564 spring outwardly when the proximal ends of the flanges 564 are no longer biased inwardly by the sidewalls of the channel 568. More specially, the flanges 564 flex outwardly once they clear the distal end 565 of the channel 568. At such point, the flanges 564 are no longer engaged with the cutting member 567. Moreover, at such point, the flanges 564 are no longer engaged with the firing bar 536 and, as a result, the firing bar 536 can no longer push the staple driver 562 distally. Instead, the firing bar 536 can come into direct contact with the base 569 of the cutting member 567 and advance the cutting member 567 distally when the firing bar 536 is advanced distally, as illustrated in FIG. 21, to transect the tissue captured between the anvil 170 and the staple cartridge 560.

Further to the above, the point in which the instrument 500 shifts between a staple-firing operating mode and a tissue-cutting operating mode is a function of the distance in which the firing bar 536 has moved. Other instruments disclosed herein shift between a staple-firing operating mode and a tissue-cutting operating mode as a function of the force transmitted through a firing bar of the instrument, for example. Certain embodiments could employ a combination of both shifting approaches.

Figure 25:
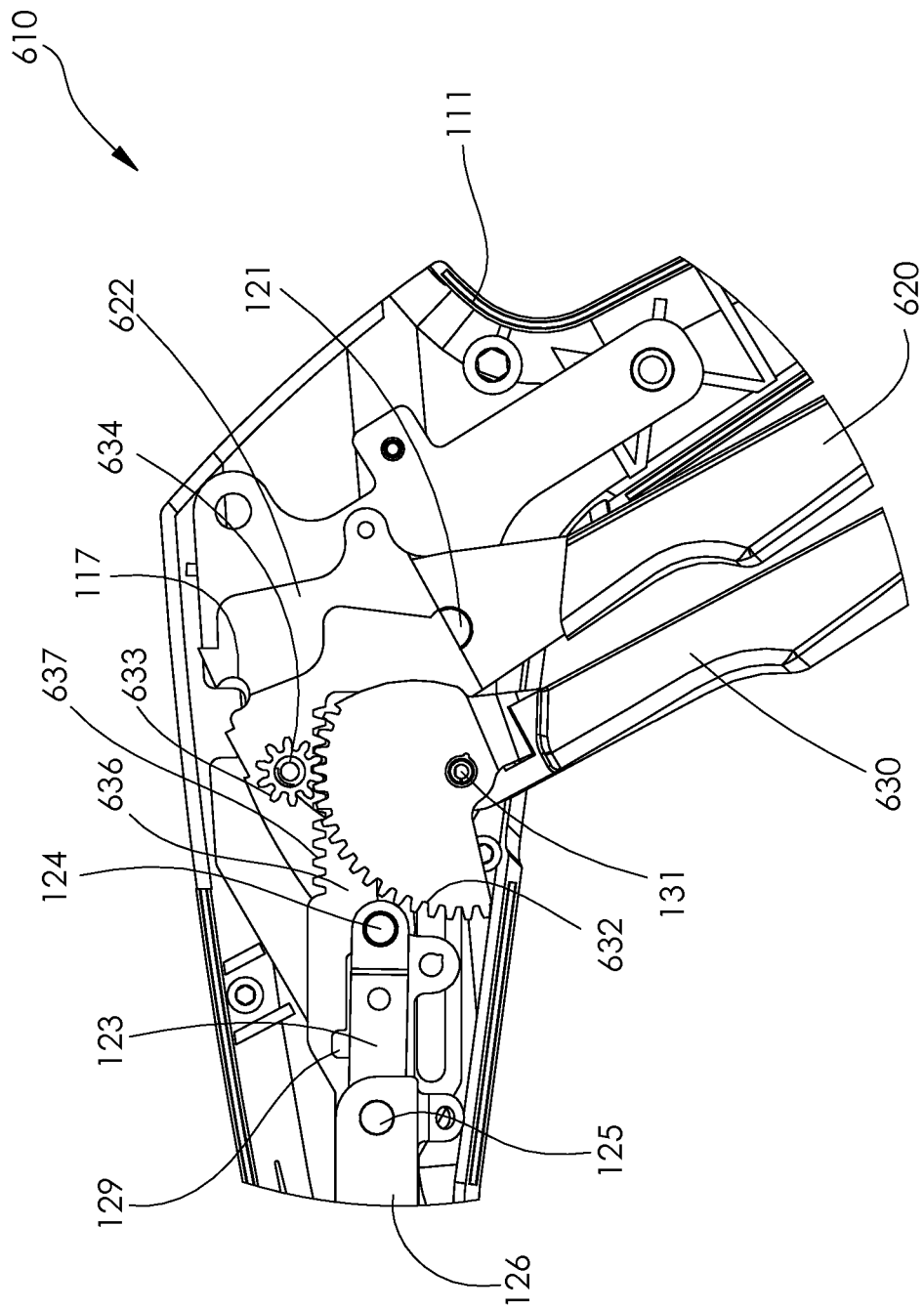
FIG. 25 is a partial cross-sectional view of the surgical stapling instrument of FIG. 22 illustrated in a clamped configuration after the firing stroke.

A surgical stapling instrument 600 is illustrated in FIGS. 22-28A. The instrument 600 is similar to the instruments 100, 200, 300, 400, 500 and/or the other surgical instruments disclosed herein in many respects. The instrument 600 comprises a handle 610 which includes a closure trigger 620 configured to operate a closure, or tissue clamping, system and a firing trigger 630 configured to operate a firing system. The closure trigger 620 is rotatable between an unactuated position (FIG. 24) and an actuated position (FIG. 25). The closure system of the instrument 600 is similar to the closure system of the instrument 100 in many respects and is not repeated herein for the sake of brevity. In various instances, the instrument 600 includes a lockout system which prevents the actuation of the firing trigger 630 prior to the actuation of the closure trigger 620.

Further to the above, the closure trigger 620 comprises a drive portion 622 which pushes the links 123 distally to clamp the end effector of the surgical instrument 600 onto tissue. The drive portion 622 comprises a clearance slot 628 defined therein such that the drive portion 622 can move relative to a shaft 634 which extends through the clearance slot 628.

The firing system of the instrument 600 is separate and distinct from the closure system. The firing system has two separate and distinct operating functions, i.e., a staple firing function and a tissue incising function. The staple firing function occurs during a first actuation of the firing trigger 630 and the tissue incising function occurs during a second actuation of the firing trigger 630. Similar to the above, the firing trigger 630 is rotatably coupled to the housing 111 about a pivot 131. Referring primarily to FIGS. 23, 23A, 28, and 28A, the firing trigger 630 comprises a gear portion 632 which is meshingly engaged with a pinion gear 633. The pinion gear 633 is mounted to the shaft 634 which is rotatably mounted to the handle housing 111. More specifically, the pinion gear 633 is mounted to a first portion 634a of the shaft 634 such that the pinion gear 633 and the shaft portion 634a rotate together. Thus, the actuation, or rotation, of the firing trigger 630 rotates the pinion gear 633 and the first shaft portion 634a.

Referring again to FIGS. 28 and 28A, the shaft 634 further comprises a second portion 634b which is selectively engageable with the first portion 634a at a ratchet interface 639. When the second shaft portion 634b is operably engaged with the first portion 634a, the rotation of the first portion 634a is transferred to the second portion 634b and the first and second shaft portions 634a, 634b rotate together. An output pinion gear 635 is mounted to the second shaft portion 634b such that the pinion gear 635 rotates with the second shaft portion 634b. The pinion gear 635 is meshingly engaged with a rack 637 defined on the proximal end of a firing bar 636. In use, referring now to FIG. 25, the ratchet interface 639 is configured to transfer the rotational motion of the firing trigger 630 to the firing bar 636 and drive the firing bar 636 distally (direction D in FIG. 28) when the firing trigger 630 is actuated.

Figure 26:
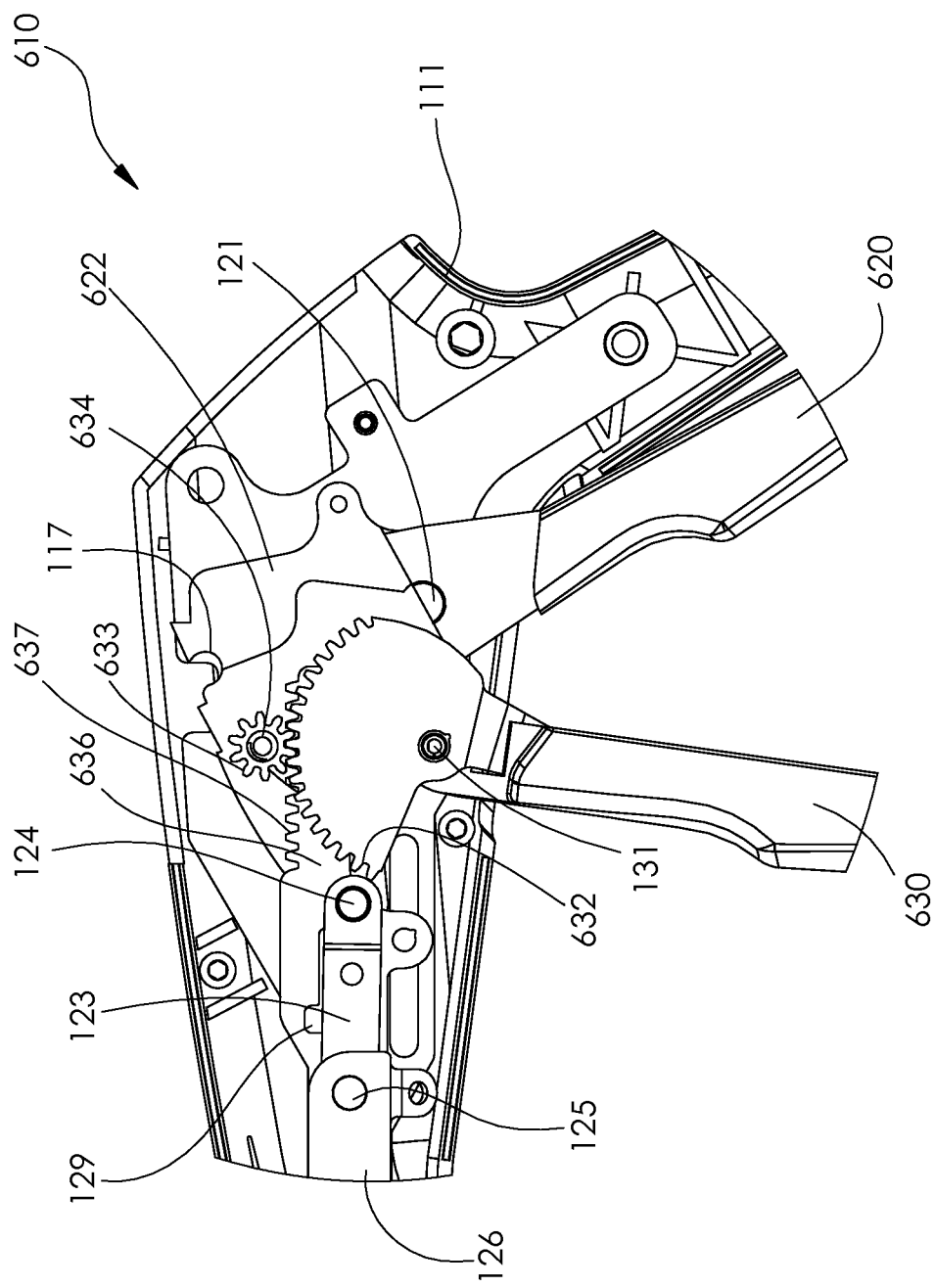
FIG. 26 is a partial cross-sectional view of the surgical stapling instrument of FIG. 22 illustrated in a clamped, fired configuration prior to a transection stroke.

Further to the above, referring again to FIG. 25, a first actuation of the firing trigger 630 pushes the firing bar 636 distally to fire the staples. After the first actuation, the surgeon can release the firing trigger 630 and allow a return spring operably coupled with the firing trigger 630 to return the firing trigger 630 back to its unfired position, as illustrated in FIG. 26. Alternatively, the surgeon can manually return the firing trigger 630 back to its unactuated position. In either event, the ratchet interface 639 is configured to permit the first shaft portion 634a to rotate relative to the second shaft portion 634b when the firing trigger 630 is returned to its unfired position. More specifically, the first shaft portion 634a comprises ratchet teeth which slide relative to corresponding ratchet teeth defined on the second shaft portion 634b when the firing trigger 630 is returned to its unactuated position. In order to accommodate such relative movement, the first shaft portion 634a is permitted to displace away from the second shaft portion 634b. The handle 610 further comprises a biasing member, such as a spring, for example, configured to re-engage the first shaft portion 634a with the second shaft portion 634b once the firing trigger 630 has been returned to its unactuated position.

Figure 27:
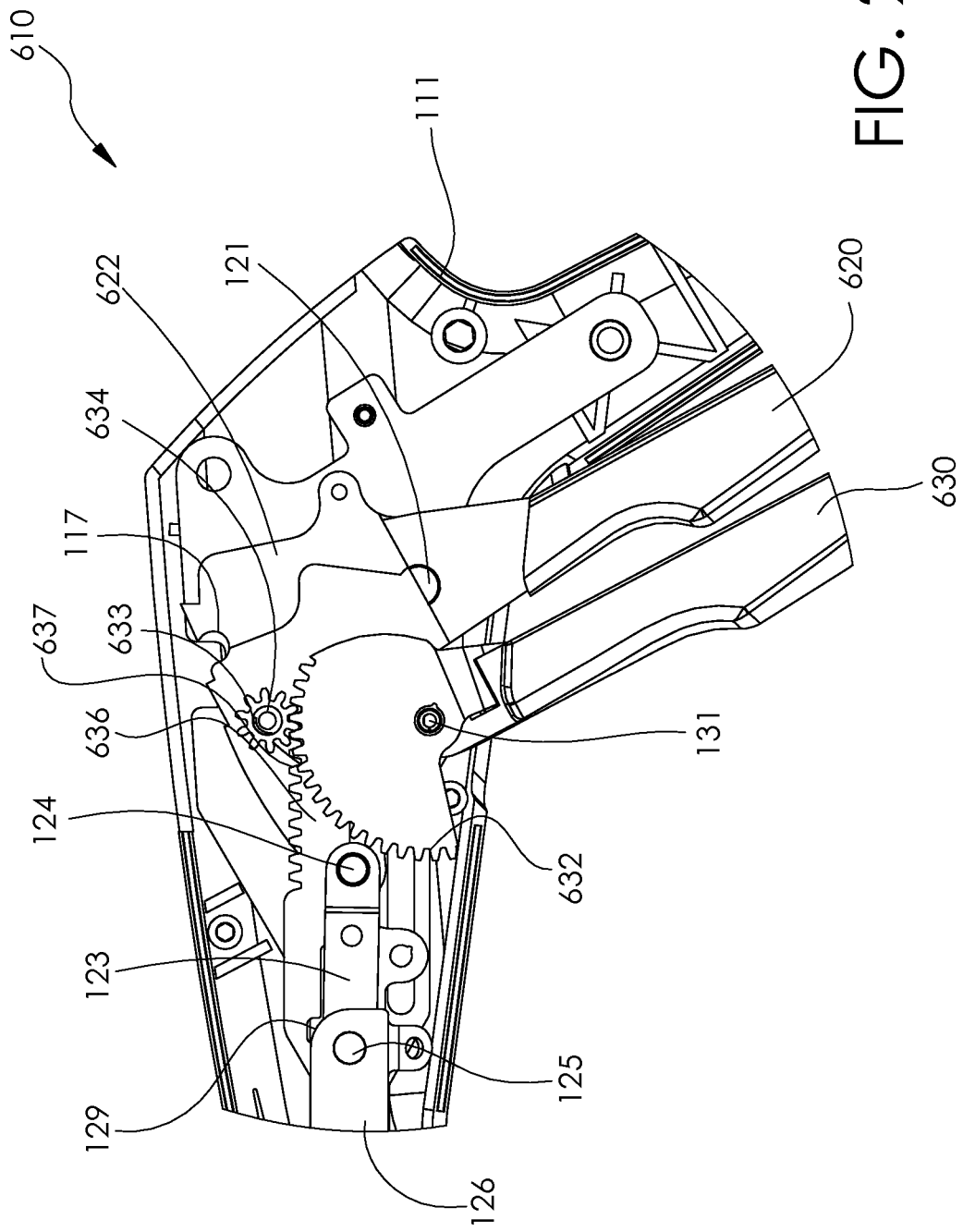
FIG. 27 is a partial cross-sectional view of the surgical stapling instrument of FIG. 22 illustrated in a clamped, fired configuration after the transection stroke.
Figure 28A:
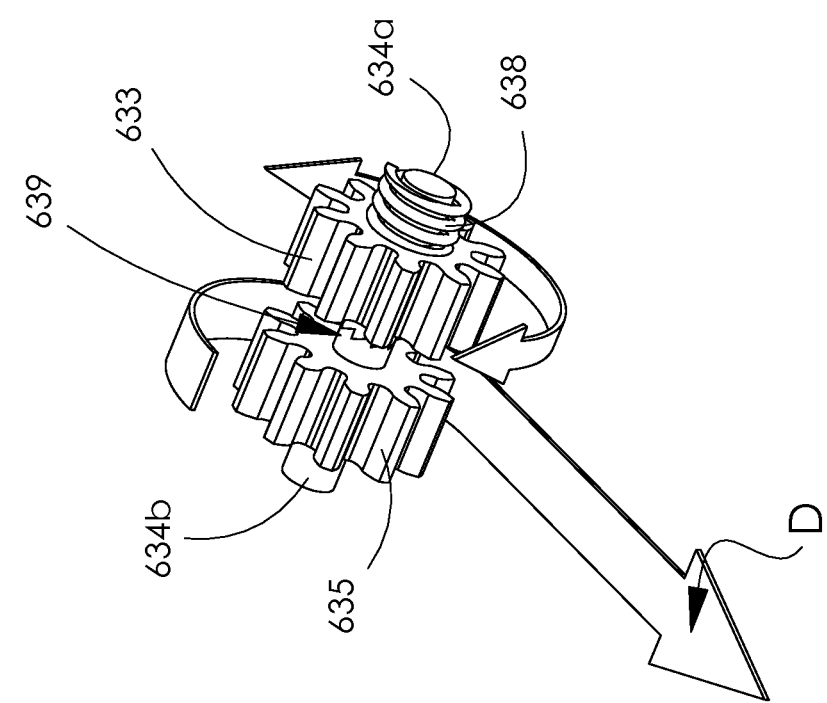
FIG. 28A is another perspective view of the transmission of FIG. 28.
Figure 28:
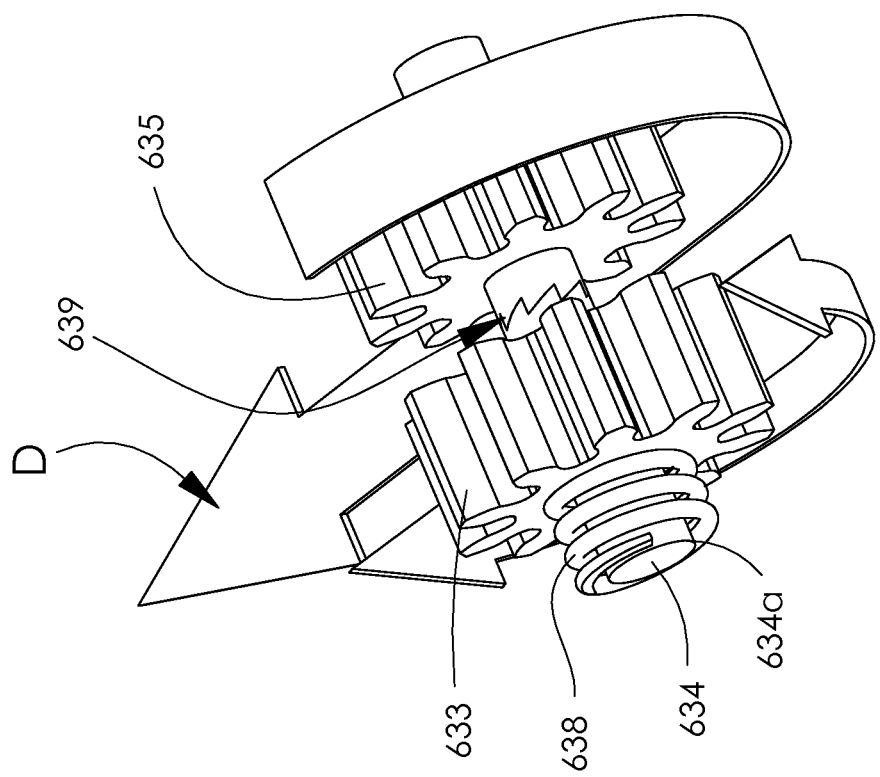
FIG. 28 is a perspective view of a transmission of the surgical stapling instrument of FIG. 22.
Figure 29:
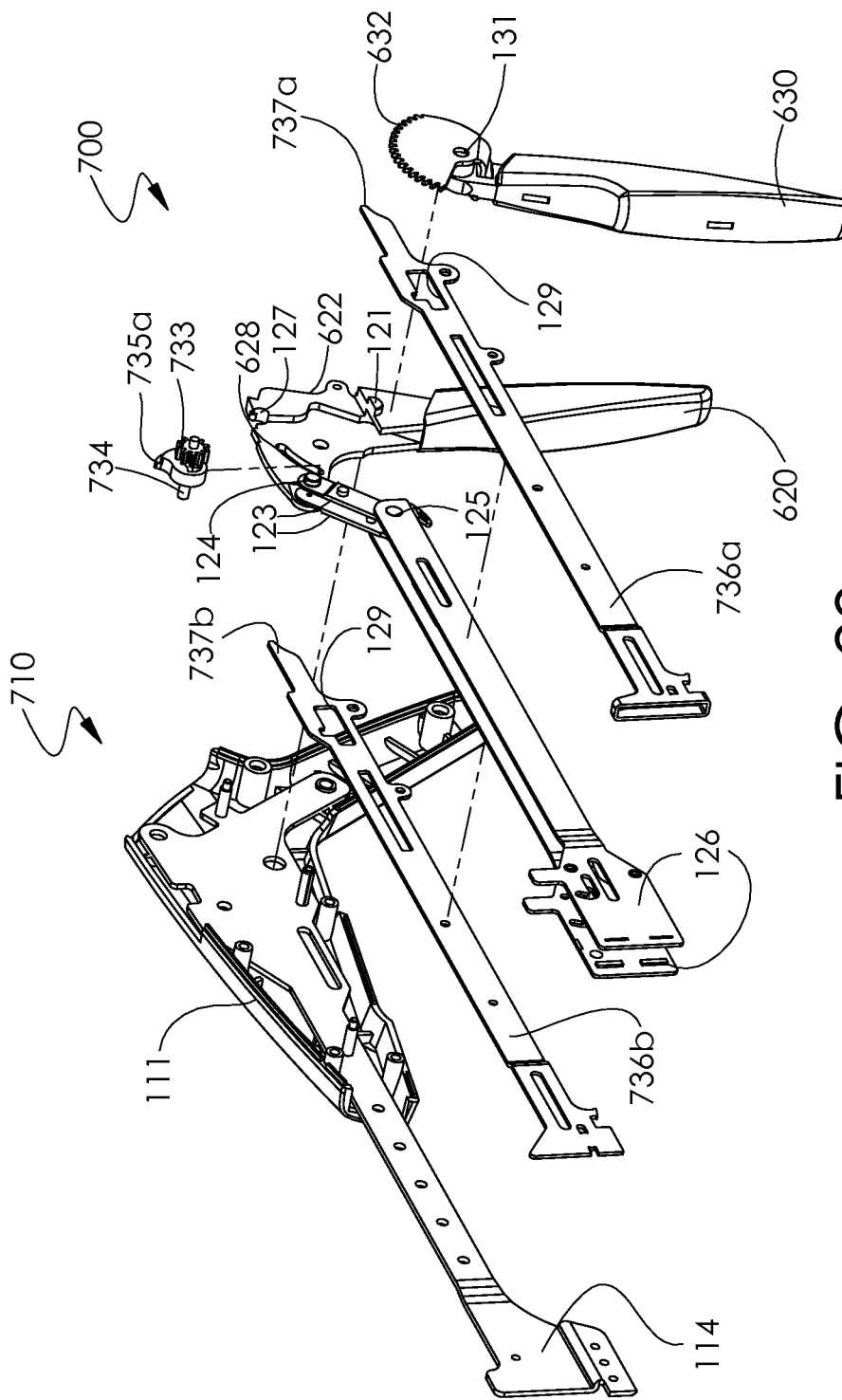
FIG. 29 is an exploded view of a surgical stapling instrument in accordance with at least one embodiment illustrated with components removed for the purpose of illustration.
Figure 30:
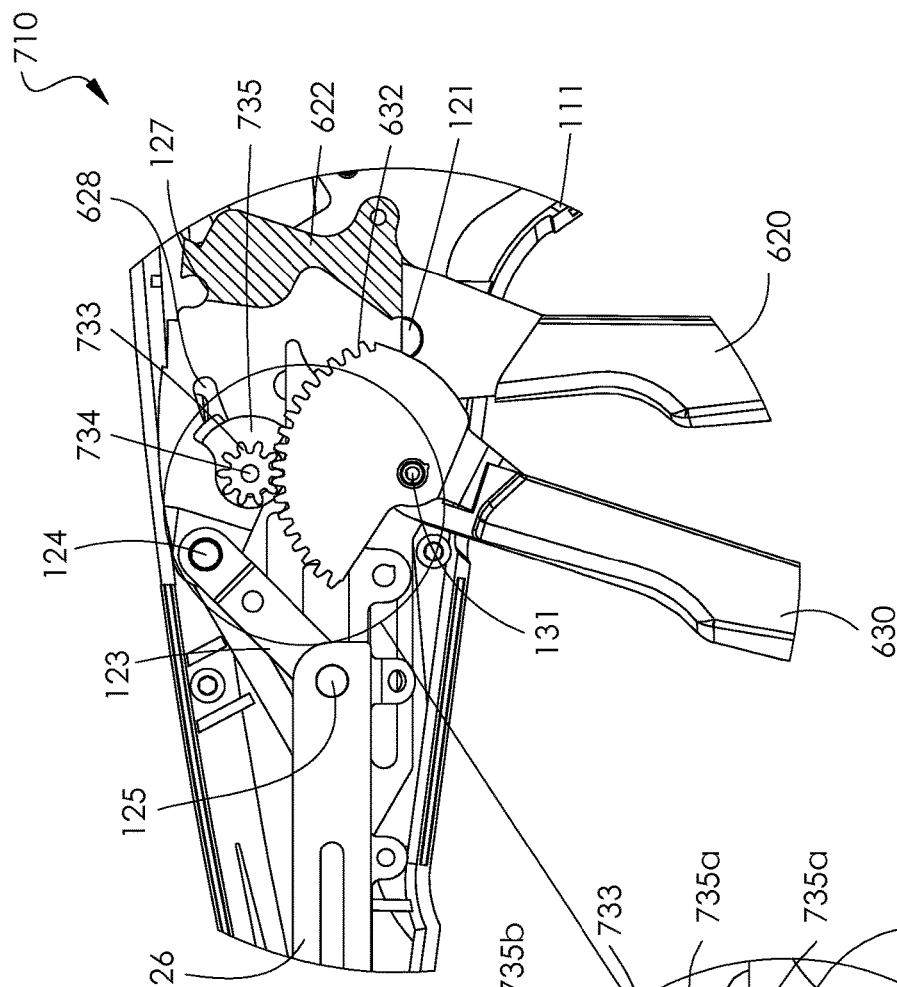
FIG. 30 is a partial cross-sectional view of the surgical stapling instrument of FIG. 29 illustrated in an unclamped, unfired configuration.
Figure 30A:
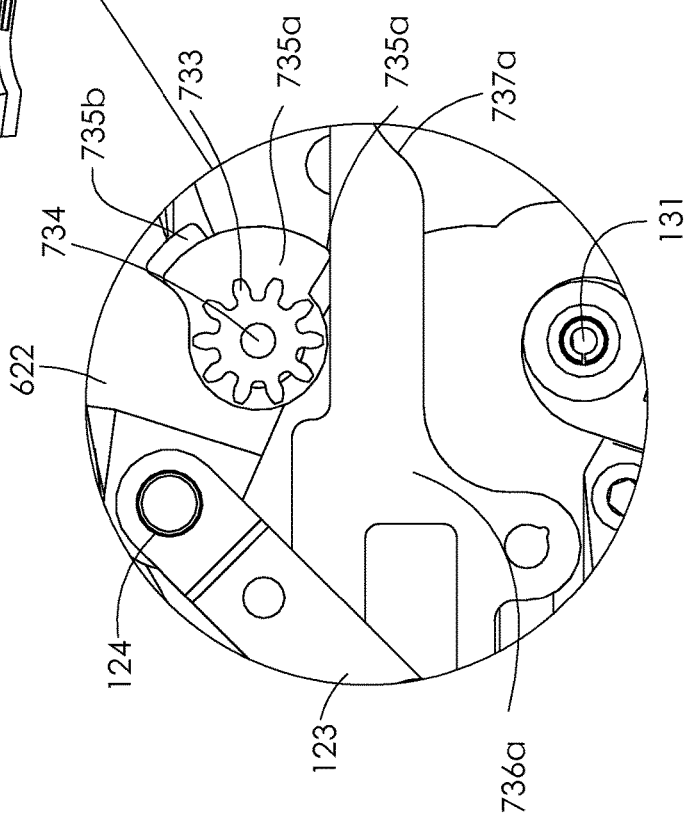
FIG. 30A is a detail view of a transmission of the surgical stapling instrument of FIG. 29 illustrated in a configuration which corresponds to the unclamped, unfired configuration depicted in FIG. 30.

Referring again to FIG. 26, the reader should appreciate that the firing bar 636 has been only partially advanced during the first stroke of the firing trigger 630. Such partial advancement of the firing bar 630 during the first stroke of the firing trigger 630 fires, or completely forms, the staples stored within the end effector of the instrument 600, but it does not transect the tissue captured within the end effector. Referring now to FIG. 27, the firing trigger 630 can be actuated a second time to fully advance the firing bar 630 and transect the tissue. As outlined above, the actuation, or rotation, of the firing trigger 630 drives the pinion gear 633, the shaft 634, and the output pinion gear 635 to advance the firing bar 636 distally. In various instances, the surgeon may opt to not transect the tissue and may instead to unclamp the tissue after firing the staples. In such instances, the surgeon would not actuate the firing trigger 630 a second time. In various instances, the teachings described above in connection with the instrument 600 can be used in connection with the instruments 400 and/or 500, for example.

Figure 31:
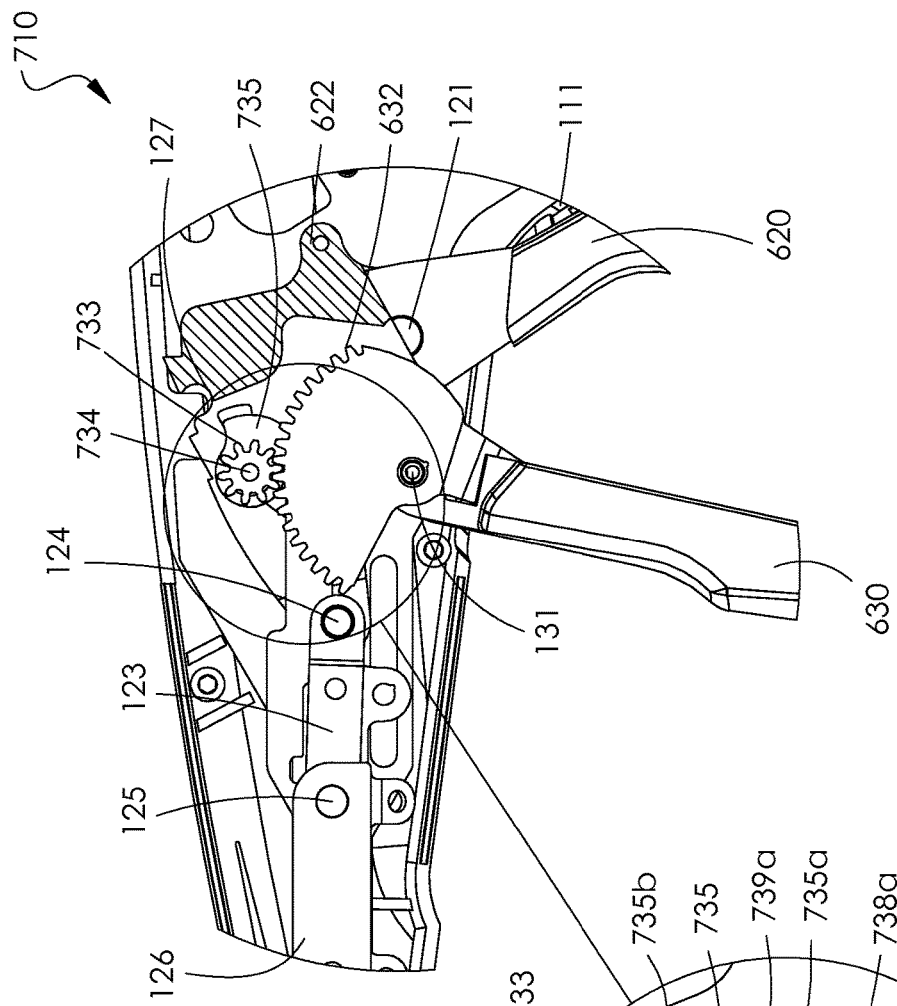
FIG. 31 is a partial cross-sectional view of the surgical stapling instrument of FIG. 29 illustrated in a clamped, unfired configuration.
Figure 31A:
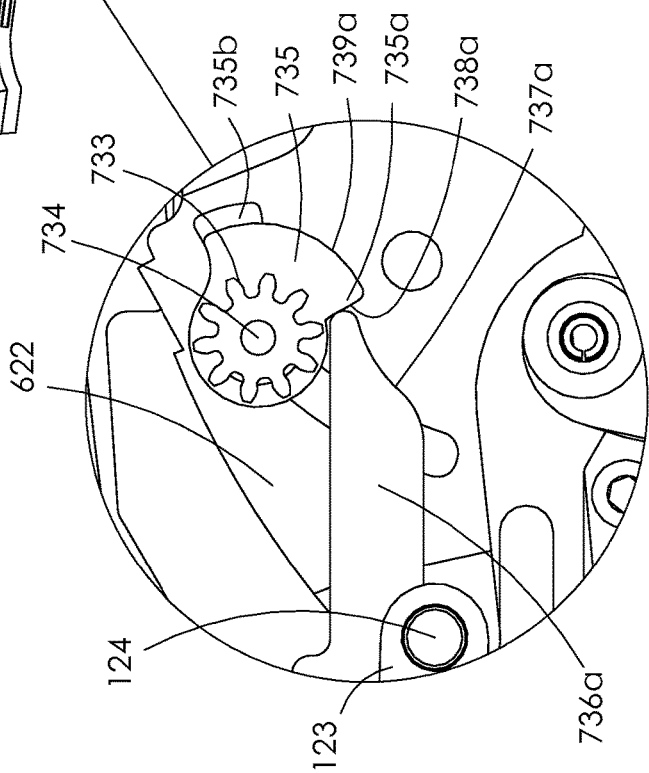
FIG. 31A is a detail view of the transmission of the surgical stapling instrument of FIG. 29 illustrated in a configuration which corresponds to the clamped, unfired configuration depicted in FIG. 31.

A surgical stapling instrument 700 is illustrated in FIGS. 29-33A. The instrument 700 is similar to the instrument 100, 200, 300, 400, 500, 600, and/or the other surgical instruments disclosed herein in many respects. The instrument 700 comprises a handle 710 which includes a closure trigger 620 configured to operate a closure, or tissue clamping, system and a firing trigger 630 configured to operate a firing system. The closure trigger 620 is rotatable between an unactuated position (FIG. 30) and an actuated position (FIG. 31). The closure system of the instrument 700 is similar to the closure system of the instrument 100 in many respects and is not repeated herein for the sake of brevity. In various instances, the instrument 700 includes a lockout system which prevents the actuation of the firing trigger 630 prior to the actuation of the closure trigger 620.

The firing system of the instrument 700 is separate and distinct from the closure system. The firing system has two separate and distinct operating functions, i.e., a staple firing function and a tissue incising function. As described in greater detail further below, an actuation of the firing trigger 630 performs both functions. The firing trigger 630 is rotatably mounted to the handle 710 about a pivot 131 and includes a gear portion 632. The teeth of the gear portion 632 are meshingly engaged with a pinion gear 733 which is rotatably mounted in the handle 710 about a shaft 734. The shaft 734 further comprises two cam lobes, i.e., a first cam lobe 735a and a second cam lobe 735b, mounted thereto. The first cam lobe 735a is configured to engage and advance a staple firing bar 736a and the second cam lobe 735b is configured to engage and advance a tissue cutting bar 736b. The cam lobes 735a, 735b are mounted to the shaft 734 such that they rotate with the shaft 734.

Prior to the firing trigger 630 being actuated, referring to FIG. 31, the first cam lobe 735a is aligned with a first cam surface 737a defined on the proximal end of the staple firing bar 736a and the second cam lobe 735b is aligned with a second cam surface 737b defined on the proximal end of the tissue cutting bar 736b. The first cam lobe 735a and the second cam lobe 735b are mounted to the shaft 734 in a staggered relationship. When the firing trigger 630 is in its unactuated position, as illustrated in FIG. 31, the first cam lobe 735a is positioned adjacent to the first cam surface 737a and the second cam lobe 735b is spaced apart from the second cam surface 737b.

Figure 32:
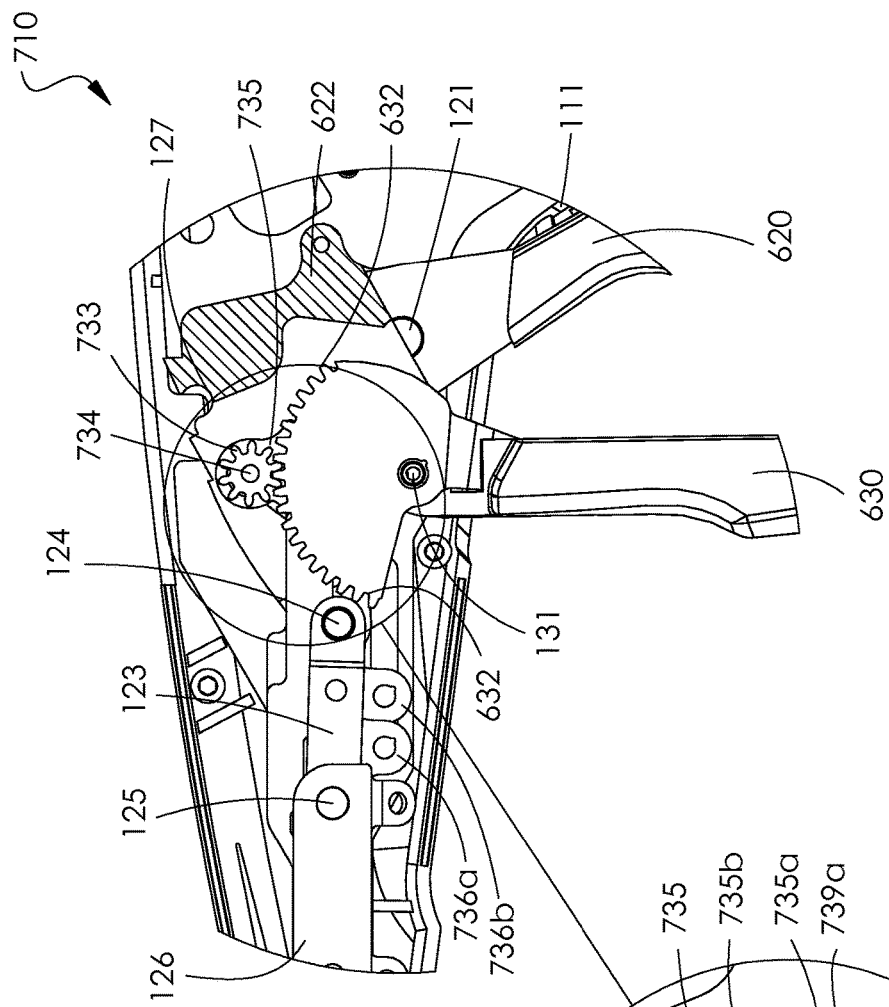
FIG. 32 is a partial cross-sectional view of the surgical stapling instrument of FIG. 29 illustrated in a clamped configuration in which staples are being deployed from the surgical instrument.
Figure 32A:
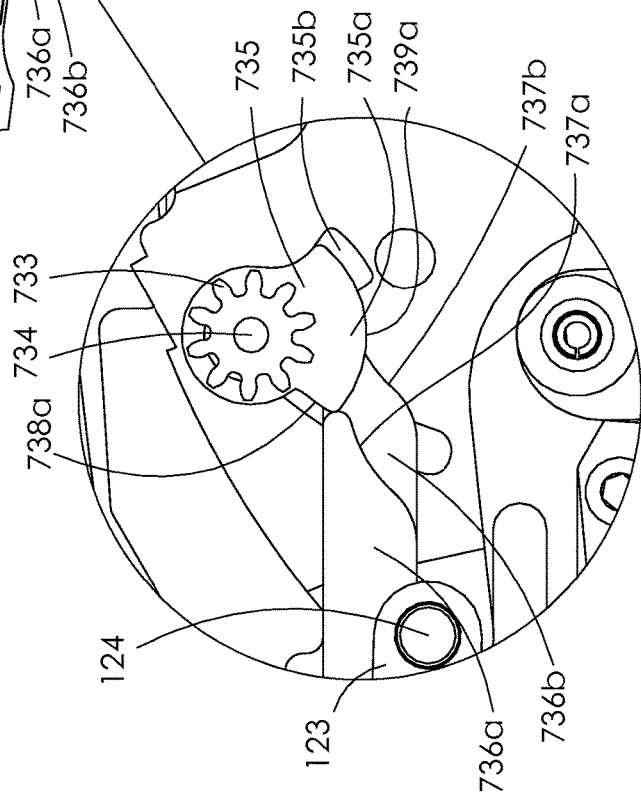
FIG. 32A is a detail view of the transmission of the surgical stapling instrument of FIG. 29 illustrated in a configuration which corresponds to the clamped, fired configuration depicted in FIG. 32.
Figure 34:
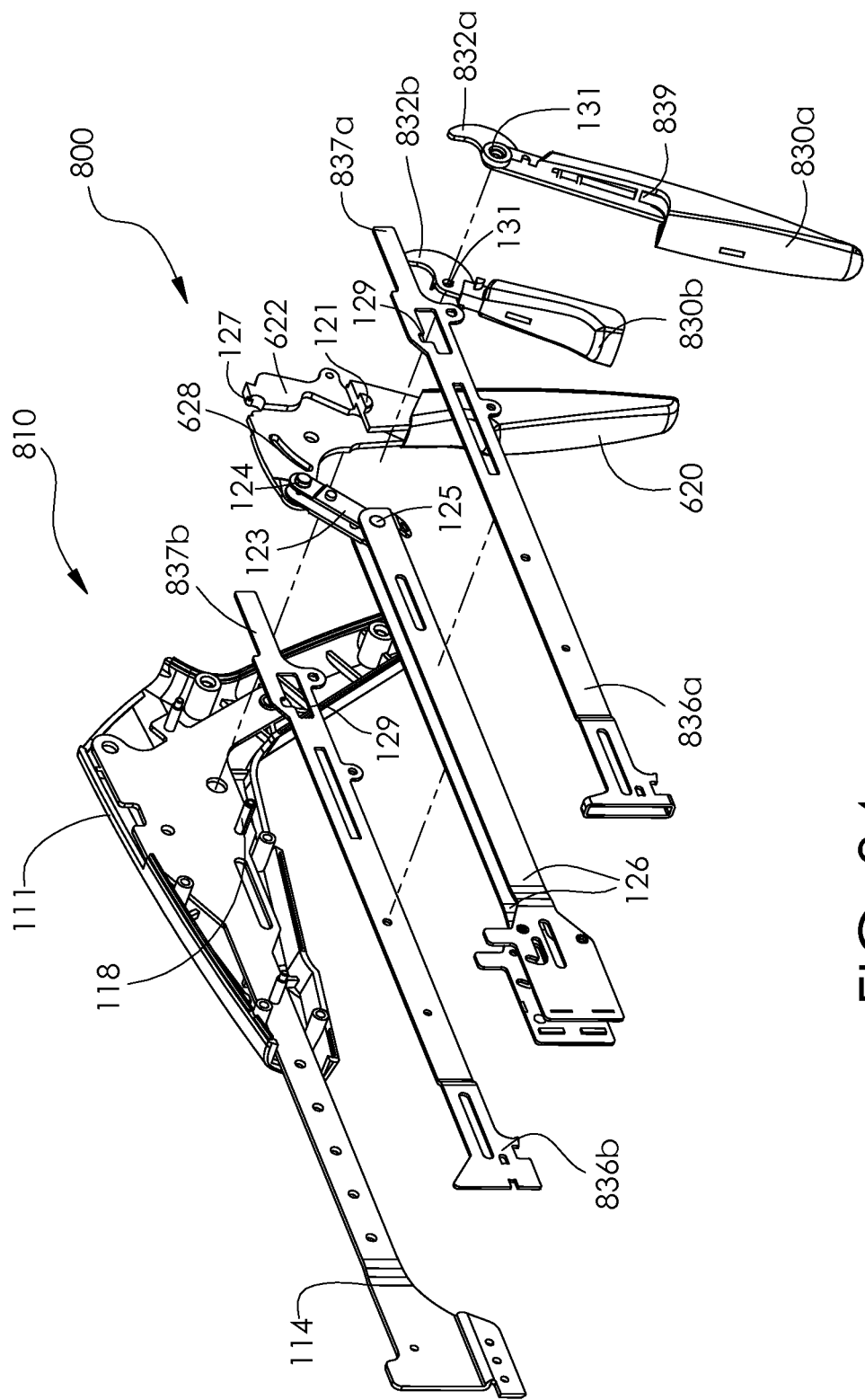
FIG. 34 is an exploded view of a surgical stapling instrument in accordance with at least one embodiment illustrated with components removed for the purpose of illustration.
Figure 35:
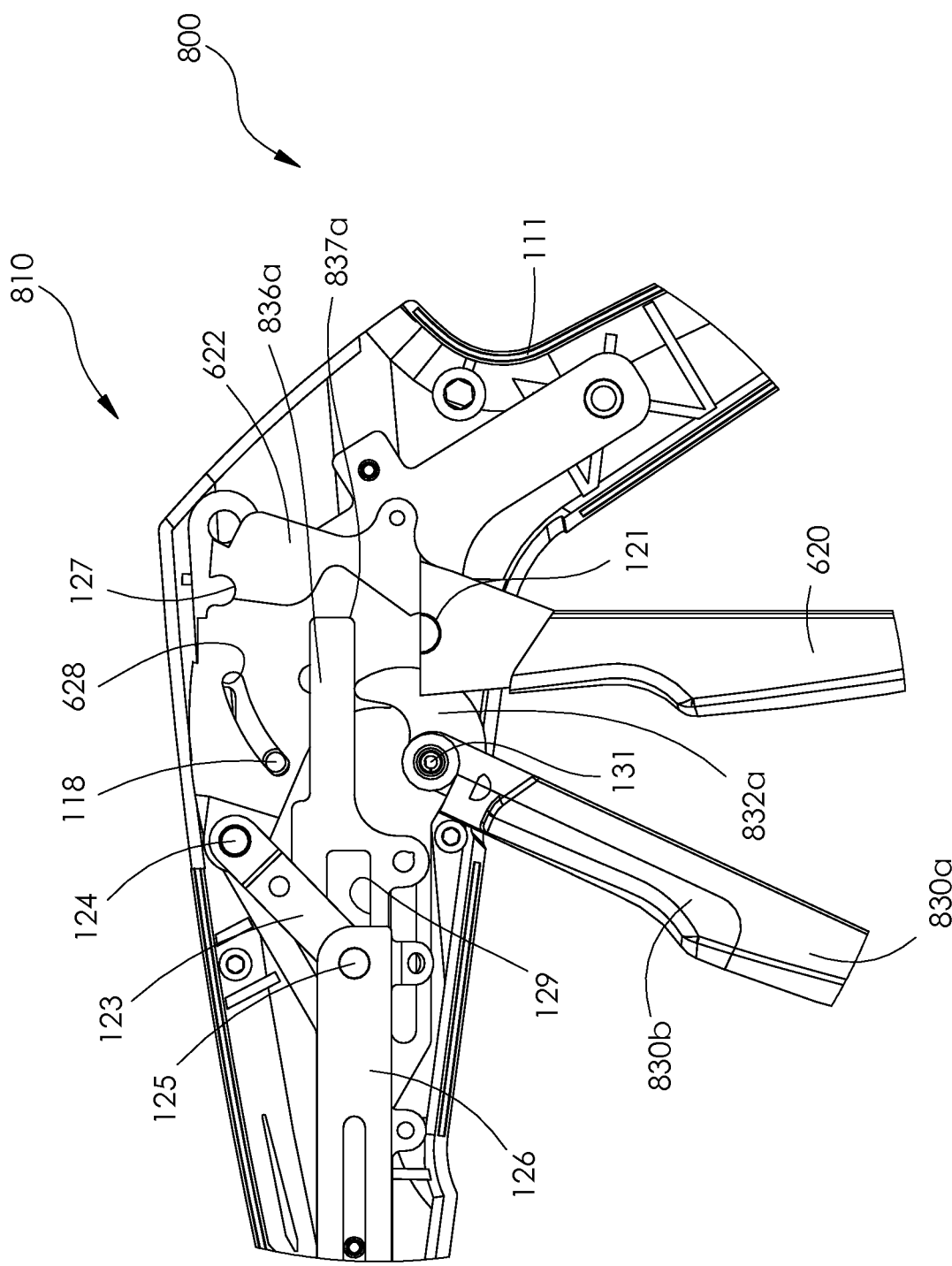
FIG. 35 is a partial cross-sectional view of the surgical stapling instrument of FIG. 34 in an unclamped, unfired configuration.

Further to the above, the firing trigger 630 is actuated to drive the staple firing bar 736a and the tissue cutting bar 736b during a single stroke of the firing trigger 630. A first portion of the firing trigger actuation drives the staple firing bar 736a distally and a second portion of the firing trigger actuation drives the tissue cutting bar 736b distally. The first portion does not overlap with the second portion of the firing trigger actuation. Stated another way, the staple firing process has been completed before the tissue cutting process begins. In use, a ramp 738a of the first cam lobe 735a displaces the staple firing bar 736a distally until the ramp 738a passes by the first cam surface 737a. At such point, a dwell 739a of the first cam lobe 735a is aligned with the first cam surface 737a and the staple firing bar 736a is no longer advanced distally by the first cam lobe 735a. In various other embodiments, the dwell 739a of the first cam lobe 735a can complete the staple-forming process. In such instances, the ramp 738a of the first cam lobe 735a initiates the staple forming process and the dwell 739a finishes the staple forming process. In at least one instance, the ramp 738a can complete more of the staple forming process than the dwell 739a. In such instances, the staples quickly grasp the tissue and are then slowly closed to fully secure the tissue therein. Alternatively, the dwell 739a can complete more of the staple forming process than the ramp 738a. In such instances, the squeezing pressure applied by the staples may be applied over a longer period of time which can better permit fluids to flow out of the tissue during the staple forming process. In either event, the second cam lobe 735b is spaced apart from the ramp 738a by the dwell 739a. As the shaft 734 is rotated by the firing actuator 630, as illustrated in FIGS. 32 and 32A, the second cam lobe 735b is rotated into contact with the second cam surface 737b and the staple cutting process is completed, as illustrated in FIGS. 33 and 33A.

In various instances, further to the above, the instrument 700 can include a stop which demarcates the transition between the staple firing process and the tissue cutting process. The stop can impede or arrest the movement of the firing actuator 630 after the staple firing bar 736a has been fully advanced and prior to the tissue cutting bar 736b being advanced, for example. The handle 710 can include a stop release which, once actuated, can permit the surgeon to complete the firing stroke of the firing actuator 630. Such an embodiment can permit a surgeon to elect whether to proceed with the tissue cutting function of the instrument 700. In certain instances, the instrument 700 can generate haptic feedback, such as audible and/or tactile feedback, for example, as the firing actuator 630 passes through the transition between the staple firing function and the tissue cutting function.

In various alternative embodiments, further to the above, the tissue cutting process can at least partially overlap the staple forming process. In such embodiments, the first cam lobe 735a and the second cam lobe 735b are positioned and arranged on the shaft 734 such that the first cam lobe 735a can drive the staple firing bar 736a at the same time that the second cam lobe 735b drives the tissue cutting bar 736b.

Further to the above, the firing actuator 630 can be returned to its unactuated position after it has been actuated to fire the staples and/or incise the tissue. The handle 710 can comprise a return spring engaged with the firing actuator 630 which is biased to return the firing actuator 630 to its unactuated position. In addition to or in lieu of the above, the instrument 700 can include one or more biasing members engaged with the bars 736a, 736b which are configured to return the bars 736a, 736b to their unfired position. As the firing actuator 630 is returned to its unactuated position, the gear portion 632 rotates the pinion gear 733, the shaft 734, and the cam lobes 735a, 735b in an opposite direction to disengage the cam lobes 735a, 735b from the bars 736a, 736b, respectively.

Figure 36:
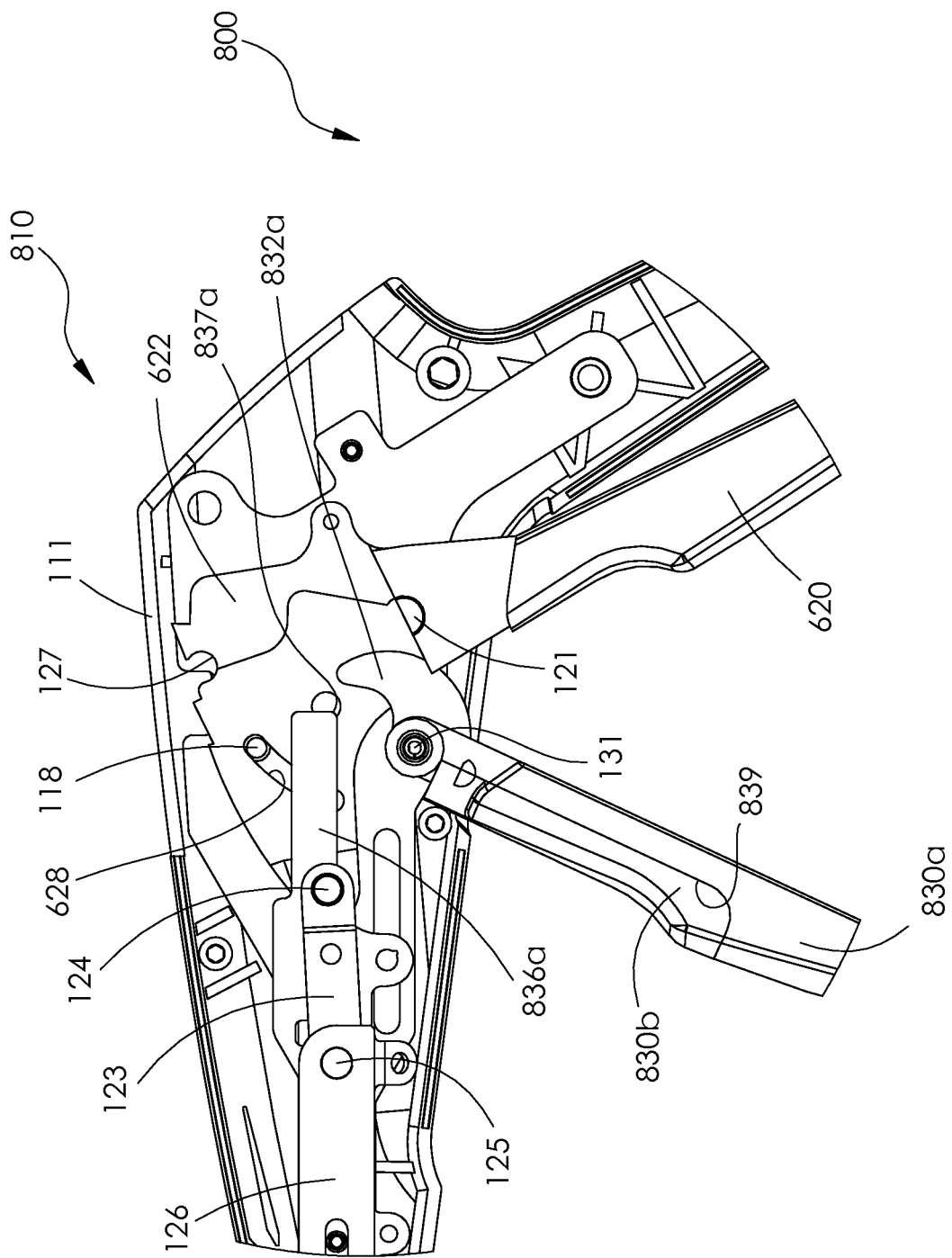
FIG. 36 is a partial cross-sectional view of the surgical stapling instrument of FIG. 34 in a clamped configuration prior to a firing stroke.

A surgical stapling instrument 800 is illustrated in FIGS. 34-38. The instrument 800 is similar to the instrument 100, 200, 300, 400, 500, 600, and/or 700 in many respects and/or the other surgical instruments disclosed herein. The instrument 800 comprises a handle 810 which includes a closure trigger 620 configured to operate a closure, or tissue clamping, system. The instrument 800 further comprises a firing trigger 830a configured to operate a staple firing system and a cutting trigger 830b configured to operate a tissue cutting system. The closure trigger 620 is rotatable between an unactuated position (FIG. 35) and an actuated position (FIG. 36). The closure system of the instrument 800 is similar to the closure system of the instrument 100 in many respects and is not repeated herein for the sake of brevity. In various instances, the instrument 800 includes a lockout system which prevents the actuation of the firing trigger 830a and/or the cutting trigger 830b prior to the actuation of the closure trigger 620.

Figure 37:
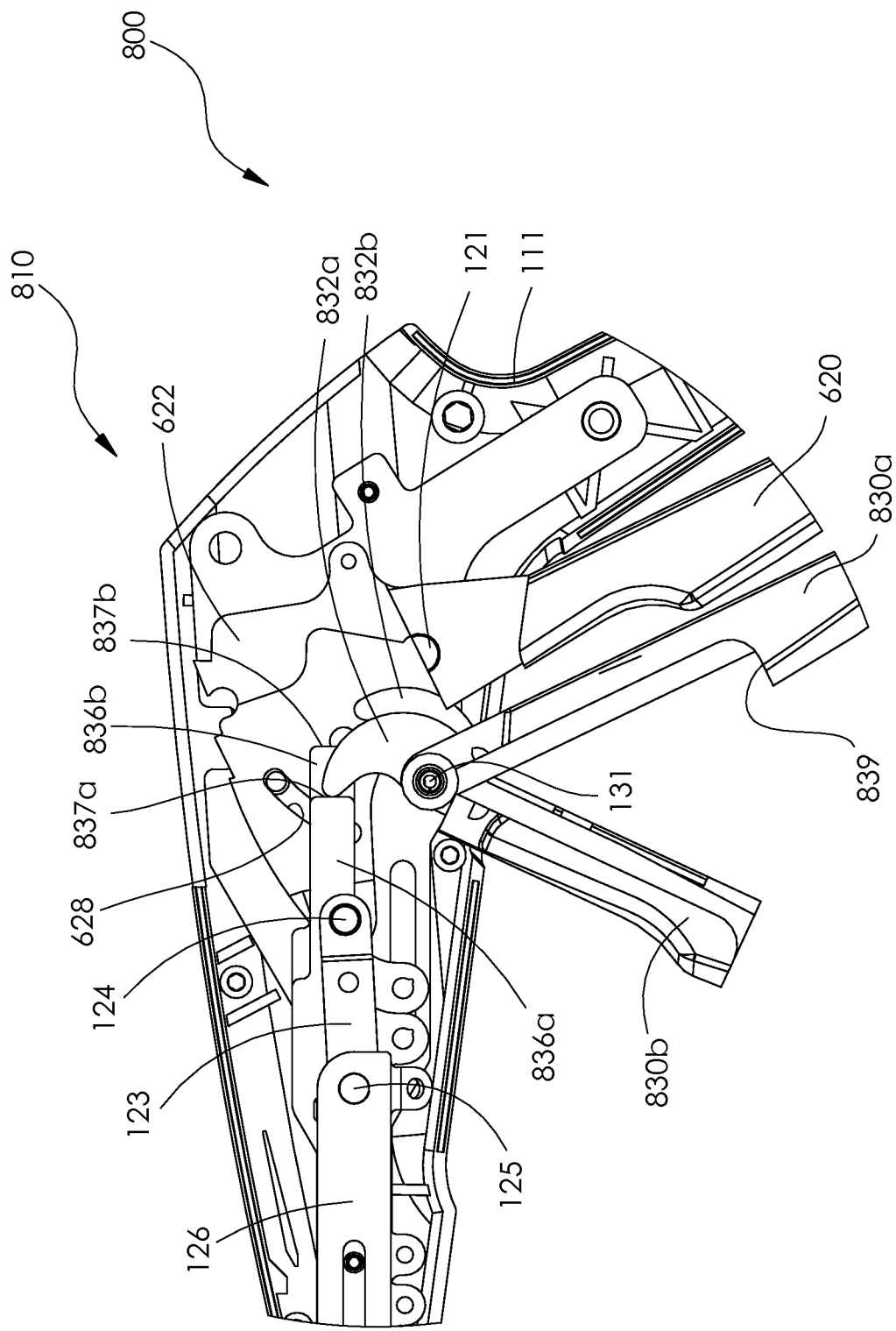
FIG. 37 is a partial cross-sectional view of the surgical stapling instrument of FIG. 34 in a clamped, fired configuration prior to a transection stroke.

The firing system of the instrument 800 is separate and distinct from the closure system. An actuation of the firing trigger 830a operates the staple firing system to deform staples removably stored in the end effector of the instrument 800. The firing trigger 830a is rotatably mounted to the handle 810 about a pivot 131 between an unfired position (FIG. 36) and a fired position (FIG. 37). The firing trigger 830a comprises a curved cam member 832a extending therefrom which is moved distally when the firing trigger 830a is actuated, as illustrated in FIG. 36. The cam member 832a contacts a proximal end 837a of a staple firing bar 836a when the cam member 832a is advanced distally in order to drive and deform the staples removably stored in the end effector of the instrument 800.

Figure 38:
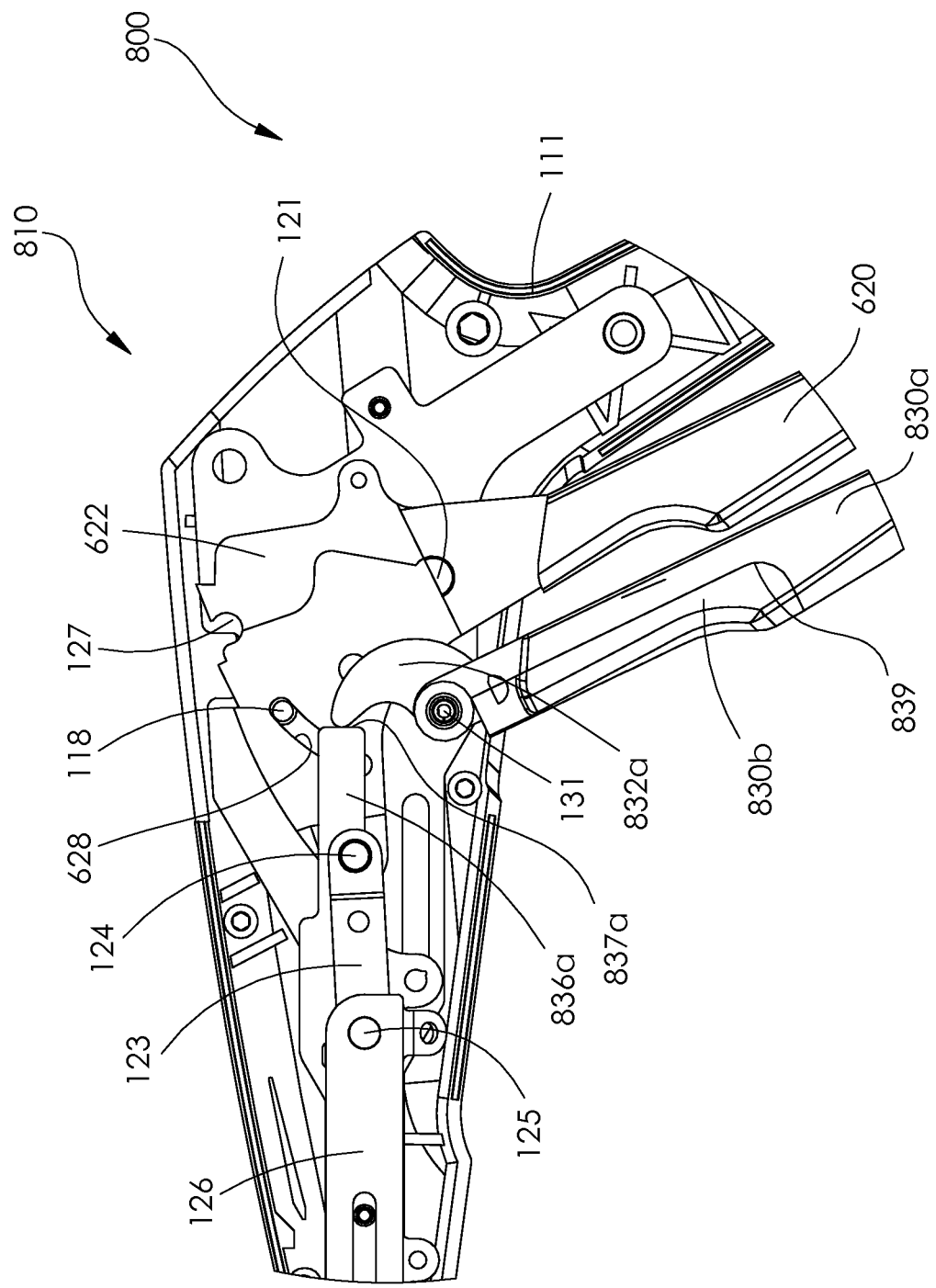
FIG. 38 is a partial cross-sectional view of the surgical stapling instrument of FIG. 34 in a clamped, fired configuration after the transection stroke.
Figure 39:
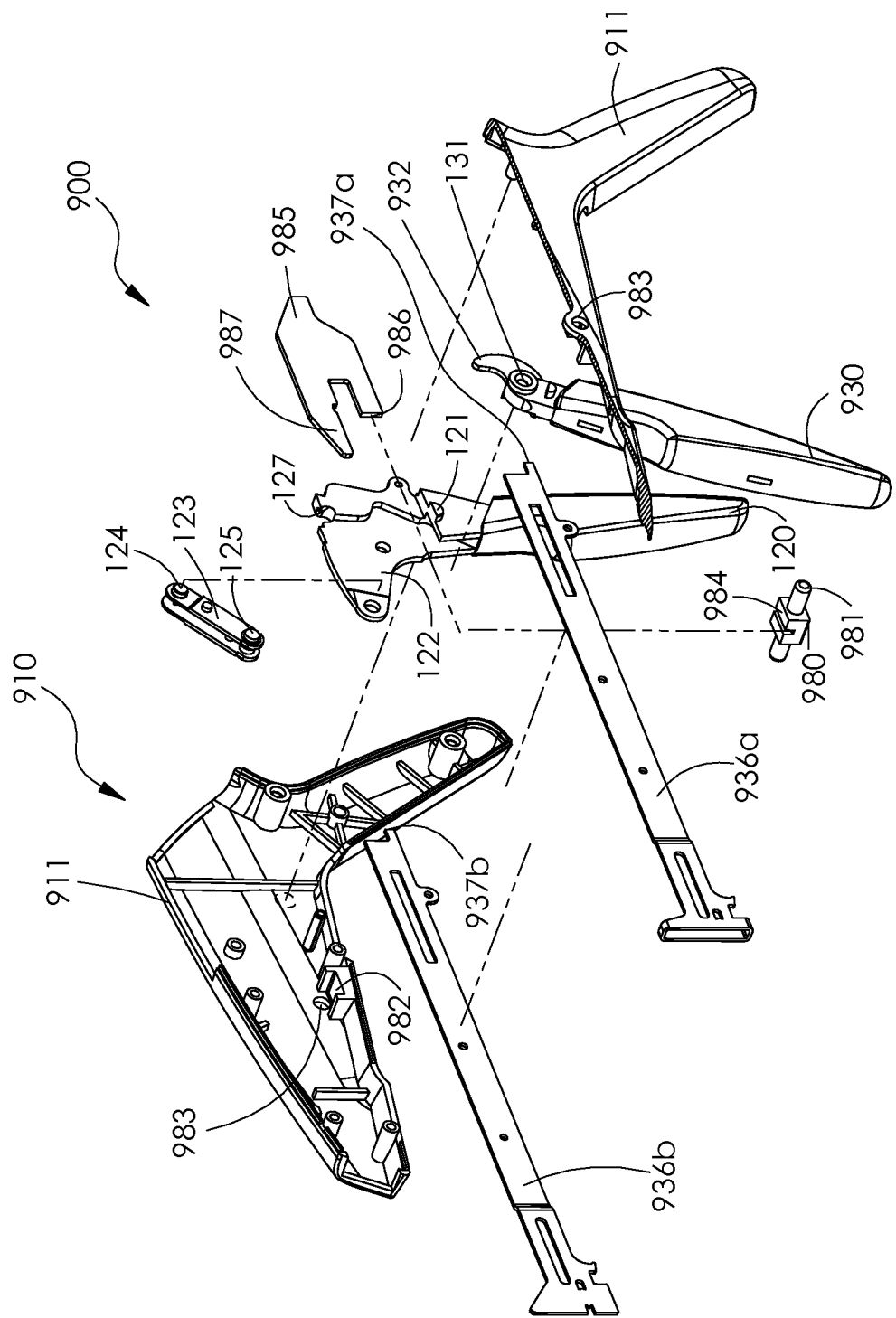
FIG. 39 is an exploded view of a surgical stapling instrument in accordance with at least one embodiment illustrated with components removed for the purpose of illustration.
Figure 40:
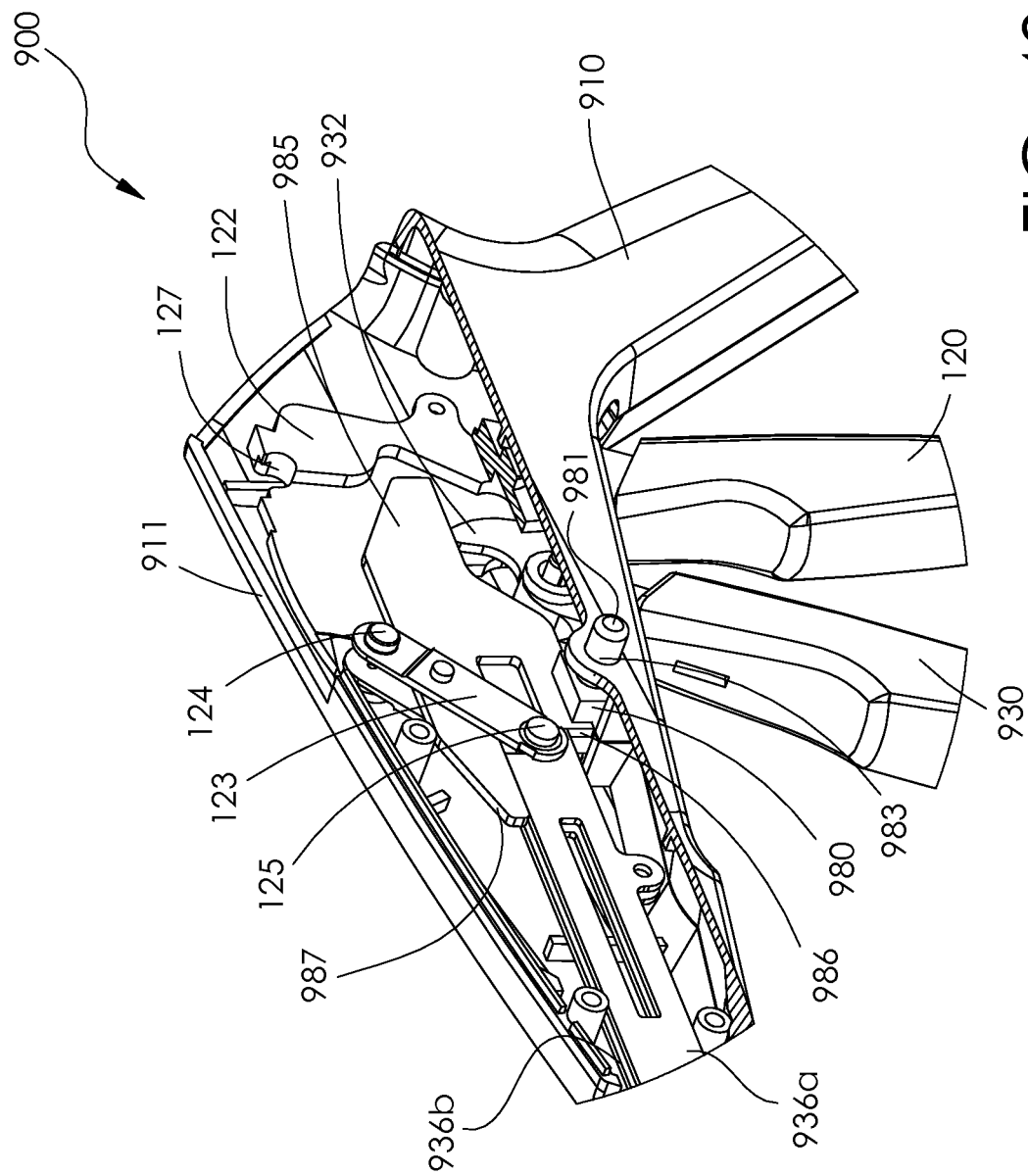
FIG. 40 is a partial cross-sectional view of a handle of the surgical stapling instrument of FIG. 39 illustrated in an unclamped configuration.

The cutting system of the instrument 800 is separate and distinct from the firing system and the closure system. An actuation of the cutting trigger 830b operates the tissue cutting system to cut the tissue captured within the end effector of the instrument 800. The cutting trigger 830b is rotatably mounted to the handle 810 about the pivot 131 between an unactuated position (FIG. 37) and an actuated position (FIG. 38). The cutting trigger 830b comprises a curved cam member 832b extending therefrom which is moved distally when the cutting trigger 830b is actuated, as illustrated in FIG. 38. The cam member 832b contacts a proximal end 837b of a tissue cutting bar 836b when the cam member 832b is advanced distally in order to cut the tissue.

The firing actuator 830a is rotated through a first range of motion to complete a firing stroke of the firing bar 836a and the cutting actuator 830b is rotated through a second range of motion to complete a cutting stroke of the cutting bar 836b. The firing stroke is the same length as, or at least substantially the same length as, the cutting stroke; however, other embodiments are envisioned in which the length of the firing stroke is different than the length of the cutting stroke.

Moreover, the first range of motion of the firing actuator 830a is the same as, or at least substantially the same as, the second range of motion of the cutting actuator 830b; however, other embodiments are envisioned in which the first range of motion is different than the second range of motion.

Referring again to FIGS. 37 and 38, the firing actuator 830a comprises a recess 839 defined therein. The recess 839 is configured to receive, or at least partially receive, the cutting actuator 830b therein. As illustrated in FIG. 36, the cutting actuator 830b is nested with the firing actuator 830a when the firing actuator 830a and the cutting actuator 830b are in their unactuated positions. When the firing actuator 830a is moved into its actuated position, as illustrated in FIG. 37, the actuators 830a, 830b can become un-nested as the cutting actuator 830b can remain behind in its unactuated position. Thereafter, the actuation of the cutting actuator 830b can re-nest the actuator 830b with the firing actuator 830a, as illustrated in FIG. 38.

Further to the above, the separate and distinct actuators 830a, 830b can permit the staple firing system and the tissue cutting system of the instrument 800 to be selectively operated in a separate and distinct manner. That said, a surgeon has the option of actuating the actuators 830a, 830b of the instrument 800 simultaneously. In such instances, the instrument 800 will staple and cut the tissue captured in the end effector simultaneously. Alternatively, in at least one embodiment, the instrument 800 can include a lockout configured to prevent the cutting actuator 830b from being actuated prior to the complete actuation of the firing actuator 830a. In such embodiments, the surgeon would not have the option of actuating the actuators 830a and 830b simultaneously, but still have the option of selectively actuating the cutting actuator 830b. In a further alternative embodiment, the cutting actuator 830b could become unlocked at some point during the actuation of the firing actuator 830a such that the actuators 830a, 830b could be thereafter actuated simultaneously, if desired by the surgeon. Such an embodiment could assure that the staples have been at least partially fired, or at least sufficiently fired, prior to cutting the tissue.

Figure 41:
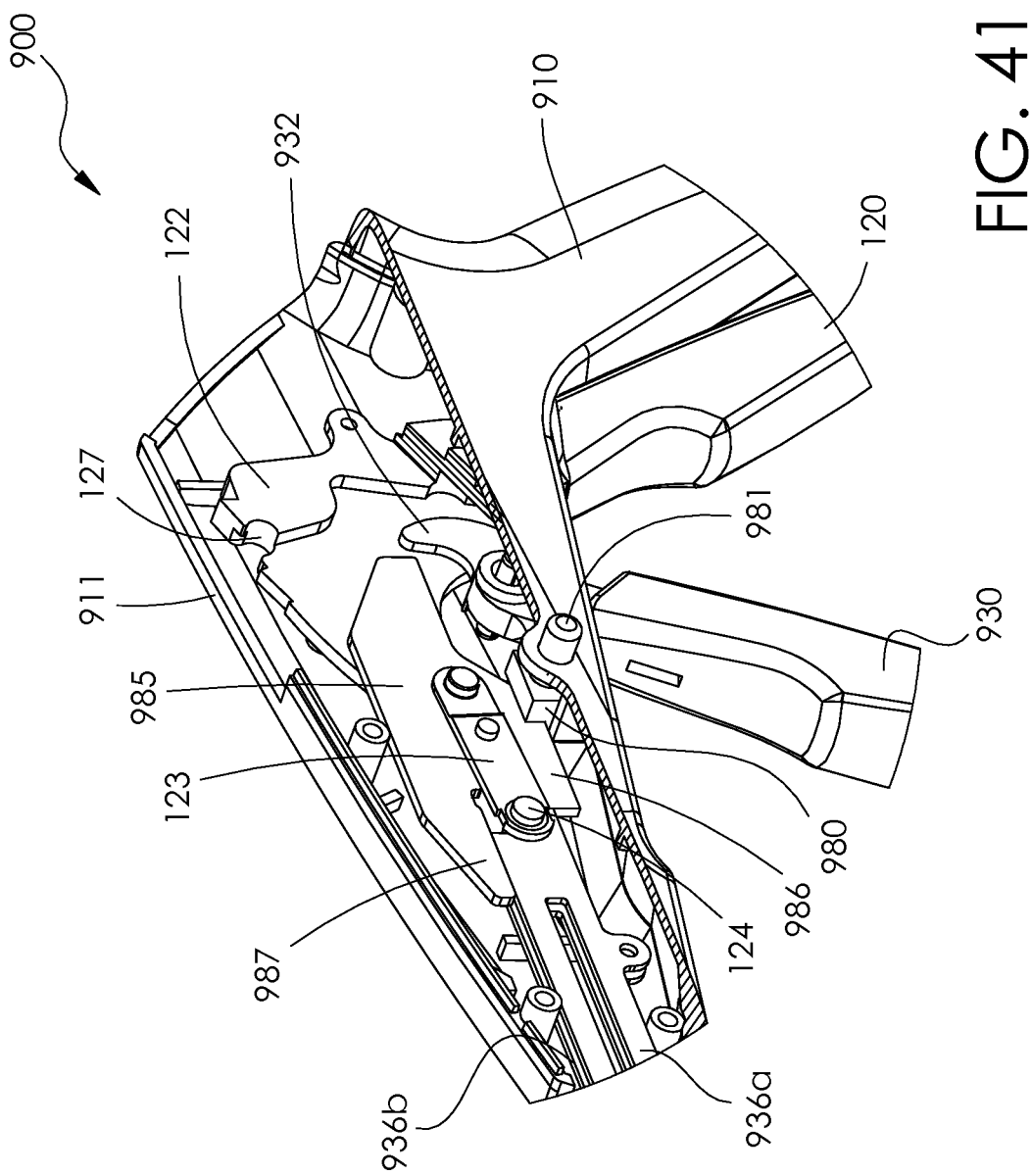
FIG. 41 is a partial cross-sectional view of the handle of FIG. 40 illustrated in a tissue-stapling operating mode.

A surgical stapling instrument 900 is illustrated in FIGS. 39-44. The instrument 900 is similar to the instrument 100, 200, 300, 400, 500, 600, 700, 800, and/or the other surgical instruments disclosed herein in many respects. The instrument 900 comprises a handle 910 including a housing 911, a closure trigger 620 configured to operate a closure, or tissue clamping, system, and a firing trigger 930a configured to operate, one, a staple firing system and, two, a tissue cutting system. The closure trigger 620 is rotatable between an unactuated position (FIG. 40) and an actuated position (FIG. 41). The closure system of the instrument 900 is similar to the closure system of the instrument 100 in many respects and is not repeated herein for the sake of brevity. In various instances, the instrument 900 includes a lockout system which prevents the actuation of the firing trigger 930 prior to the actuation of the closure trigger 620.

Figure 42:
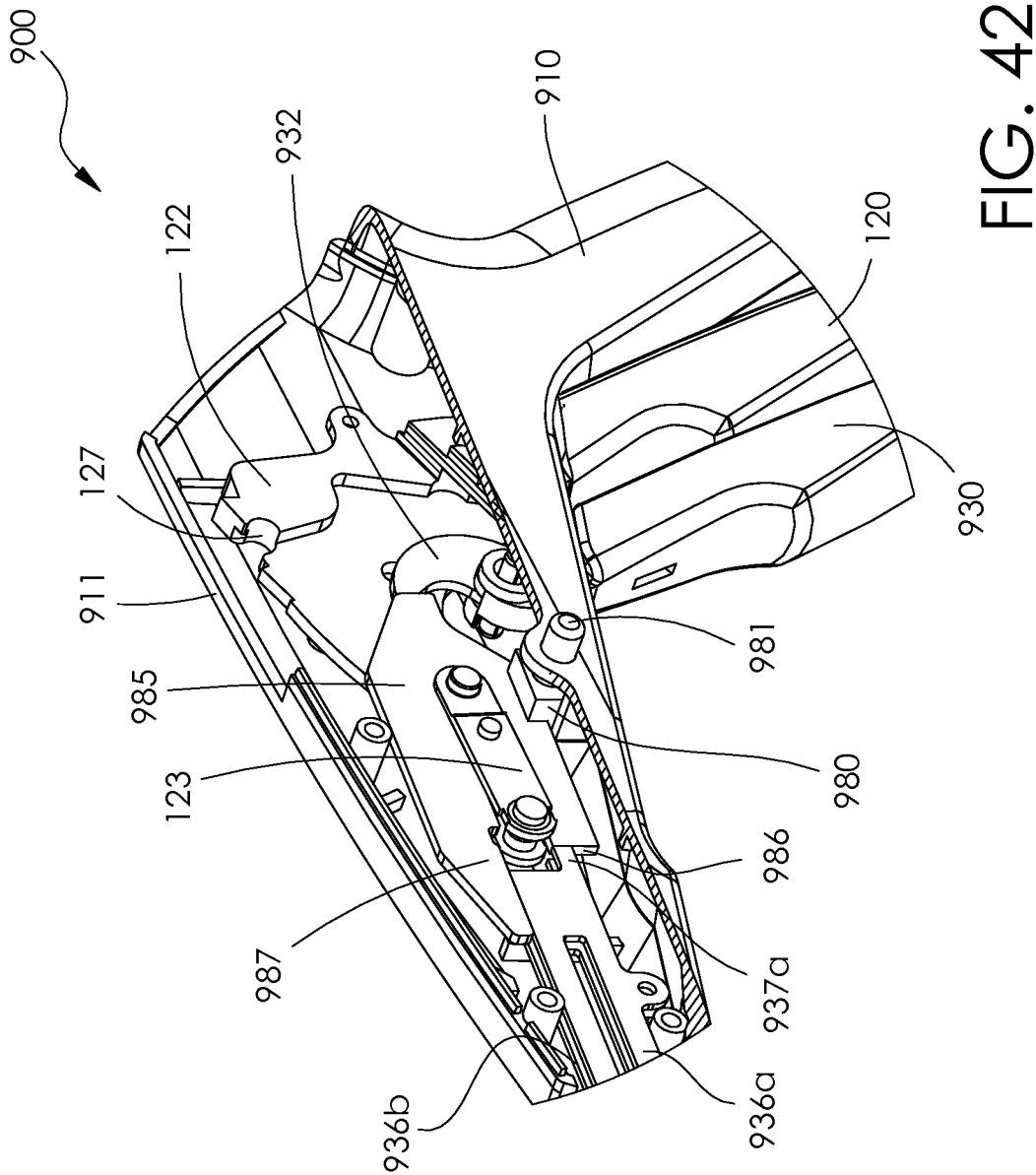
FIG. 42 is a partial cross-sectional view of the handle of FIG. 40 illustrated in a fired configuration.
Figure 43:
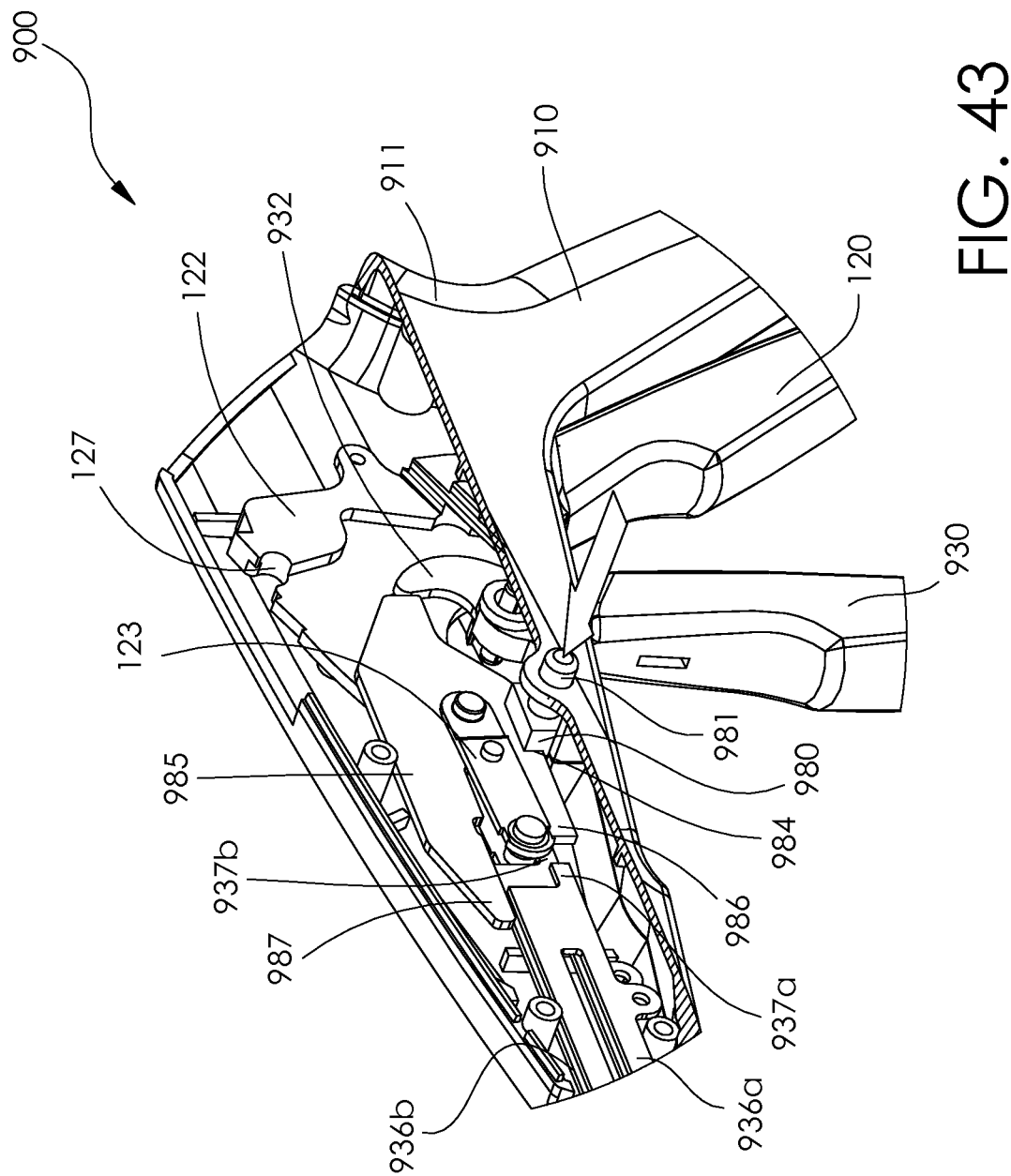
FIG. 43 is a partial cross-sectional view of the handle of FIG. 40 illustrating the handle being switched between its tissue-stapling operating mode and a tissue-transecting operating mode.

Further to the above, the firing trigger 930 is rotatably mounted to the handle housing 911 about a pivot 131 between an unactuated position (FIG. 41) and an actuated position (FIG. 42). As described in greater detail below, the firing trigger 930 operates the staple firing system during a first actuation of the firing trigger 930 (FIG. 42) and the tissue cutting system during a second actuation of the firing trigger 930 (FIG. 43). The firing trigger 930 comprises a curved cam portion 932 which moves distally when the firing trigger 930 is actuated. The cam portion 932 contacts a cam plate 985 when the cam portion 932 is rotated distally. The cam plate 985 is slidably mounted in the handle housing 911. The cam plate 985 is slidable longitudinally when it is pushed distally by the cam portion 932. The cam plate 985 comprises a drive slot defined between arms 986, 987 extending from the distal end of the cam plate 985. The drive slot is configured to receive a proximal end of a staple firing bar 936a such that, when the cam plate 985 is pushed distally, the cam plate 985 drives the firing bar 936a distally to fire the staples removably stored within the end effector of the instrument 900. More specifically, the distally-extending arm 986 contacts a proximal end 987a of the staple firing bar 936a to push the firing bar 936a distally.

Figure 44:
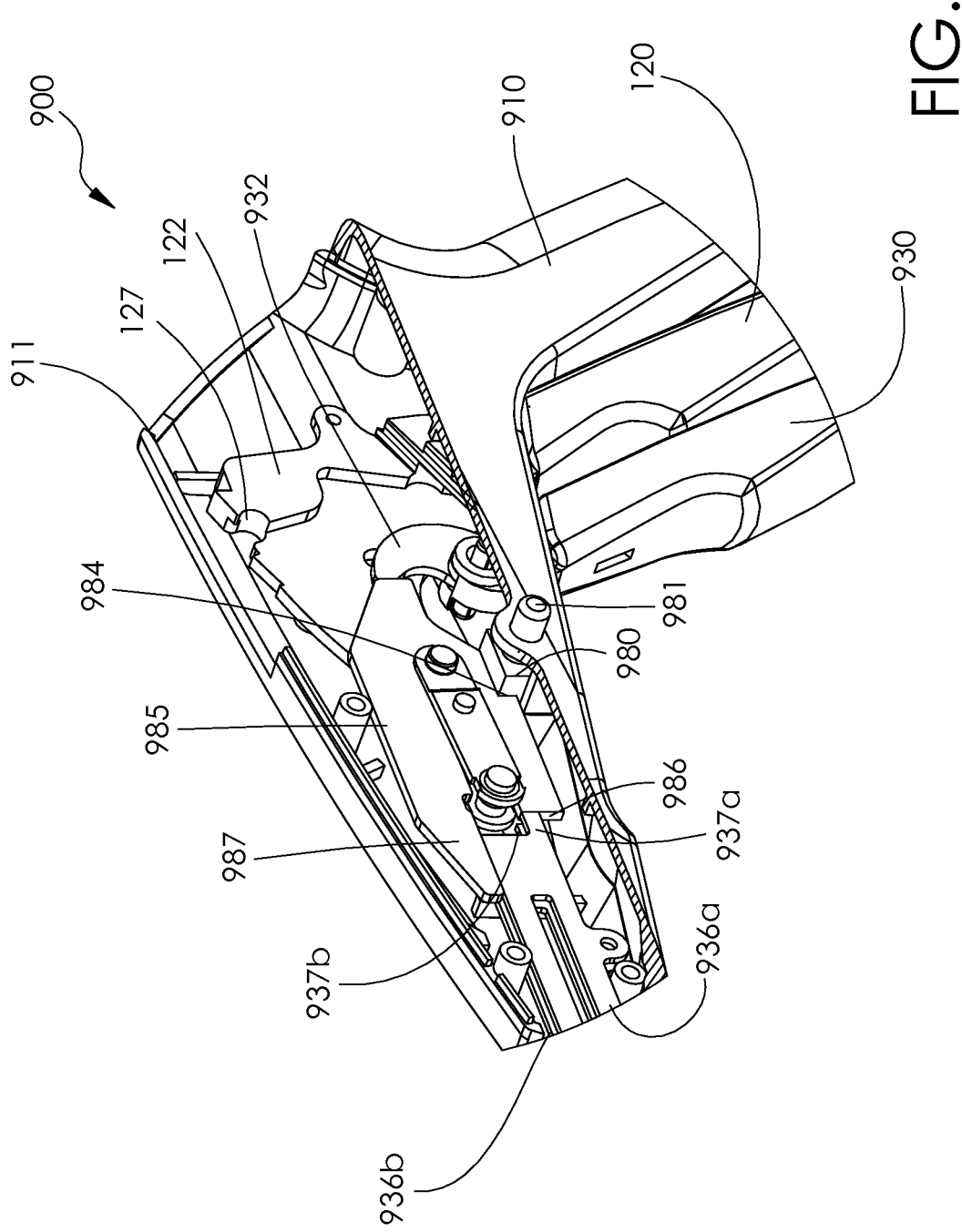
FIG. 44 is a partial cross-sectional view of the handle of FIG. 40 after a tissue transection stroke.

Further to the above, the cam plate 985 is also slidable laterally. More specifically, the cam plate 985 is slidable between a first position in which the cam plate 985 is operably engageable with the staple firing bar 936a (FIGS. 41 and 42) and a second position in which the cam plate 985 is operably engageable with a tissue cutting bar 936b (FIGS. 43 and 44). The handle 910 further comprises a pusher block 980 engaged with the cam plate 985. The pusher block 980 comprises a push pin 981 extending therefrom which extends through the handle housing 911. The pusher block 980 can include another push pin 981 extending through the handle housing 911 in an opposite direction. In any event, the user of the surgical instrument 900 can shift the pusher block 980 between its first position and its second position by applying a force to one of the push pins 981. When the pusher block 980 is in its second position, the tissue cutting bar 936b is positioned in the drive slot defined between the arms 986 and 987. At such point, the cam plate 985 is operably coupled with the tissue cutting bar 936b and a subsequent actuation of the firing trigger 930 will actuate the tissue cutting system.

In use, the instrument 900 is positioned in a patient and the end effector of the instrument 900 is positioned relative to the tissue that is to be treated. The closure trigger 620 is then actuated to clamp the end effector onto the tissue. At such point, the pusher block 980 is positioned in its first position and is operably engaged with the staple firing bar 936a. An actuation of the firing trigger 930 then advances the staple firing bar 936a distally; however, this actuation of the firing trigger 930 does not advance the tissue cutting bar 936b as the cam slide 985 is not engaged with the tissue cutting bar 936b. After the firing trigger 930 has been actuated, the firing trigger 930 can be released and returned to its unactuated position, as illustrated in FIG. 43. Similar to the above, the handle 910 can include a return spring configured to return the firing trigger 930 back to its unactuated position. As also illustrated in FIG. 43, the firing bar 936a remains in its fired position when the firing trigger 930 is returned to its unactuated position. Turning now to FIG. 44, the pusher block 980 can be moved into its second position to disengage the pusher block 980 from the staple firing bar 936a and engage the pusher block 980 with the tissue cutting bar 936b. An actuation of the firing trigger 930 can then advance the tissue cutting bar 936b distally to cut the tissue; however, the surgeon has the option of not cutting the tissue and can release the tissue from the end effector without actuating the firing trigger 930 a second time. The handle 910 can include a release mechanism configured to return the closure trigger 620 and the closure system back to their unfired positions. In any event, the instrument 900 can include one or more return springs and/or return mechanisms for resetting the bars 936a, 936b to their unactuated positions. In at least one instance, the bars 936a, 936b can be reset when the end effector is re-opened.

Figure 45:
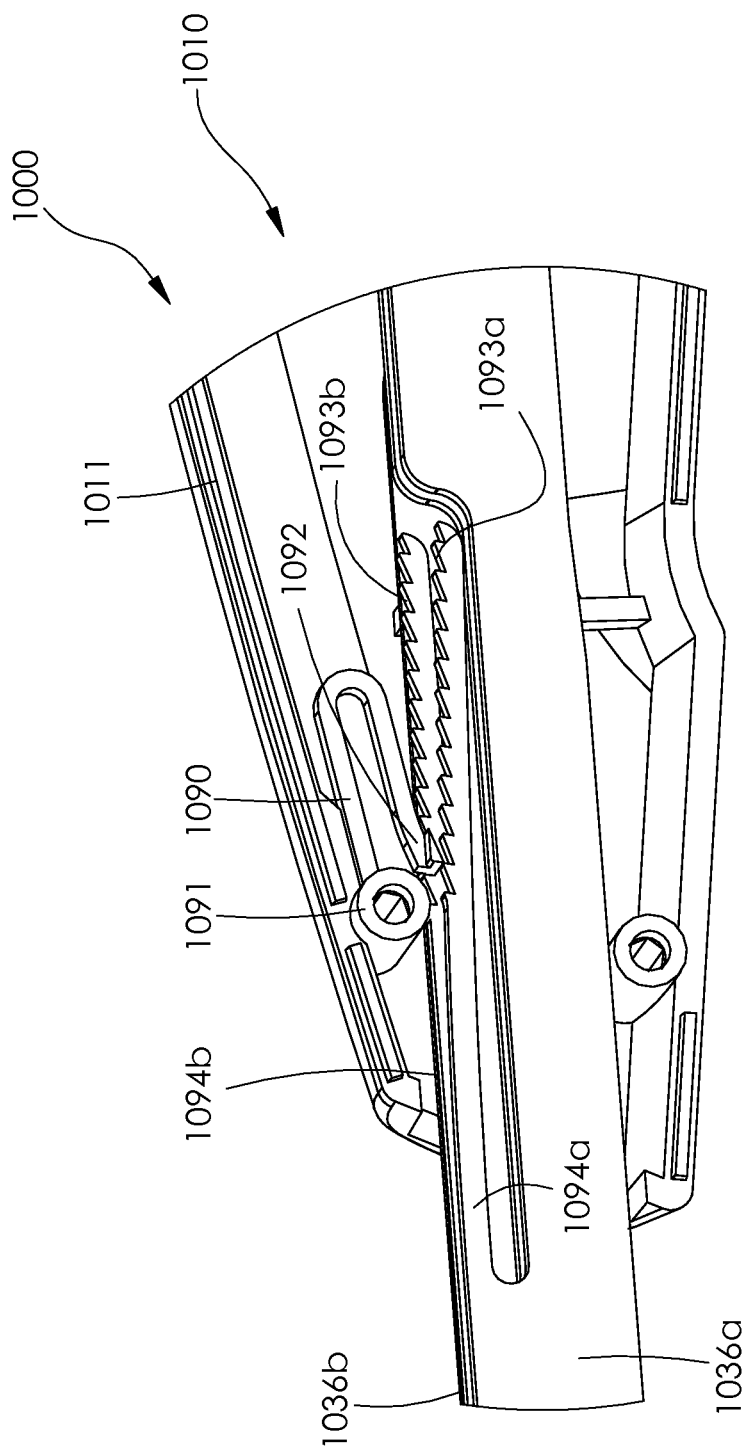
FIG. 45 is a partial cross-sectional view of a surgical stapling instrument in accordance with at least one embodiment including a staple firing bar, a knife bar, and a lock configured to hold the firing bar in position while the knife bar is advanced relative to the firing bar.

As discussed above, the staple firing bar 936a remains in its distal, fired position while the firing trigger 930 is re-actuated to drive the tissue cutting bar 936b distally. In various instances, the firing bar 936a may remain in its fired position owing to frictional forces between the firing bar 936a and the frame of the instrument 900, for example; however, such frictional forces may be overcome and the firing bar 936a can be pushed proximally. In certain instances, turning now to FIG. 45, a staple firing bar and/or a tissue cutting bar can include means for affirmatively holding the bars in an actuated, or an at least partially actuated, position.

Figure 46:
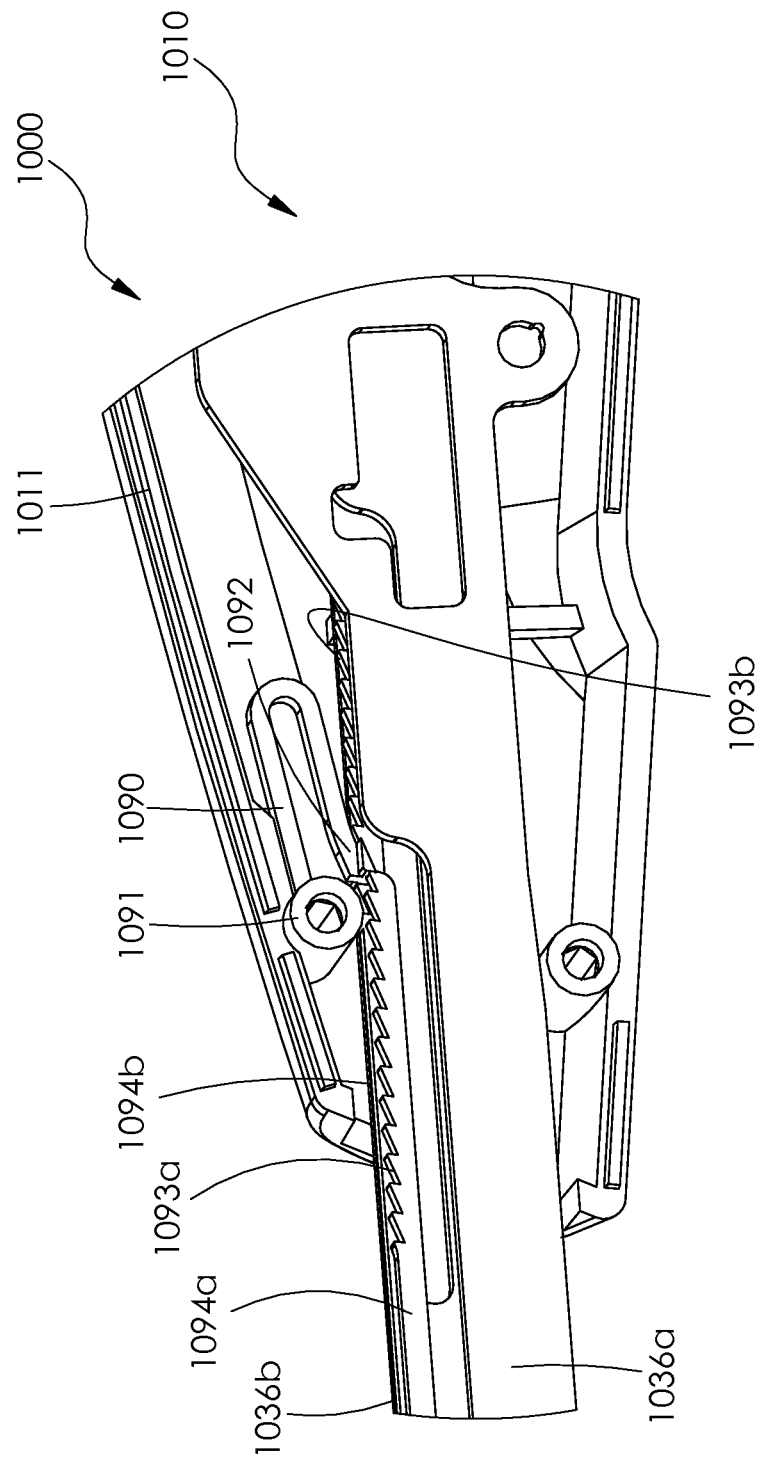
FIG. 46 illustrates the firing bar of FIG. 45 in a fired position and the lock positioned behind the staple firing bar.

In at least one exemplary embodiment, further to the above, a surgical instrument 1000 comprises a handle 1010 including a handle housing 1011. The instrument 1000 further comprises a staple firing bar 1036a configured to eject and deform staples removably stored in an end effector of the instrument 1000 when the firing bar 1036a is pushed distally. The instrument 1000 also comprises a tissue cutting bar 1036b configured to incise the tissue captured within the end effector of the instrument 1000. The handle 1010 comprises a lock 1090, for example, which is configured to hold the firing bar 1036a in position while the cutting bar 1036b is being actuated. The lock 1090 comprises a first end mounted the handle housing 1011 and a second, or cantilever, end 1092 engaged with a rack 1093a of the firing bar 1036a. The rack 1093a comprises a longitudinal array of teeth which is configured to permit the firing bar 1036a to move distally relative to the lock 1090, as illustrated in FIG. 46, and prevent the firing bar 1036a from moving proximally relative to the lock 1090 until the lock 1090 is released from the firing bar 1036a.

Figure 47:
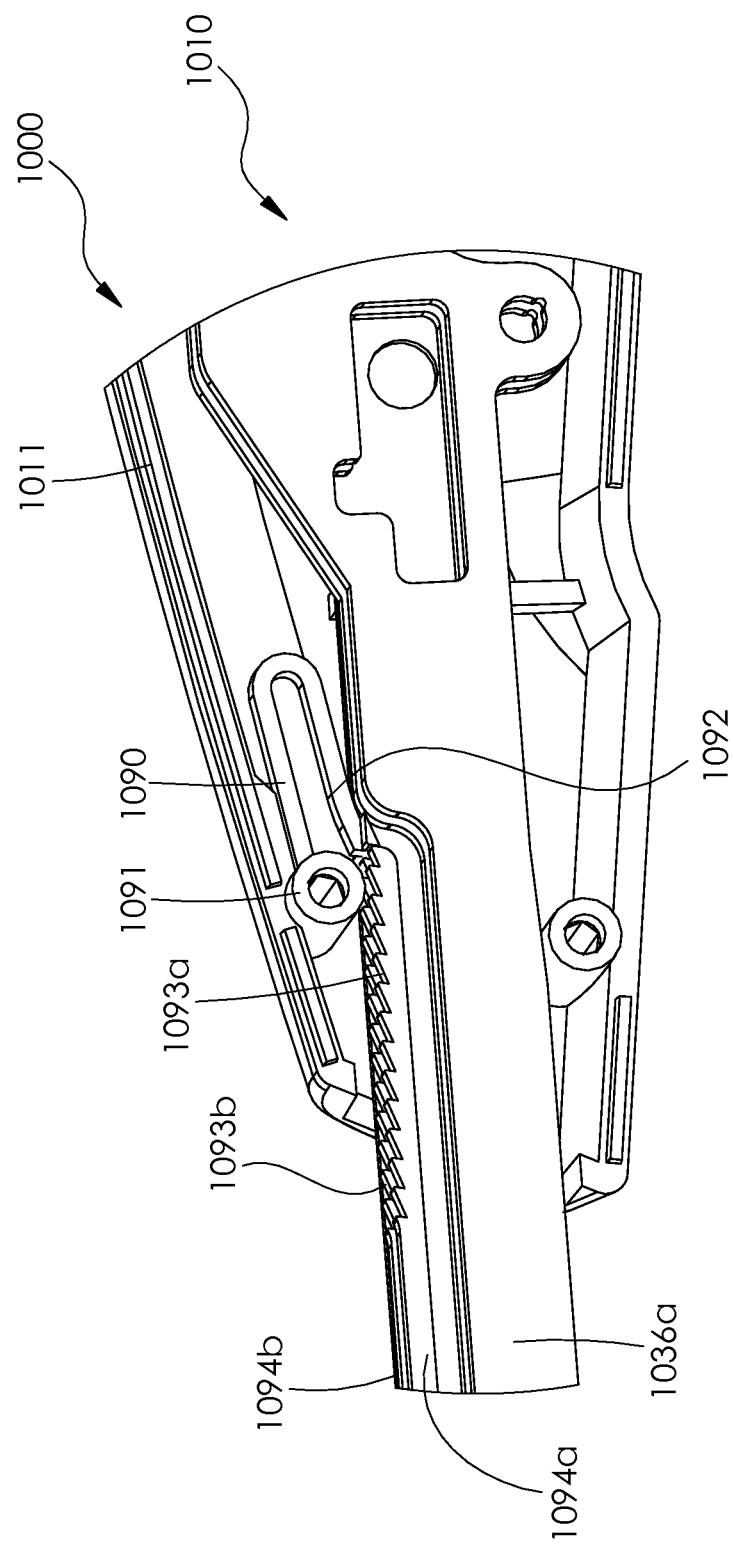
FIG. 47 illustrates the knife bar of FIG. 45 in a fired position.
Figure 48:
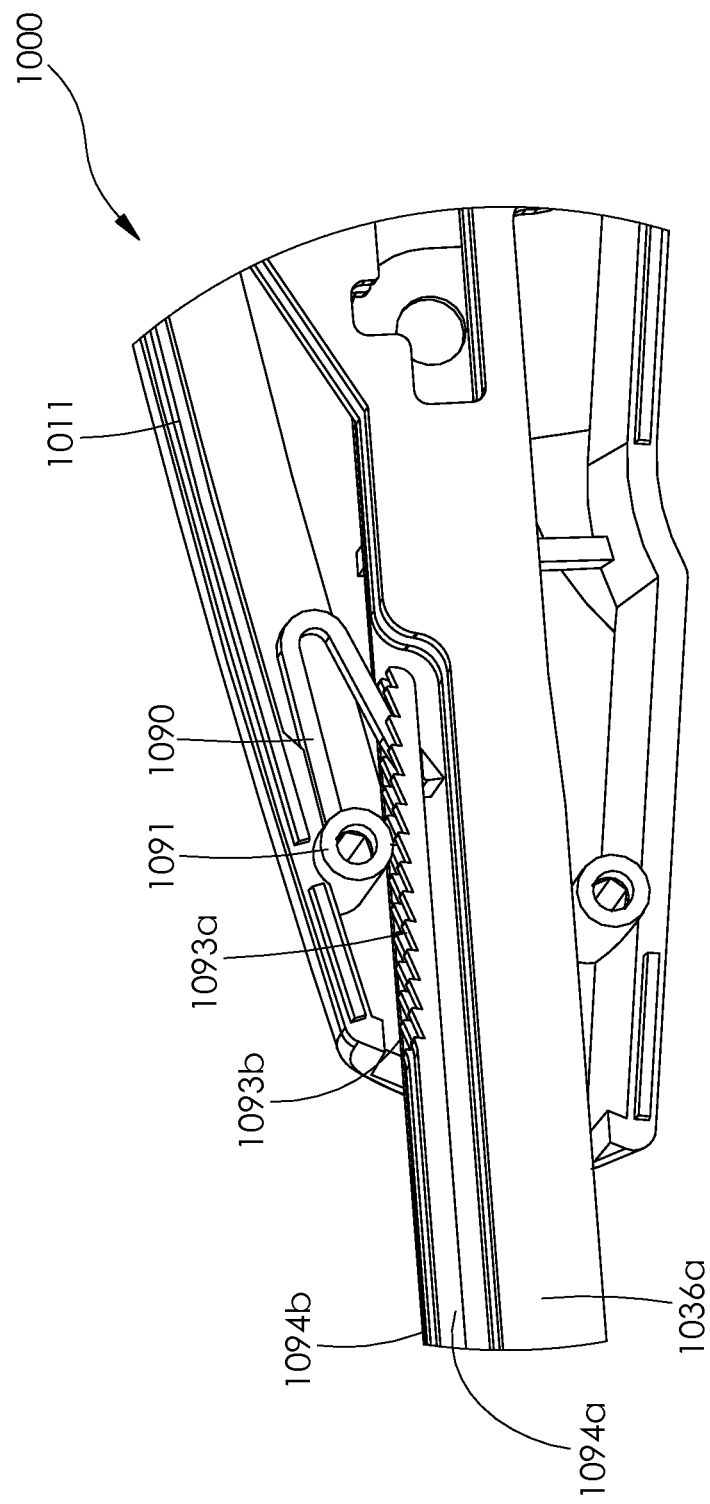
FIG. 48 illustrates the lock of FIG. 45 disengaged from the staple firing bar such that the firing bar can be retracted.

Further to the above, the lock 1090 sequentially positions itself behind each tooth of the rack 1093a as the firing bar 1036a passes by the lock 1090. In the event that the surgeon were to pause the advancement of the firing bar 1036a at some point during the firing stroke of the firing bar 1036a, the lock 1090 can hold the firing bar 1036a in position until the firing stroke is resumed. After the staple firing stroke has been completed, the lock 1090 is positioned behind the proximal-most tooth of the firing bar 1036a. At such point, the lock 1090 is held in engagement with the firing bar 1036a by the tissue cutting bar 1036b. The cutting bar 1036b comprises a rack 1093b defined thereon which, similar to the above, includes a longitudinal array of teeth which is configured to permit the cutting bar 1036b to move distally relative to the lock 1090, as illustrated in FIG. 47, and prevent the cutting bar 1036b from moving proximally relative to the lock 1090 until the cutting bar 1036b has completed its cutting stroke, as illustrated in FIG. 48. At such point, the lock 1090 can slip off the ends of the firing bar 1036a and the cutting bar 1036b and become disengaged from the bars 1036a and 1036b.

Further to the above, the lock 1090 is held in a flexed configuration by the bars 1036a and 1036b such that the lock 1090 can resiliently expand and disengage itself from the bars 1036a and 1036b after the racks 1093a and 1093b have passed by the lock 1090. The rack 1093a is defined on a flexible cantilever 1094a extending proximally from the firing bar 1036a and the rack 1093b is defined on a flexible cantilever 1094b extending proximally from the cutting bar 1036b. The racks 1093a and 1093b are configured to co-operatively flex with the lock 1090. In any event, the bars 1036a and 1036b can be returned to their unactuated positions after the lock 1090 has become disengaged from the racks 1093a and 1093b, respectively. In various instances, one or more return springs can be associated with the bars 1036a and 1036b to return the bars 1036a and 1036b to their unactuated positions.

Figure 49:
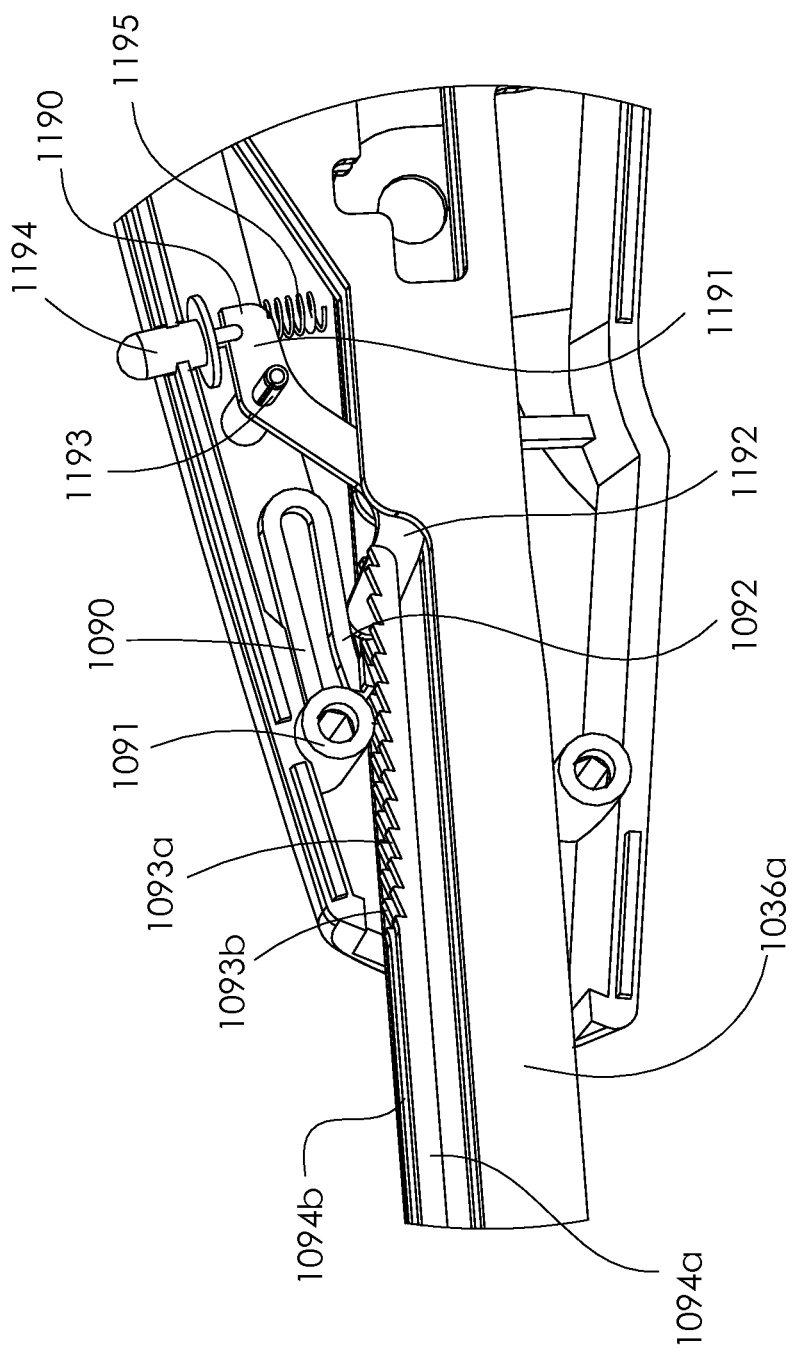
FIG. 49 is a partial cross-sectional view of a surgical stapling instrument in accordance with at least one alternative embodiment comprising a manually-releasable lock.

Turning now to FIG. 49, the instrument 1000 can include a reset actuator, such as actuator 1190, for example, which can disengage the lock 1090 from the firing bar 1036a and/or the cutting bar 1036b prior to the completion of the firing stroke and/or cutting stroke of the instrument 1000. The actuator 1190 comprises a first end 1191 rotatably mounted to the handle housing via a pivot pin 1193 and, in addition, a second end 1192 configured to engage the lock 1090. A push button 1194 is operably engaged with the first end 1191 of the actuator 1190 and is configured to rotate the second end 1192 of the actuator 1190 into engagement with the lock 1090, as illustrated in FIG. 49, when the push button 1194 is depressed. In such instances, the actuator 1190 flexes the second end 1092 of the lock 1090 away from the bars 1036a and 1036b and disengages the lock 1090 from the racks 1093a and 1093b. At such point, the bars 1036a and 1036b can be retracted to their unactuated positions. Such a release actuation system can allow to the instrument 1000 to be quickly opened and unclamped from the tissue at any suitable point during the operation of the instrument 1000. The push button 1194 can be depressed to release the lock 1090 during the firing stroke, after the firing stroke, during the cutting stroke, and/or after the cutting stroke.

Referring to FIGS. 50-53, a surgical instrument 1200 comprises an end effector 1250 and a closure system configured to close the end effector 1250. The end effector 1250 comprises a staple cartridge 1260 and an anvil 170. The staple cartridge 1260 comprises a cartridge body 161, a plurality of staple cavities defined in the cartridge body, and staples removably stored in the staple cavities. The staple cartridge 1260 is movable toward the anvil 170 between an open position (FIG. 50) and a closed position (FIG. 51) to compress tissue between the cartridge body 161 and the anvil 170. The instrument 1200 further comprises a closure bar 126 mounted to the cartridge body 161. The closure bar 126 can be advanced distally to move the staple cartridge 1260 distally and retracted proximally to move the staple cartridge 1260 proximally. The end effector 1250 further comprises a guide rail 168 configured to guide the staple cartridge 1260 along a longitudinal axis as the staple cartridge 1260 is moved proximally and distally.

Figure 50:
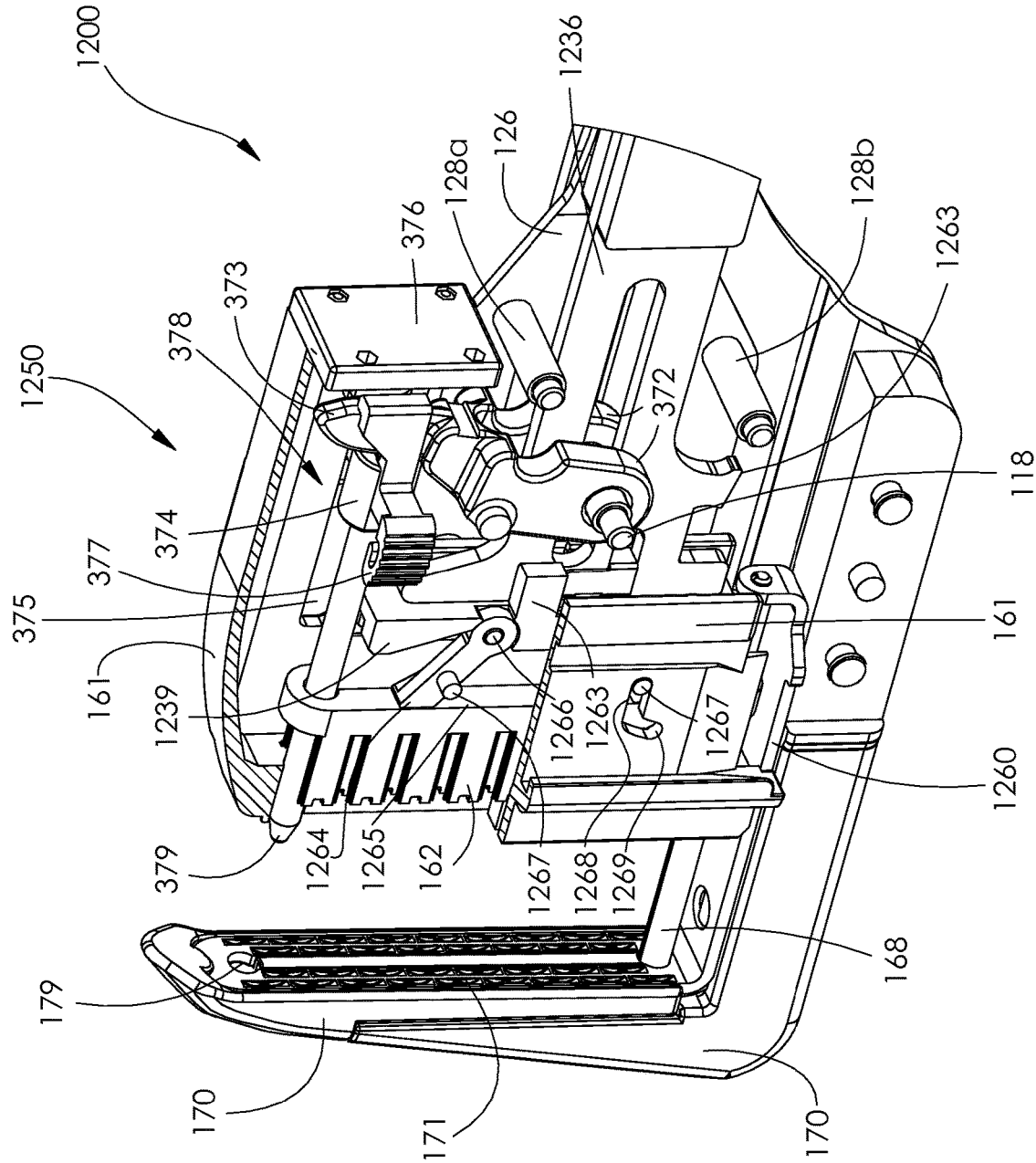
FIG. 50 is a partial cross-sectional view of a surgical stapling instrument in accordance with at least one embodiment illustrated in an unclamped configuration.
Figure 51:
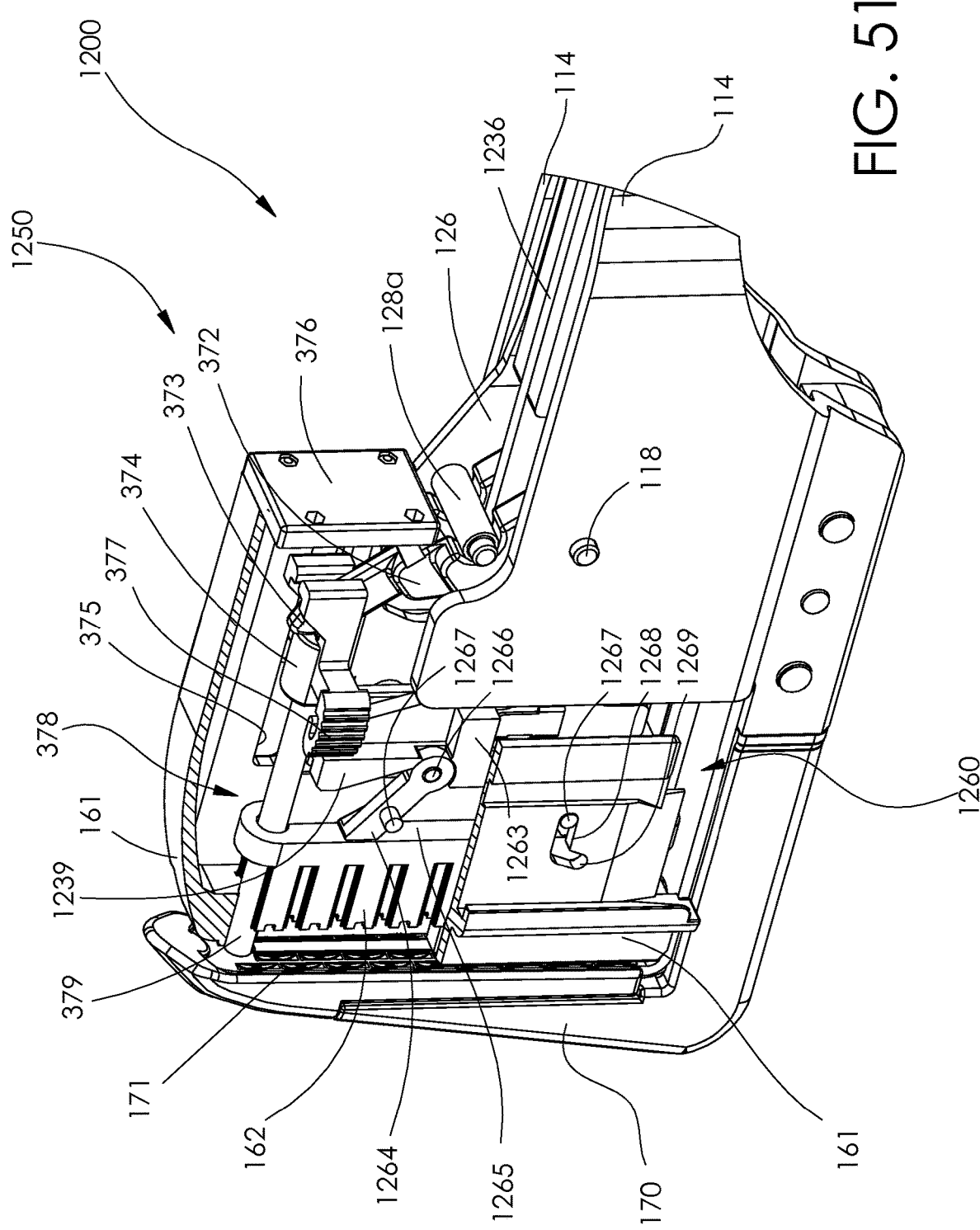
FIG. 51 is a partial cross-sectional view of the surgical stapling instrument of FIG. 50 illustrated in a clamped configuration.

Referring primarily to FIGS. 50 and 51, the distal advancement of the closure bar 126 also advances a tissue pin 379 distally to capture tissue within the end effector 1250. More specifically, the closure bar 126 comprises a drive pin 128a extending laterally therefrom which is configured to engage one or more tissue pin actuators 372 as the closure bar 126 is moved distally. The tissue pin actuators 372 are rotatably mounted to the shaft frame 114 about a pivot pin 118 and are movable between an unactuated position (FIG. 50) and an actuated position (FIG. 51). Each tissue pin actuator 372 comprises a drive portion 373 configured to engage and push a base 374 of the tissue pin 379. The tissue pin 379 is slidably retained in a cavity 378 defined in the end effector 1250 such that the movement of the tissue pin 379 is constrained to a longitudinal path. The anvil 170 includes a pin aperture 179 defined therein which is configured to receive the tissue pin 379 when the tissue pin 379 has reached its fully-deployed position.

Further to the above, the staple cartridge 1260 moves toward the anvil 170 before the tissue pin 379 is deployed. In such instances, the tissue is consecutively clamped and then trapped within the end effector 1250; however, alternative embodiments are envisioned in which the tissue is concurrently clamped by the cartridge 1260 and trapped within the end effector 1250 by the tissue pin 379. Other embodiments are envisioned in which the tissue pin 379 is deployed before the staple cartridge 1260 is moved distally to compress the tissue.

Further to the above, the staple cartridge 1260 further comprises staple drivers 162 configured to drive the staples toward the anvil 170. The anvil 170 includes forming pockets 171 defined therein which are configured to deform the staples. As described in greater detail below, the staple drivers 162 are pushed distally by a firing bar 1236. Referring again to FIGS. 50 and 51, the closure bar 126 further comprises a second drive pin 128b extending laterally therefrom which is configured to engage the firing bar 1236 and move the firing bar 1236 distally with the cartridge 1260 when the cartridge 1260 is moved distally to clamp the tissue. In this way, the relative position of the firing bar 1236 and the staple cartridge 1260 can be maintained, or at least substantially maintained, during the closure of the end effector 1250.

Figure 52:
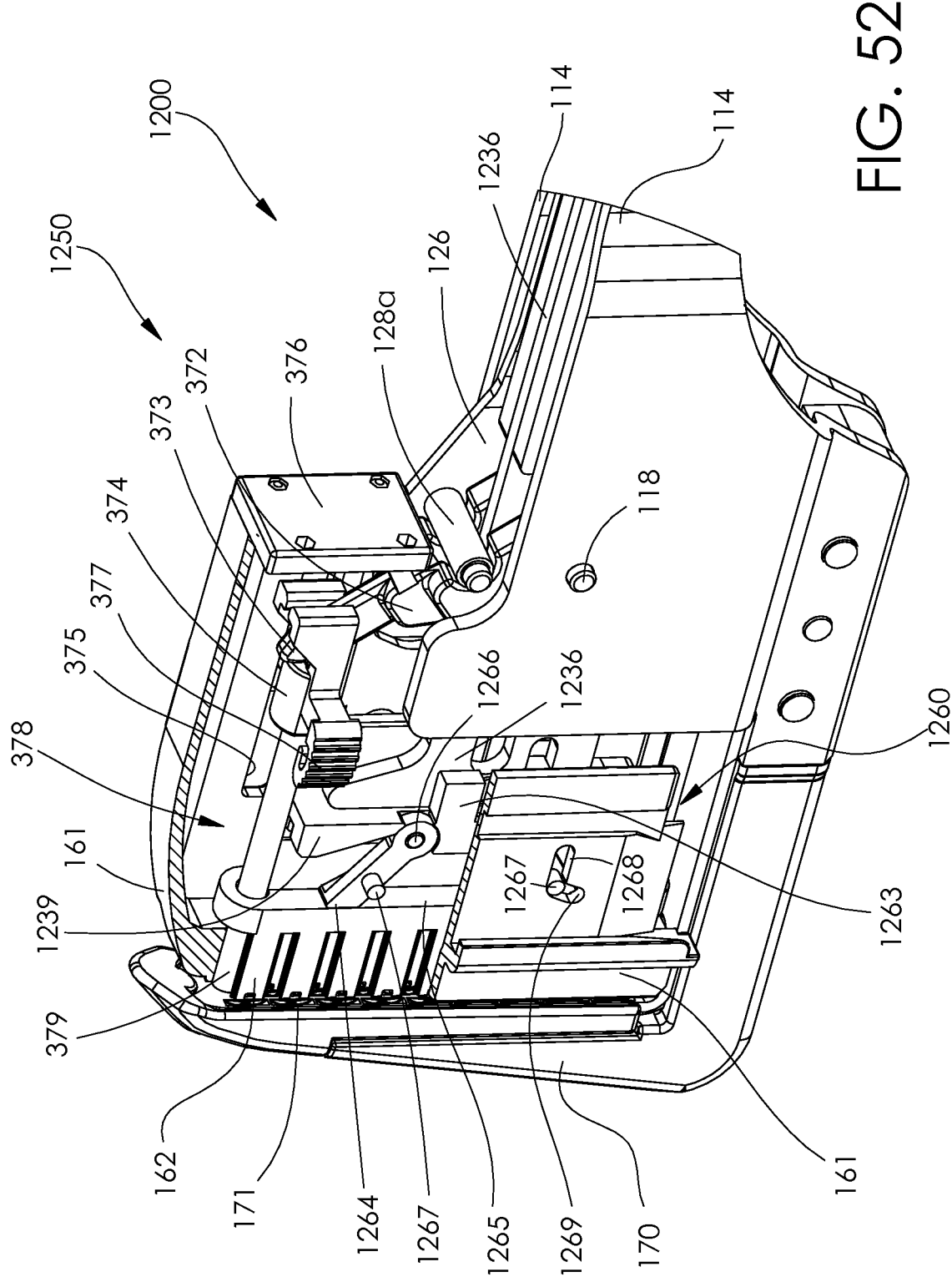
FIG. 52 is a partial cross-sectional view of the surgical stapling instrument of FIG. 50 illustrated in a staple-firing configuration.

The firing bar 1236 does not push directly on the staple drivers 162; rather, the firing bar 1236 pushes directly on an intermediate driver 1263 which transfers the movement of the firing bar 1236 to the staple drivers 162. More specifically, the intermediate driver 1263 comprises a plurality of drive arms 1264 extending distally therefrom which are in contact with a drive surface 1265 defined on the proximal side of the staple drivers 162. When the firing bar 1236 is being advanced distally to deform the staples against the anvil 170, as illustrated in FIG. 52, the drive arms 1264 transmit force between the firing bar 1236 and the staple drivers 162.

Figure 53:
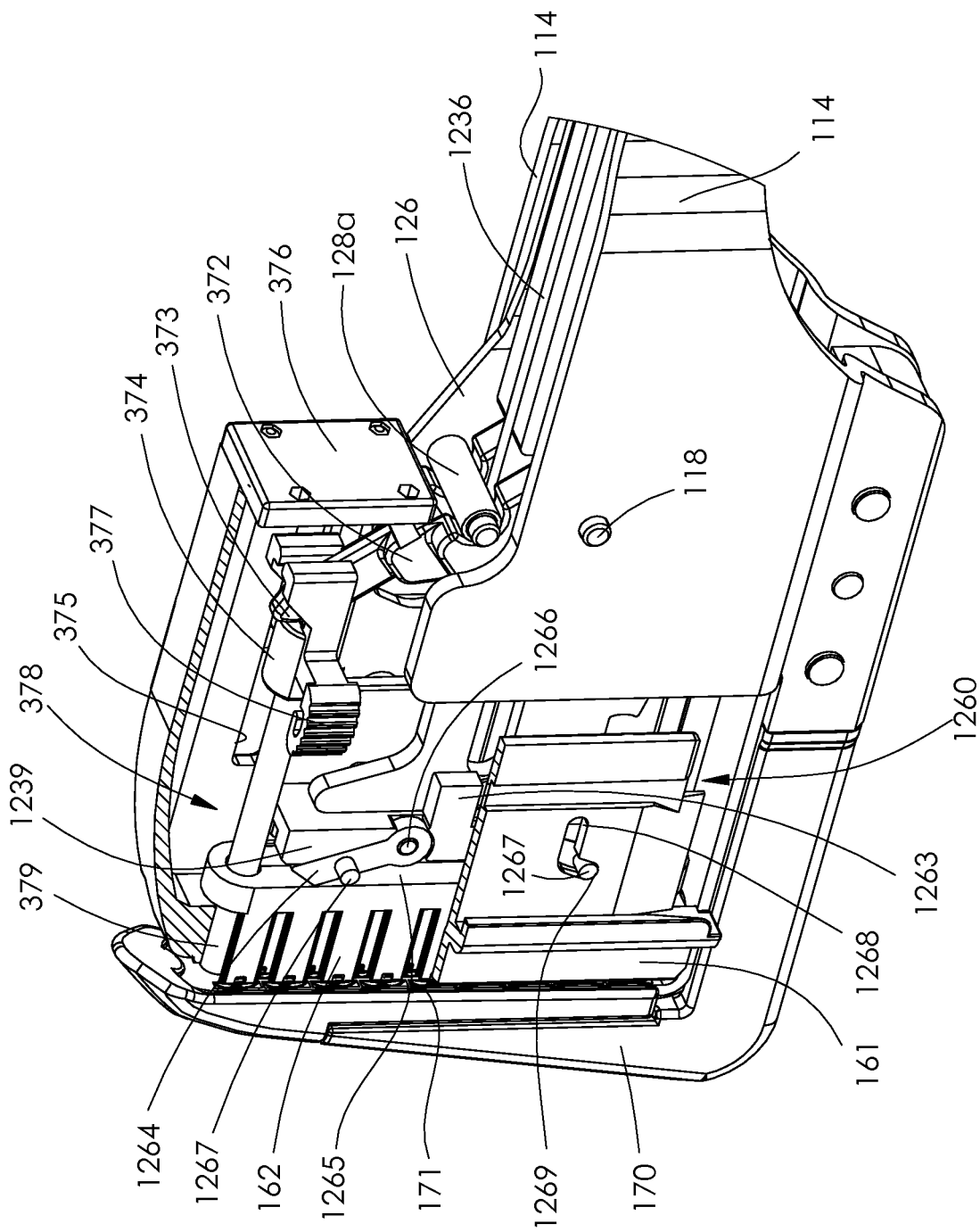
FIG. 53 is a partial cross-sectional view of the surgical stapling instrument of FIG. 50 illustrated in a tissue-cutting configuration.

Each of the drive arms 1264 is rotatably connected to the intermediate driver 1263 about a pivot pin 1266. Each drive arm 1264 is configured and arranged such that it can transmit a certain amount of force to the staple drivers 162 and, when the force transmitted through the drive arms 1264 exceeds a threshold force, the drive arms 1264 can rotate into a collapsed position, as illustrated in FIG. 53. The threshold force is selected such that it coincides with the force necessary to deform the staples into their formed, or fired, configurations; however, it is understood that a range of forces may be suitable to deform the staples to a suitable formed height and the threshold force can be anywhere in this suitable range or greater than this range. In any event, the collapse of the drive arms 1264 allows the intermediate driver 1263 to move relative to, or toward, the staple drivers 162 and, at such point, the staple drivers 162 may no longer move toward the anvil 170. Moreover, at such point, the staple firing process is complete and the relative motion now possible between the intermediate driver 1263 and the staple drivers 162 is utilized to deploy a cutting member, or knife, toward the anvil 170 to cut the tissue. The cutting stroke of the knife begins when the drive arms 1264 begin to collapse and ends when the drive arms 1264 contact a support surface 1239 defined on the intermediate driver 1263. As a result of the above, the tissue cutting operation is separate and distinct from the staple firing operation. Moreover, the staple firing operation and the tissue cutting operation occur sequentially and without overlap. Such an arrangement prevents the transection of the tissue prior to the staples being completely formed.

The reader should appreciate that the operator of the surgical instrument 1200 can retract the firing bar 1236 to its unfired position at any point during the staple firing operation of the instrument 1200. More specifically, the firing bar 1236 can be returned proximally until it comes into contact with the second drive pin 128b of the closure bar 126. The reader should also appreciate that the operator of the surgical instrument can open the end effector 1250 and move the staple cartridge 1260 away from the anvil 170 at any point during the staple firing operation of the instrument 1200. That said, the instrument 1200 includes a lockout system configured to prevent the end effector 1250 from being opened during the tissue cutting operation. Moreover, the knife member must be fully retracted by the firing bar 1236 before the tissue pin 379 can be retracted and/or the end effector 1250 can be opened. Such a lockout system is depicted in FIGS. 51-53.

Referring to FIG. 51, each drive arm 1264 of the staple firing system comprises a lock pin 1267 extending therefrom. Each lock pin 1267 is positioned in a lock slot defined in the cartridge body 161, wherein each lock slot comprises a first portion 1268 and a second portion 1269. As discussed in greater detail below, the lock pins 1267 are positioned in the first portions 1268 during the staple forming operation and the second portions 1269 during the tissue cutting operation. During the staple forming operation of the instrument 1200, the lock pins 1267 slide distally within the first portions 1268 of the lock slots, as illustrated in FIG. 52. In fact, the lock pins 1267 can be moved proximally and distally within the first portions 1268, thereby permitting the firing bar 1236 to be selectively advanced and retracted during the staple forming operation, as mentioned above. Moreover, such movement of the pins 1267 within the first portions 1268 permits the staple cartridge 1261 to be selectively moved proximally away from the anvil 170 of the instrument 1200, as also mentioned above, in order to open the end effector 1250. During the tissue cutting operation, however, the lock pins 1267 enter into the second portions 1269 of the lock slots. At such point, the sidewalls of the second portions 1269 prevent the cartridge body 161 from being retracted relative to the firing bar 1236. In this way, the staple cartridge 1260 is locked in place when the cutting member is exposed, or is possibly exposed. In such instances, the end effector 1250 cannot be opened until the cutting member is retracted, or at least sufficiently retracted. The cutting member is retracted when the firing bar 1236 is pulled proximally. As the firing member 1236 is pulled proximally, the lock pins 1267 move from the second portions 1269 of the lock slots into the first portions 1268 and unlock the cartridge body 161. At such point, the lock pin 379 can be retracted and/or end effector 1250 can be opened.

Figure 54:
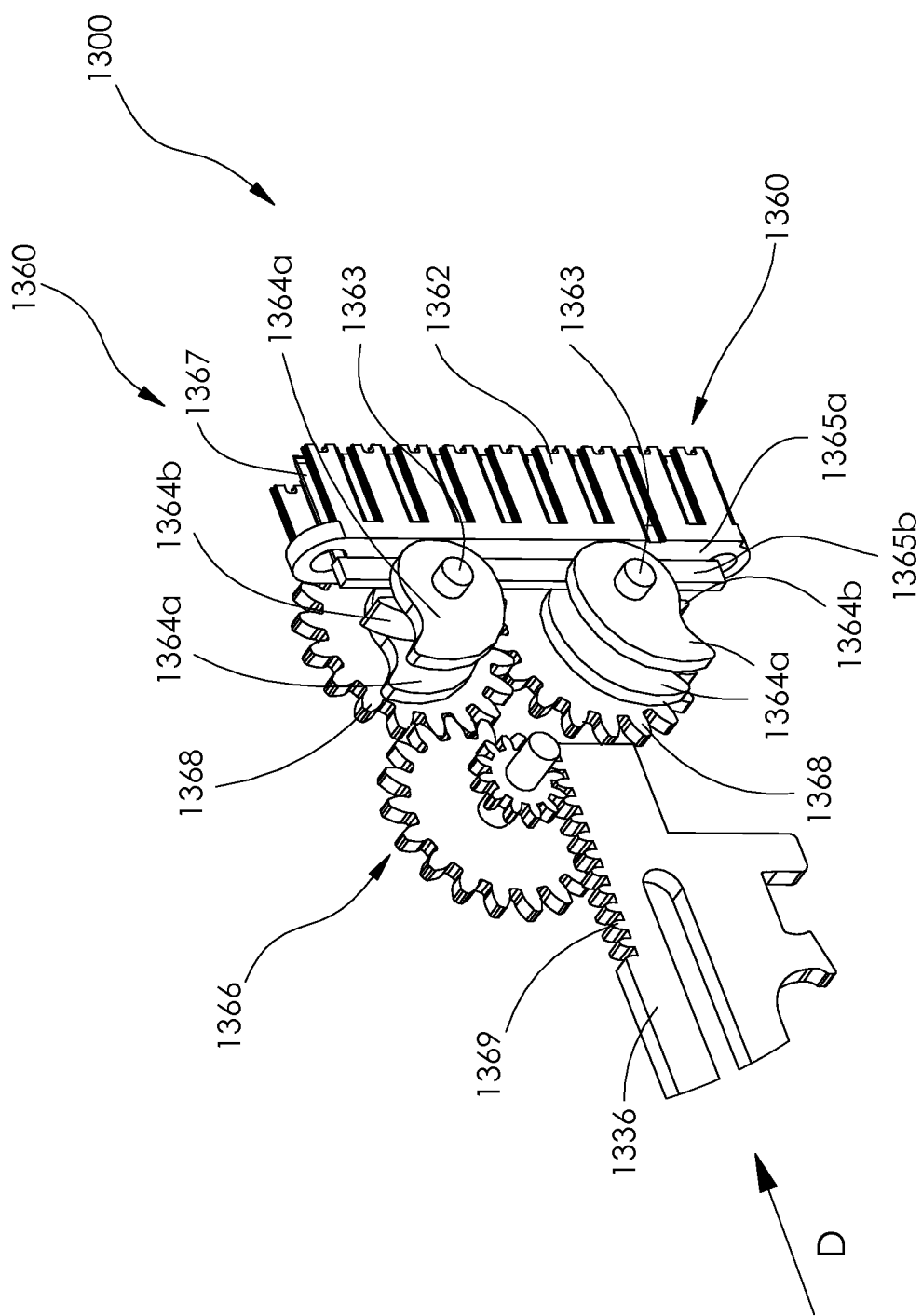
FIG. 54 is a partial perspective view of an end effector in accordance with at least one embodiment configured to sequentially fire staples and incise tissue captured within the end effector illustrated with components removed for the purpose of illustration.
Figure 55:
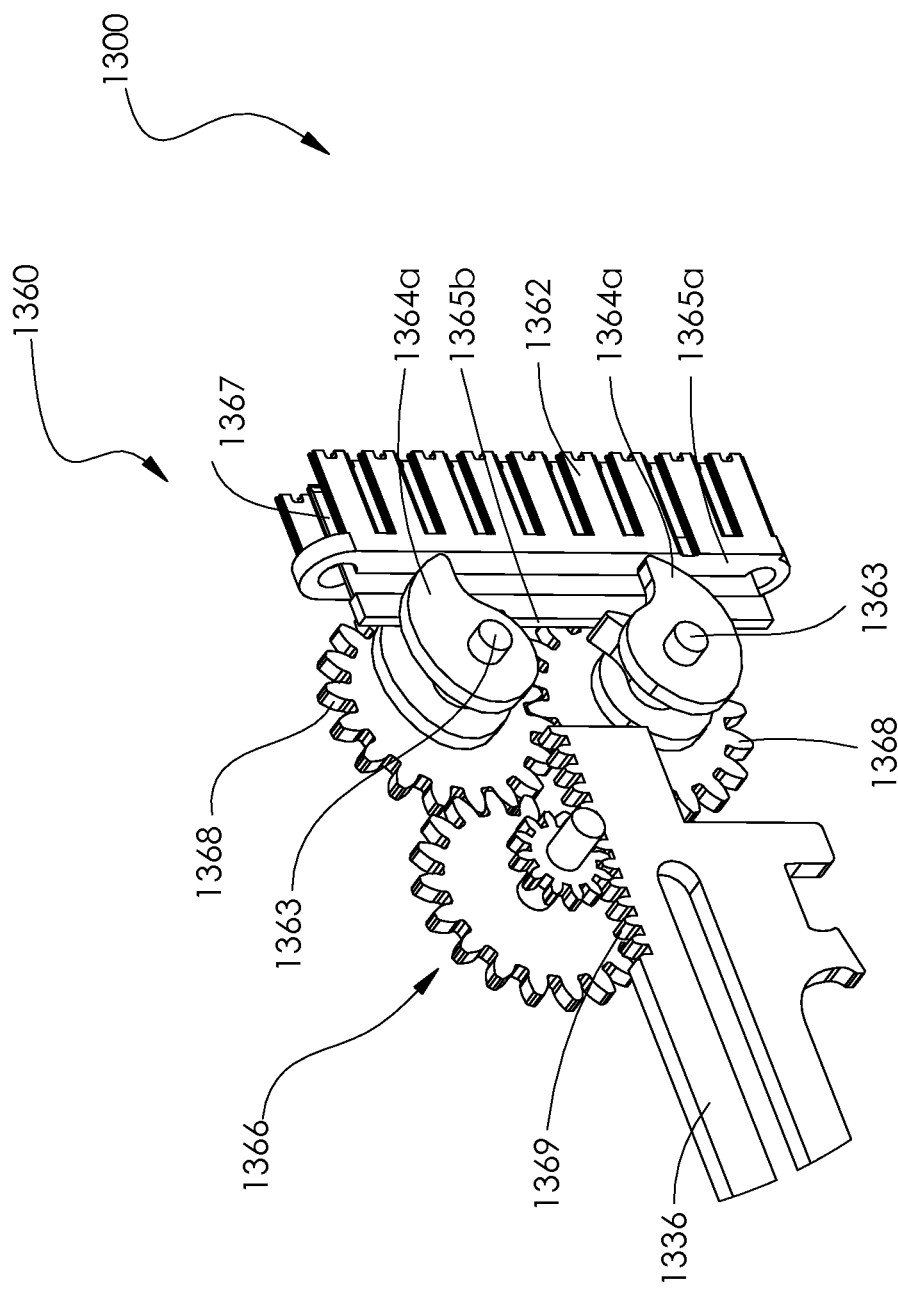
FIG. 55 is a partial perspective view of the end effector of FIG. 54 illustrated in a staple firing operating mode.
Figure 56:
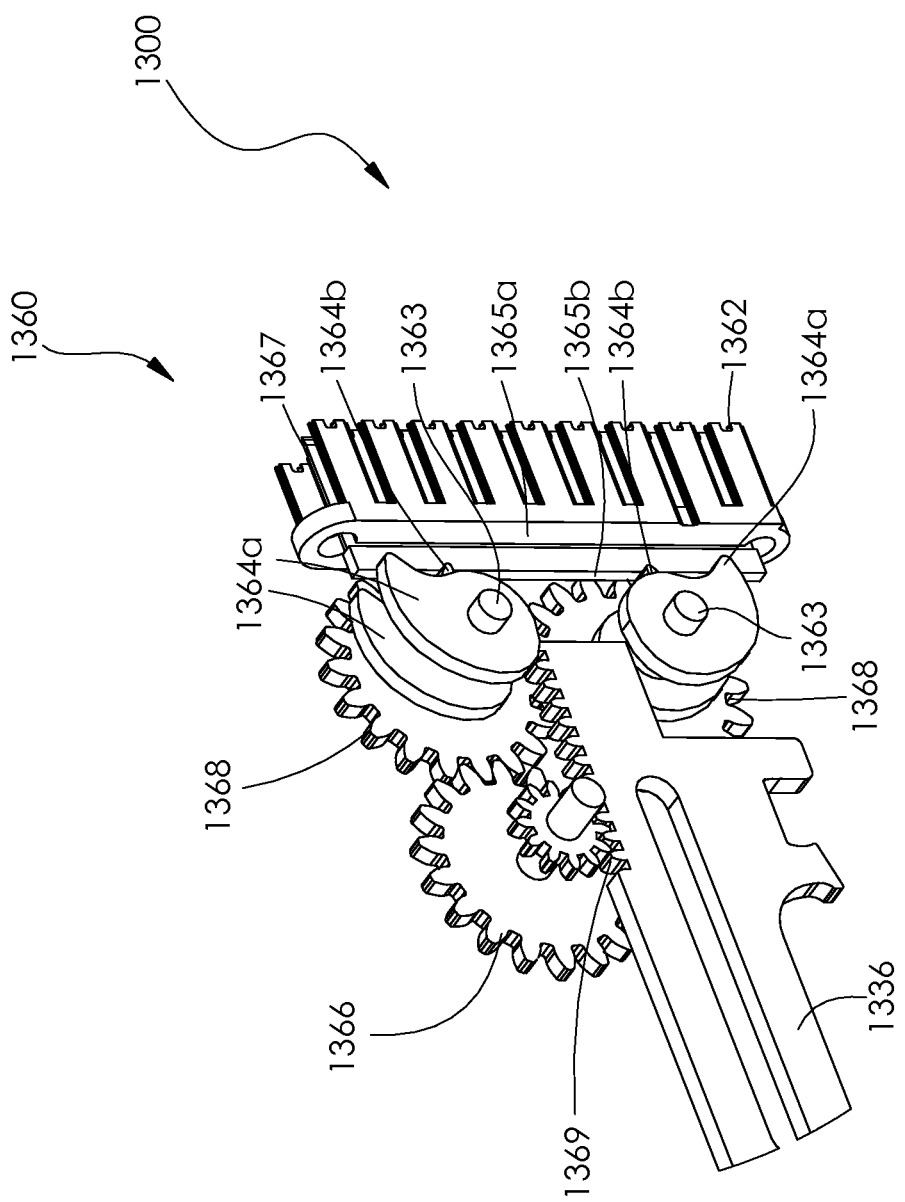
FIG. 56 is a partial perspective view of the end effector of FIG. 54 illustrated in a tissue transection operating mode.

An alternative embodiment of a tissue stapling and cutting mechanism of a surgical instrument 1300 is illustrated in FIGS. 54-56. The instrument 1300 comprises a staple cartridge jaw 1360 which comprises, one, a plurality of staple drivers 1362 configured to eject staples from the staple cartridge 1360 to staple tissue and, two, a knife member 1367 configured to incise the tissue. The staple drivers 1362 and the knife member 1367 are deployed by a firing member 1336; however, as discussed below, the deployment of the staple drivers 1362 and the knife member 1367 is staggered. The firing member 1336 comprises a rack of teeth 1369 which is moved, or translated, distally in direction D to deploy the staple drivers 1362 and the knife member 1367. The instrument 1300 further comprises a gear train 1366 operably engaged, or meshed, with the rack 1369 which includes a plurality of rotatable gears. The rack 1369 and the gear train 1366 are configured to convert the translational motion of the firing member 1336 to rotational motion of the gear train 1366.

The gear train 1366 includes first and second output gears 1368. Each output gear 1368 is mounted to a shaft 1363 such that the shaft 1363 and the gear 1368 rotate together. The gear train 1366 further comprises staple firing output cams 1364a, 1364b mounted to each of the shafts 1363. In the illustrated embodiment, each shaft 1363 comprises first and second staple deploying cams 1364a mounted thereto which rotate with the shaft 1383. Each cam 1364a comprises a contoured surface which is configured to engage a drive surface 1365a defined on the bottom of the staple drivers 1362. When the cams 1364a are rotated by the shafts 1363, the cam profiles are rotated between a first orientation associated with the unfired position of the staple drivers 1362 (FIG. 54) and a second orientation associated with the fired position of the staple drivers 1362 (FIG. 55). The first orientation and the second orientation are approximately 180 degrees apart, for example. Such movement of the cams 1364a and the staple drivers 1362 constitutes the firing stroke of the instrument 1300 and the peaks of the cams 1364a are in contact with the drive surface 1365a when the staple drivers 1362 have reached the end of the firing stroke, as illustrated in FIG. 55.

Further to the above, the instrument 1300 comprises four staple firing cams 1364a; however, any suitable number of cams 1364a could be utilized. The four staple firing cams 1364a are positioned and arranged relative to the drive surface 1365a to provide a balanced, or symmetrical, firing load to the staple drivers 1362. Upon comparing FIGS. 54 and 55, the reader should appreciate that the staple firing cams 1364a move the staple drivers 1362 relative to the knife member 1367. The knife member 1367 is deployed independently of the staple drivers 1362, as discussed below.

The gear train 1366 further comprises a tissue cutting output cam 1364b mounted to each of the shafts 1363. The cams 1364b are configured to deploy the knife member 1367. Similar to the above, the cams 1364b rotate between a first orientation (FIG. 54) and a second orientation (FIG. 55) during the staple firing process discussed above; however, the cams 1364b do not push the staple drivers 1362 or the knife member 1367 distally during this rotation. Referring now to FIG. 56, subsequent rotation of the shaft 1363 and the cams 1364b place the cams 1364b into engagement with a drive surface 1365b of the knife member 1367 which pushes the knife member 1367 distally to cut the stapled tissue. Such subsequent rotation also rotates the peaks of the staple firing cams 1364a out of engagement with the drive surface 1365a. In such instances, the staple drivers 1362 can float back into, or be permitted to retract back into, the staple cartridge 1360 as the tissue is being cut.

As discussed above, the cams 1364a and 1364b are positioned and arranged on the shafts 1363 such that the staple firing operation and the tissue cutting operation do not occur at the same time. In some instances, the cams 1364a and 1364b can be arranged such that there is a lull between the staple firing and tissue cutting operations. In at least one such instance, the cams 1364a and/or cams 1364b can include a dwell which create a pause between the staple firing operation and the tissue cutting operation. Such a pause can afford the surgeon an opportunity to stop the operation of the instrument 1300 between the staple firing stroke and the tissue cutting stroke. In alternative embodiments, the cams 1364a and 1365b can be positioned and arranged on the shafts 1363 such there is an overlap between the staple firing operation and the tissue cutting operation. Such an overlap permits a fast actuation of the instrument.

Figure 57:
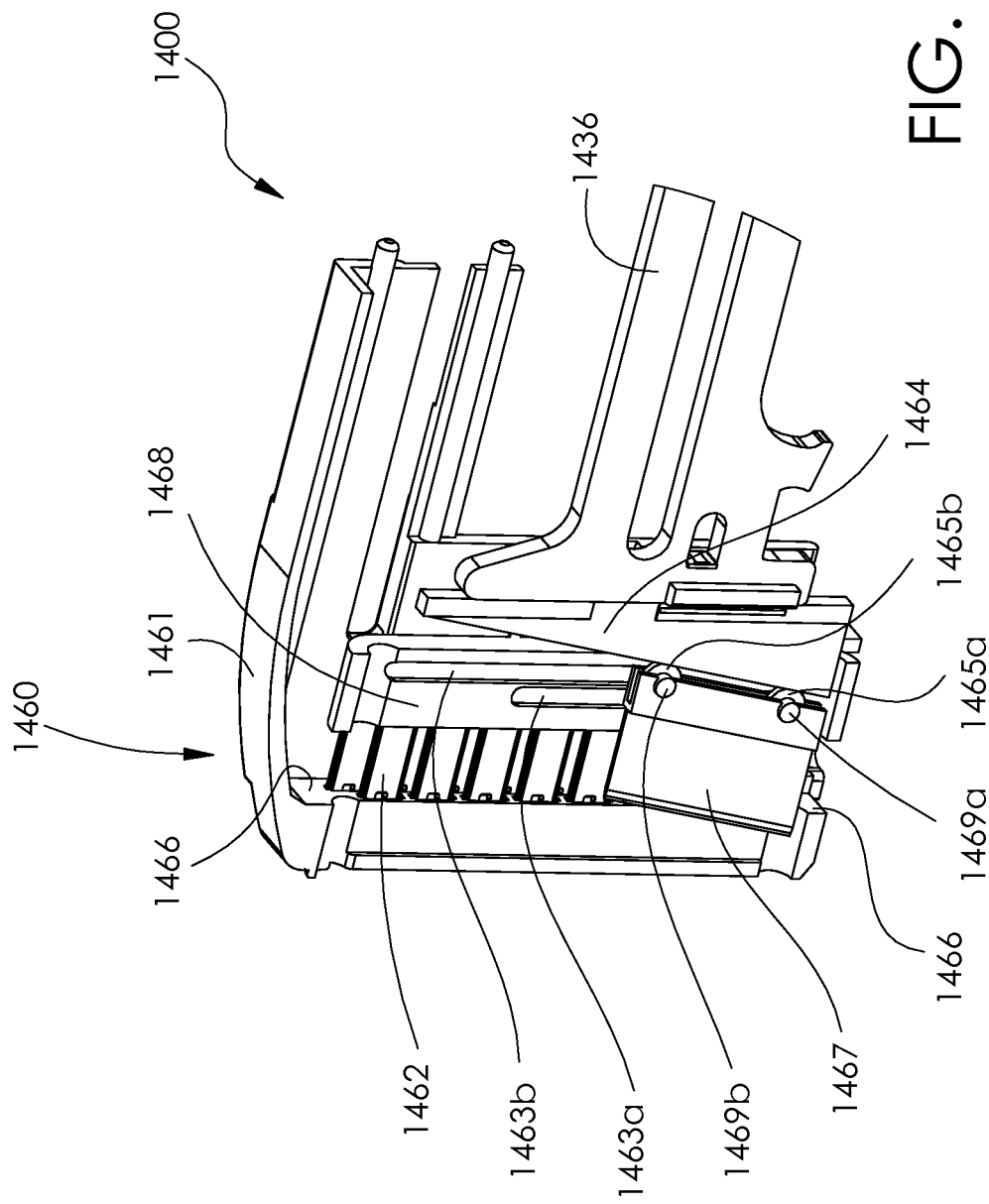
FIG. 57 is a partial cross-sectional perspective view of an end effector in accordance with at least one embodiment.
Figure 58:
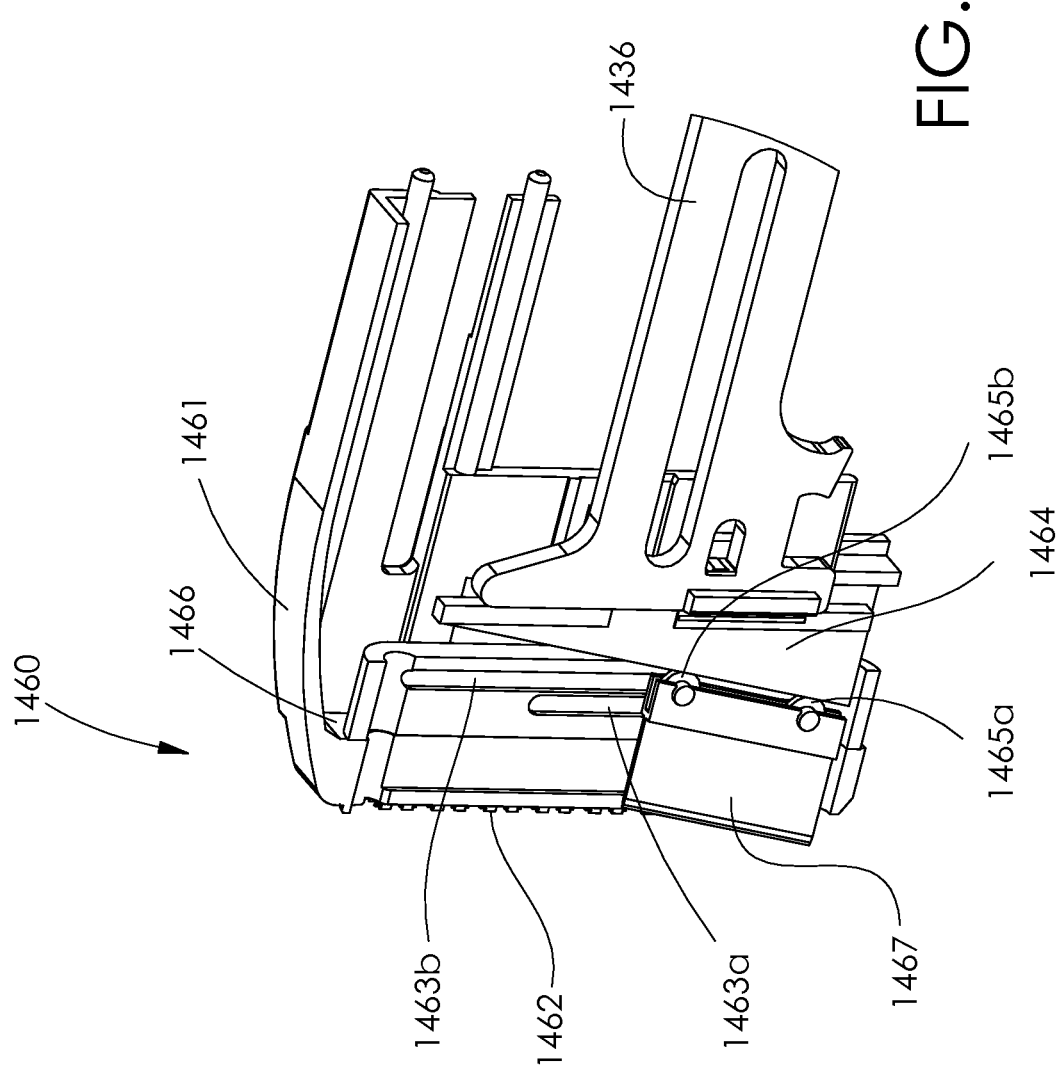
FIG. 58 is a partial cross-sectional perspective view of the end effector of FIG. 57 illustrated in a staple firing operating mode.
Figure 59:
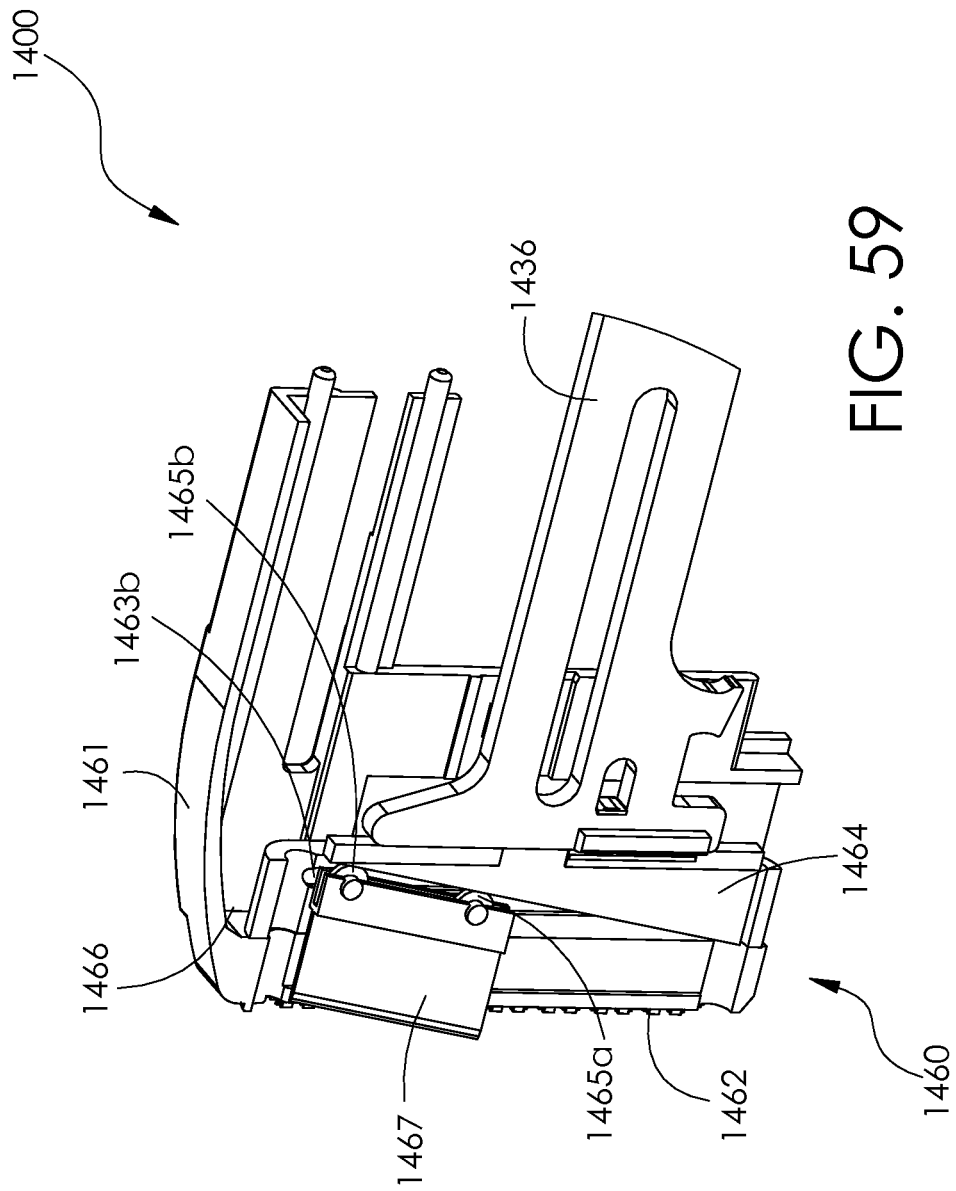
FIG. 59 is a partial perspective view of the end effector of FIG. 57 illustrated in a tissue transection operating mode.

An alternative embodiment of a tissue stapling and cutting mechanism of a surgical instrument 1400 is illustrated in FIGS. 57-59. The instrument 1400 comprises a staple cartridge jaw 1460 including a cartridge body 1461, a plurality of staple drivers 1462 configured to eject staples from the cartridge body 1461 to staple tissue and, a knife member 1467 configured to incise the tissue. The staple drivers 1462 and the knife member 1467 are deployed by a firing member 1436; however, as discussed below, the deployment of the staple drivers 1462 and the knife member 1467 is staggered. The staple drivers 1462 and the knife member 1467 move distally between a first, or unactuated, position (FIG. 57) and a second position (FIG. 58) which corresponds to the end of the staple firing process. The knife member 1467 is then movable relative to the staple drivers 1462 into a third position, as illustrated in FIG. 59.

Further to the above, the firing member 1436 comprises a ramped drive surface 1464 defined thereon. In use, the staple drivers 1462 and the knife member 1467 are pushed distally by the drive surface 1464 to fire the staples from the cartridge body 1461. More specifically, the drive surface 1464 pushes the knife member 1467 distally which, in turn, pushes the staple drivers 1462 distally, at least during the staple firing process. The knife member 1467 comprises rollers 1465a and 1465b which are in contact with the ramp surface 1464. The rollers 1465a and 1465b are rotatably mounted to the knife member 1467 about drive pins 1469a and 1469b, respectively. The drive pins 1469a and 1469b are positioned within drive slots 1463a and 1463b, respectively, defined in a frame 1468 which connects the staple drivers 1462. The drive pins 1469a, 1469b are configured to bear against the distal sidewalls of the drive slots 1463a, 1463b, respectively, when the knife member 1467 is pushed distally by the firing member 1436. In this way, a staple firing force is transmitted from the firing bar 1436 to the staple drivers 1462 via the drive ramp 1464, the rollers 1465a, 1465b, the drive pins 1469a, 1469b, and the drive slots 1463a, 1463b. The distal movement of the staple drivers 1462 is limited by a stop surface 1466 defined in the cartridge body 1461, for example. When the staple driver frame 1468 contacts the stop surface 1466, referring to FIG. 58, the firing stroke of the instrument 1400 is complete. At such point, only a portion of the cutting surface of the knife member 1467 has emerged from the cartridge body 1461; however, the tissue has not yet been exposed to the cutting surface. More particularly, the jaw, or anvil, opposing the staple cartridge 1460 can include a cavity which is configured to receive the emerged portion of the cutting surface and, as a result, the possibility of the knife member 1467 cutting the tissue at this point in the operation of the instrument 1400 is reduced.

As discussed above, the distal movement of the staple drivers 1462 and the knife member 1467 is constrained by the stop surface 1466 at the end of the firing stroke and, as a result, additional distal, or longitudinal, motion of the firing bar 1436 will no longer be translated into distal, or longitudinal, motion of the staple drivers 1462 and the knife member 1467. Instead, referring to FIG. 59, additional distal movement of the firing bar 1436 is converted into lateral movement of the knife member 1467. More specifically, additional distal movement of the ramp surface 1464 generates a reaction force between the knife member 1467 and the now static driver frame 1468 which displaces the knife member 1467 laterally along the descending ramp surface 1464. The lateral movement of the knife member 1467 is facilitated by the rollers 1465a, 1465b; however, the knife member 1467 could slide along the drive ramp 1464 in reaction to the continued distal movement of the firing member 1436 without the assistance of the rollers 1465a, 1465b.

Further to the above, the knife member 1467 cuts the stapled tissue as it moves laterally through the staple cartridge 1460. The knife member 1467 is displaced along a cutting axis which is transverse to a longitudinal firing axis defined by the motion of the firing member 1436. The cutting axis is orthogonal, or at least substantially orthogonal, to the firing axis; however, any suitable arrangement could be utilized. Also further to the above, the cutting stroke of the knife member 1467 begins at the end of firing stroke of the drivers 1462; however, it is envisioned that a delay could be provided between the cutting stroke and the firing stroke.

Many of the surgical instruments disclosed herein utilize a single firing bar for actuating a staple deploying system and a tissue cutting system. Such instruments can benefit from the use of auditory and/or tactile feedback which can communicate to the user of a surgical instrument certain information regarding the current operating state of the surgical instrument. In at least one example, a firing bar of a surgical instrument can include a first array of teeth and a second array of teeth which can slide relative to one or more clicking elements in the handle of the surgical instrument. During the staple firing operation of the surgical instrument, the interaction between the first array of teeth and a clicking element can generate clicking sounds and/or vibrations. The first array of teeth can be arranged on the firing bar such that the feedback is generated near the end of the firing stroke, for example. With such feedback, the surgeon can slow the progression of the firing bar if they intend to at least pause the operation of the surgical instrument between the staple firing operating mode and the tissue cutting operating mode, for example. Alternatively, the surgeon can elect to not cut the tissue. The second array of teeth can be arranged on the cutting bar such that the feedback is generated near the end of the cutting stroke, for example. In certain embodiments, an array of teeth can be arranged on the firing bar such that feedback is generated between the staple firing operating mode and the tissue cutting operating mode. The feedback described above could also be utilized with instruments including a staple firing bar and a separate tissue cutting bar.

A surgical instrument 1500 is disclosed in FIGS. 61-64. The instrument 1500 includes a shaft 1540 and a circular end effector 1550 which is utilized to staple and transect a lumen, for example. The end effector 1550 comprises a staple cartridge 1560 including a circular cartridge body 1561 and a plurality of staples removably stored in the cartridge body 1561 in a circular array. The staple cartridge 1560 further comprises staple drivers 1562 configured to eject the staples from the cartridge body 1561. The staple drivers 1562 are also arranged in a circular array and are connected to a common drive frame; however, any suitable arrangement could be utilized. For instance, the staple drivers 1562 may be unconnected to each other. The end effector 1550 further comprises a circular anvil 1570 configured to compress a portion of the lumen against the cartridge body 1561. The anvil 1570 is attached to a closure actuator 1526 which extends through the shaft 1540. The closure actuator 1526 is configured to move the anvil 1570 toward and away from the staple cartridge 1560 between clamped and unclamped positions. FIGS. 61-64 all illustrate the anvil 1570 in a clamped position. The anvil 1570 further comprises a circular array of forming pockets 1571 configured to deform the staples as the staples are ejected from the staple cartridge 1560.

Figure 63:
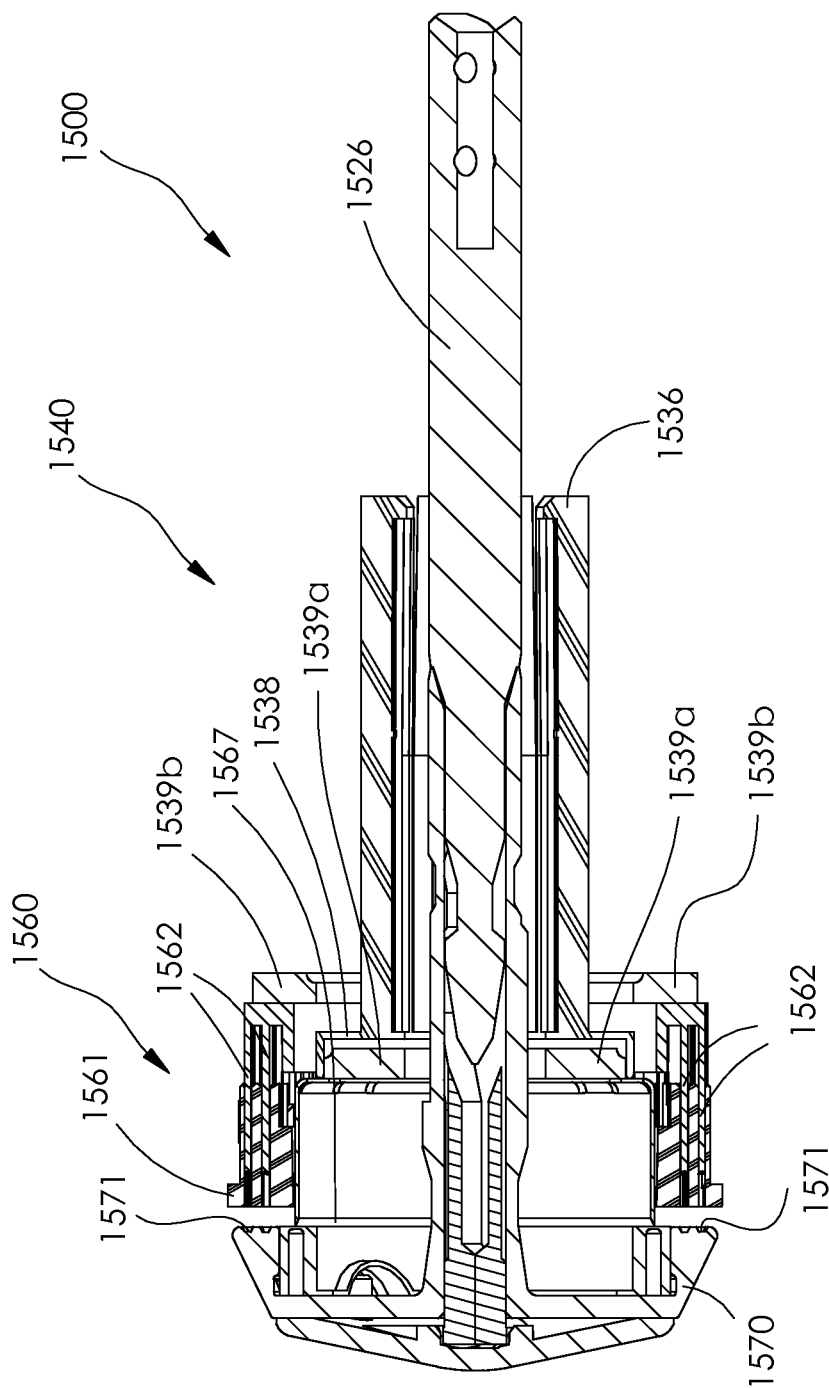
FIG. 63 is a partial cross-sectional view of the surgical stapling instrument of FIG. 60 in its tissue transecting operating mode.

The surgical instrument 1500 further comprises a cutting member 1567 configured to incise the tissue captured between the anvil 1570 and the staple cartridge 1560. In use, the staple drivers 1562 drive the staples against the anvil 1570 during a staple forming process (FIG. 61) and the cutting member 1567 cuts the tissue during a tissue cutting process (FIG. 63). As discussed below, the staple forming process and the tissue cutting process occur sequentially and there is no overlap therebetween; however, embodiments are contemplated in which the staple forming process and the tissue cutting process could occur, or at least partially occur, simultaneously.

Figure 60:
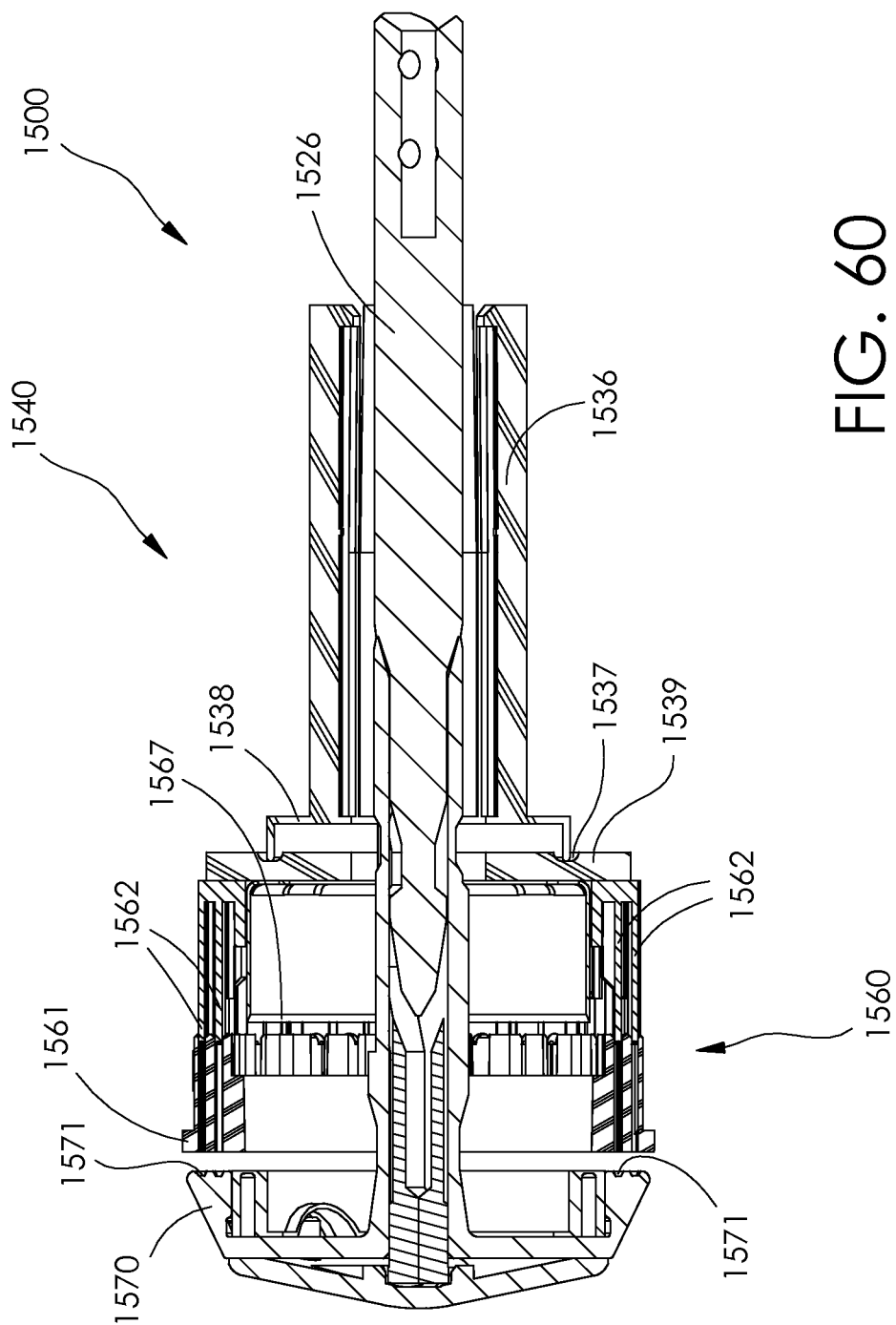
FIG. 60 is a partial cross-sectional view of a surgical stapling instrument in accordance with at least one embodiment.
Figure 61:
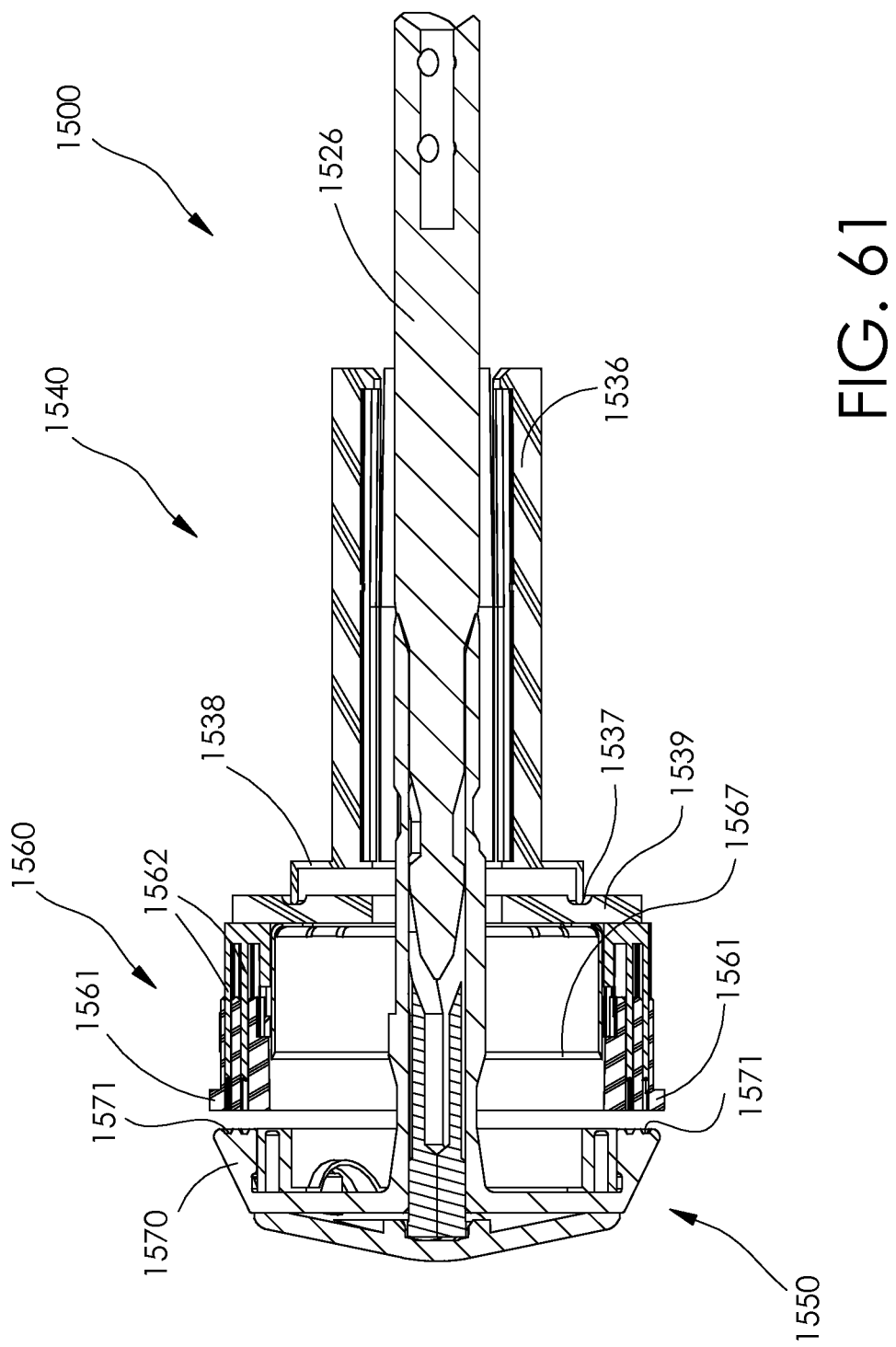
FIG. 61 is a partial cross-sectional view of the surgical stapling instrument of FIG. 60 illustrated in a staple firing operating mode.

Further to the above, and referring primarily to FIG. 60, the staple drivers 1562 and the cutting member 1567 are stored in an unactuated position in the end staple cartridge 1560 when the anvil 1570 is moved into its clamped position. The staple drivers 1562 and the cutting member 1567 are then moved distally by a firing member 1536 during the staple forming process to deform the staples, as illustrated in FIG. 61. More specifically, a distal end 1538 of the firing member 1536 engages a washer 1539 positioned intermediate the firing member 1536 and the drivers 1562 and the cutting member 1567 which, in turn, engages the drivers 1562 and the cutting member 1567. The firing stroke of the staple drivers 1562 ends when the drivers 1562 contact the proximal side of the cartridge body 1561. Notably, the cutting member 1567 does not emerge from the cartridge body 1561 during the staple forming process; rather, the cutting member 1567 remains positioned within the cartridge body 1561 during the staple forming process even though it is moved toward the anvil 1570.

Figure 62:
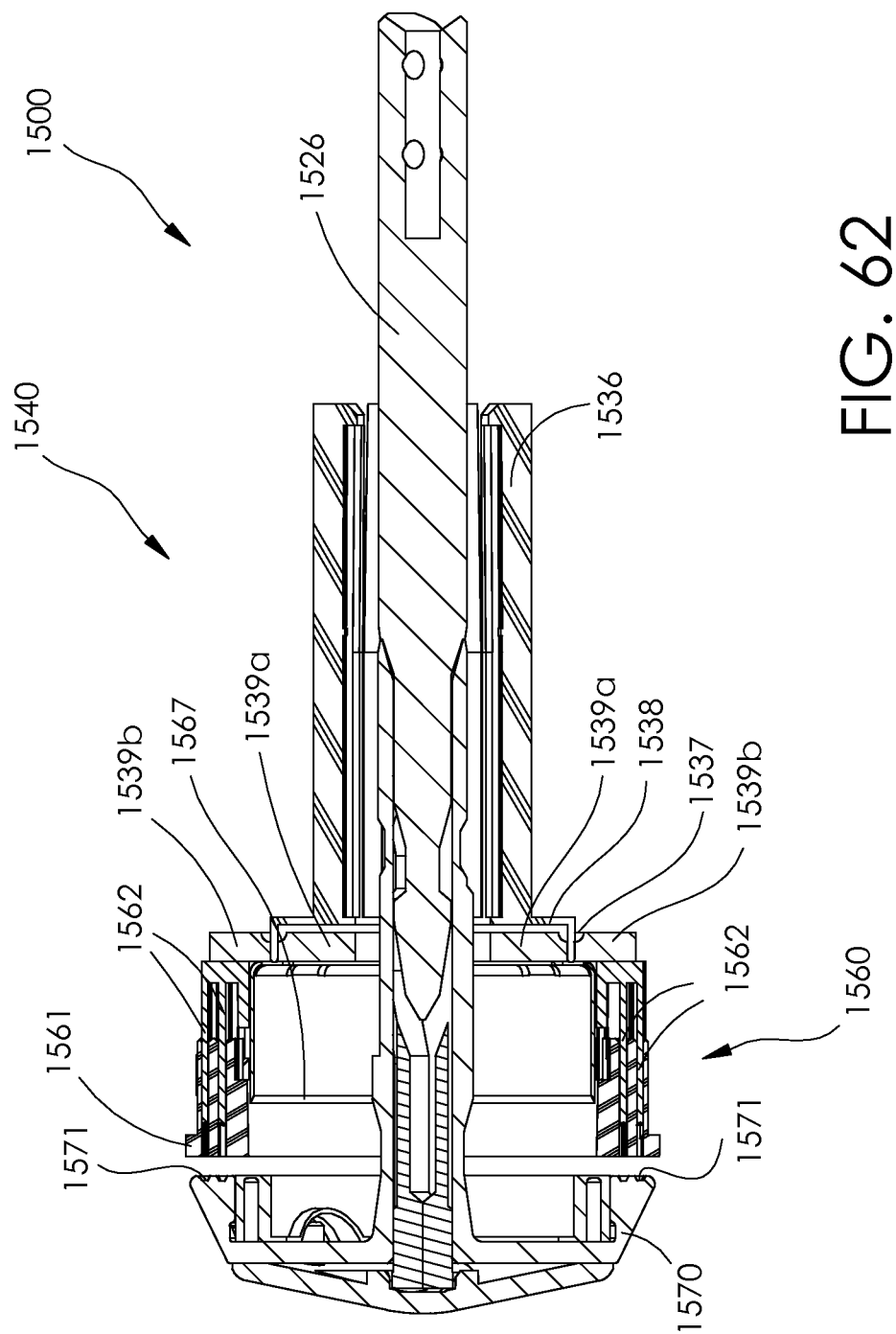
FIG. 62 is a partial cross-sectional view of the surgical stapling instrument of FIG. 60 transitioning between the staple firing operating mode and a tissue transecting operating mode.

Once the staple drivers 1562 have bottomed-out against the cartridge body 1561, the surgeon can understand that the staple forming process has been completed. At such point, the surgeon can then retract the firing member 1536 and skip the tissue cutting step, if they so choose. Alternatively, the surgeon can apply a pushing force to the firing member 1536 to break the washer 1539, as illustrated in FIG. 62. This pushing force is greater than the force needed to fire the staples. As a result, the surgeon will experience a noticeable increase in the force required to advance the firing member 1536 beyond the end of the staple firing stroke. To begin the tissue cutting stroke, the surgeon would have to volitionally elect to increase the force that they are applying to the firing member 1536 if the firing member 1536 is driven by a manually-operated actuator. The washer 1539 can be constructed such that it can withstand a force up to a threshold force, wherein once the threshold force has been met or exceeded, the distal end 1538 of the firing member 1536 can push through the washer 1539.

In certain instances, further to the above, the washer 1539 can be constructed such that it breaks-way, or fails suddenly, once the threshold force applied to the washer 1539 has been met. In at least one such instance, the washer 1539 can comprise a weakened portion which promotes the failure of the washer 1539 in a prescribed area, such as annular groove 1537, for example. In some instances, the distal end 1538 of the firing member 1536 can comprise a cutting portion which transects the washer 1539. In any event, the washer 1539 can act as a fuse which must fail before the cutting stroke can begin.

Once the washer 1539 is broken or transected, or has otherwise failed, referring to FIG. 63, the washer 1539 will comprise two separate portions—a first portion 1539a which can be pushed distally by the firing member 1536 and a second portion 1539b which remains behind. The groove 1537 is intermediate the first portion 1539a and the second portion 1539b of the washer 1539. The groove 1537 makes the washer 1539 sufficiently frangible such that the washer 1539 breaks once the appropriate level of force has been applied to the washer 1539. In at least one instance, the washer 1539 is comprised of plastic, for example. The first washer portion 1539a is pushed distally by the firing member 1536 to move the cutting member 1567 distally to complete the cutting stroke of the instrument 1500.

In addition to or in lieu of the manually-operated actuator, the instrument 1500 can include an electric motor configured to drive the firing member 1536. Such a system could also utilize at least one sensor configured to detect the loads experienced by the firing member and, in addition, a controller in communication with the load sensor and the electric motor which can govern the operation of the electric motor in view of data received from the load sensor. Such a system could recognize that the staple drivers 1562 had bottomed out and, in response thereto, pause the electric motor. Such a pause could allow the surgeon to choose whether or not to open the anvil 1570 after the staple firing process or instruct the controller to perform the tissue cutting process. The instrument 1500 can include a first button, for example, which can be actuated by the surgeon to open the anvil 1570 and a second button, for example, which can be actuated by the surgeon to perform the tissue cutting process.

Further to the above, each surgical instrument disclosed herein can include, or can be modified to include, one or more manually-operated triggers and/or one or more electric motors for operating the instrument. Surgical instruments 100, 200, 300, 400, 500, 600, 700, 800, 900, 1000, 1200, 1300, 1400, and 1500 can include a manually-operated closure system which transmits forces between a closure trigger and an end effector of the surgical instrument. For instance, the instrument 100 includes a manually-operated closure system configured to transmit the rotation of the closure trigger 120 to the end effector 150. In alternative embodiments, any of the instruments disclosed herein can include an electric motor configured to operate the closure system of the instrument. Similar to the above, the instruments can further include a control system configured to operate the electric motor in response to one or more inputs from the surgeon and/or data received from one or more sensors of the instrument.

In addition to or in lieu of the above, surgical instruments 100, 200, 300, 400, 500, 600, 700, 800, 900, 1000, 1200, 1300, 1400, and 1500 can include a manually-operated firing system which transmits forces between a firing trigger and an end effector of the surgical instrument. For instance, the instrument 100 includes a manually-operated firing system configured to transmit the rotation of the firing trigger 130 to the end effector 150. In alternative embodiments, any of the instruments disclosed herein can include an electric motor configured to operate the firing system of the instrument. Similar to the above, the instruments can further include a control system configured to operate the electric motor in response to one or more inputs from the surgeon and/or data received from one or more sensors of the instrument.

The reader should appreciate that the surgical instruments 100, 200, 300, 400, 500, 600, 700, 800, 900, 1000, 1200, 1300, and 1400 are often used during surgical techniques in which one or more large incisions are made in a patient to provide access to a surgical site within the patient. These surgical techniques are often referred to as "open" surgical techniques. The teachings provided herein are adaptable to surgical techniques in which instruments are inserted through one or more trocars, or cannulas, that provide access ports into the patient through smaller incisions, for example. Open surgical techniques often provide a surgeon with a better view of the surgical site while laparoscopic surgical techniques often result in smaller scars on the patient's body. The instrument 1500 is insertable through a natural orifice, such as the anus, for example, of a patient. The teachings provided herein are adaptable to surgical techniques in which instruments are inserted trough one or more natural orifices of the patient.

The reader should appreciate that the staples of the surgical instruments 100, 200, 300, 400, 500, 600, 700, 800, 900, 1000, 1200, 1300, 1400, and 1500 are deployed longitudinally, i.e., along, parallel to, or substantially parallel to, a longitudinal axis defined by the shaft of the surgical instrument. Other embodiments are envisioned in which the staples are deployed along one or more axes which are transverse to the longitudinal axis. FIGS. 64 and 65 disclose one such exemplary surgical instrument, i.e., surgical instrument 1600. The surgical instrument 1600 comprises a staple cartridge jaw 1660 and an anvil jaw 1670. The staple cartridge jaw 1660 and/or the anvil jaw 1670 is movable to clamp tissue therebetween. The staple cartridge jaw 1660 comprises a cartridge body 1661 including a plurality of staple cavities defined therein. The cartridge jaw 1660 further comprises a plurality of staples 1669 removably stored in the staple cavities and a plurality of staple drivers 1662 configured to eject the staples 1669 from the staple cavities. The instrument 1600 further comprises a firing bar 1636 which is movable distally to lift the staple drivers 1662 and staples 1669 toward the anvil jaw 1670. The anvil jaw 1670 includes staple forming pockets 1671 which are configured to deform the staples 1669, as illustrated in FIGS. 64 and 65. The teachings provided herein are adaptable to the surgical instrument 1600, or the like.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable, or movable, relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

EXAMPLES

Example 1—A surgical stapler for treating the tissue of a patient comprises a handle, a shaft extending from the handle, and an end effector extending from the shaft, wherein the end effector is configurable in an open configuration and a closed configuration. The end effector comprises a first jaw, a second jaw, wherein the second jaw is movable toward the first jaw to place the end effector in the closed configuration, a cartridge body including staple cavities, staples removably stored in the staple cavities, and an anvil configured to deform the staples. The surgical stapler further comprises a closure system configured to move the second jaw toward the first jaw, a firing system comprising a firing driver configured to eject the staples from the staple cavities toward the anvil during a firing stroke and a cutting member configured to cut the tissue during a cutting stroke and retract the cutting member during a retraction stroke, and means for preventing the end effector from being returned to the open configuration until after the retraction stroke has been completed.

Example 2—The surgical stapler of Example 1, wherein the means permits the end effector to be returned to the open configuration during the firing stroke.

Example 3—The surgical stapler of Examples 1 or 2, wherein the means permits the end effector to be returned to the open configuration after the firing stroke is completed and before the cutting stroke is initiated.

Example 4—The surgical stapler of Examples 1, 2, or 3, further comprising a tissue pin movable between an undeployed position and a deployed position, wherein the tissue pin is configured to trap the tissue within the end effector, and a tissue pin actuator configured to extend the tissue pin between the undeployed position and the deployed position during a deployment stroke and withdraw the tissue pin toward the undeployed position during a withdrawal stroke, wherein the means prevents the tissue pin from being withdrawn toward the undeployed position during the cutting stroke.

Example 5—The surgical stapler of Examples 1, 2, or 3, further comprising a tissue pin movable between an undeployed position and a deployed position, wherein the tissue pin is configured to trap the tissue within the end effector, and a tissue pin actuator configured to extend the tissue pin between the undeployed position and the deployed position during a deployment stroke and withdraw the tissue pin toward the undeployed position during a withdrawal stroke, wherein the means prevents the tissue pin from being withdrawn toward the undeployed position during the firing stroke.

Example 6—A surgical stapler for treating the tissue of a patient comprising a handle, a shaft extending from the handle, and an end effector extending from the shaft, wherein the end effector is configurable in an open configuration and a closed configuration. The end effector comprises a first jaw, a second jaw, wherein the second jaw is movable toward the first jaw to place the end effector in the closed configuration, a cartridge body including staple cavities, staples removably stored in the staple cavities, and an anvil configured to deform the staples. The surgical stapler further comprises a closure system configured to move the second jaw toward the first jaw, a firing system comprising a driver configured to eject the staples from the staple cavities toward the anvil during a firing stroke, and a cutting member configured to cut the tissue during a cutting stroke, wherein the cutting member comprises a cutting edge which is exposed from the cartridge body during the cutting stroke, and means for preventing the closure system from being returned to the open configuration while the cutting member is exposed.

Example 7—The surgical stapler of Example 6, wherein the means permits the end effector to be returned to the open configuration during the firing stroke.

Example 8—The surgical stapler of Examples 6 or 7, wherein the means permits the end effector to be returned to the open configuration after the firing stroke is completed and before the cutting stroke is initiated.

Example 9—The surgical stapler of Examples 6, 7, or 8, wherein the means permits the end effector to be returned to the open configuration after the firing stroke is completed and before the cutting member is exposed.

Example 10—The surgical stapler of Examples 6, 7, 8, or 9, further comprising a tissue pin movable between an undeployed position and a deployed position, wherein the tissue pin is configured to trap the tissue within the end effector, and a tissue pin actuator configured to extend the tissue pin between the undeployed position and the deployed position during a deployment stroke and withdraw the tissue pin toward the undeployed position during a withdrawal stroke, wherein the means prevents the tissue pin from being withdrawn toward the undeployed position while the cutting member is exposed.

Example 11—The surgical stapler of Examples 6, 7, 8, or 9, further comprising a tissue pin movable between an undeployed position and a deployed position, wherein the tissue pin is configured to trap the tissue within the end effector, and a tissue pin actuator configured to extend the tissue pin between the undeployed position and the deployed position during a deployment stroke and withdraw the tissue pin toward the undeployed position during a withdrawal stroke, wherein the means prevents the tissue pin from being withdrawn toward the undeployed position during the firing stroke.

Example 12—A surgical stapler for treating the tissue of a patient comprising a handle, a shaft extending from the handle, and an end effector extending from the shaft, wherein the end effector is configurable in an open configuration and a closed configuration. The end effector comprises a first jaw, a second jaw, wherein the second jaw is movable toward the first jaw to place the end effector in the closed configuration, a cartridge body including staple cavities, staples removably stored in the staple cavities, and an anvil configured to deform the staples. The surgical stapler further comprises a closure system configured to move the second jaw toward the first jaw, a firing system comprising a staple driver, wherein the firing system is configured to push the staple driver toward the anvil during a firing stroke and retract the staple driver during a retraction stroke, and a cutting member configured to cut the tissue during a cutting stroke, wherein the cutting member comprises a cutting edge which is exposed from the cartridge body during the cutting stroke, and means for preventing the staple driver from being retracted while the cutting member is exposed.

Example 13—The surgical stapler of Example 12, wherein the means permits the end effector to be returned to the open configuration during the firing stroke.

Example 14—The surgical stapler of Examples 12 or 13, wherein the means permits the end effector to be returned to the open configuration after the firing stroke is completed and before the cutting stroke is initiated.

Example 15—The surgical stapler of Examples 12, 13, or 14, wherein the means permits the end effector to be returned to the open configuration after the firing stroke is completed and before the cutting member is exposed.

Example 16—The surgical stapler of Examples 12, 13, 14, or 15 further comprising a tissue pin movable between an undeployed position and a deployed position, wherein the tissue pin is configured to trap the tissue within the end effector, and a tissue pin actuator configured to extend the tissue pin between the undeployed position and the deployed position during a deployment stroke and withdraw the tissue pin toward the undeployed position during a withdrawal stroke, wherein the means prevents the tissue pin from being withdrawn toward the undeployed position during the cutting stroke.

Example 17—The surgical stapler of Examples 12, 13, 14, or 15, further comprising a tissue pin movable between an undeployed position and a deployed position, wherein the tissue pin is configured to trap the tissue within the end effector, and a tissue pin actuator configured to extend the tissue pin between the undeployed position and the deployed position during a deployment stroke and withdraw the tissue pin toward the undeployed position during a withdrawal stroke, wherein the means prevents the tissue pin from being withdrawn toward the undeployed position during the firing stroke.

Example 18—A surgical stapler for treating the tissue of a patient comprising a handle, a shaft extending from the handle, an end effector extending from the shaft, wherein the end effector is configurable in an open configuration and a closed configuration. The end effector comprises a first jaw, a second jaw, wherein the second jaw is movable toward the first jaw to place the end effector in the closed configuration, a cartridge body including staple cavities, staples removably stored in the staple cavities, an anvil configured to deform the staples, and a tissue pin movable between an undeployed position and a deployed position, wherein the tissue pin is configured to trap the tissue within the end effector. The surgical stapler further comprises a closure system configured to move the second jaw toward the first jaw, a tissue pin actuator configured to move the tissue pin between the undeployed position and the deployed position during a deployment stroke and retract the tissue pin toward the undeployed position during a retraction stroke, a firing system comprising a staple driver, wherein the firing system is configured to push the staple driver toward the anvil during a firing stroke, and a cutting member configured to cut the tissue during a cutting stroke, wherein the cutting member comprises a cutting edge which is exposed from the cartridge body during the cutting stroke, and means for preventing the tissue pin from being retracted while the cutting member is exposed.

Example 19—The surgical stapler of Example 18, wherein the means permits the end effector to be returned to the open configuration during the firing stroke.

Example 20—The surgical stapler of Examples 18 or 19, wherein the means permits the end effector to be returned to the open configuration after the firing stroke is completed and before the cutting stroke is initiated.

Example 21—The surgical stapler of Examples 18, 19, or 20, wherein the means permits the end effector to be returned to the open configuration after the firing stroke is completed and before the cutting member is exposed.

Example 22—A surgical stapler for treating the tissue of a patient comprising a handle, a shaft extending from the handle, and an end effector extending from the shaft comprising a first jaw, a second jaw, wherein one of the first jaw and the second jaw is movable relative to the other of the first jaw, a cartridge body including staple cavities, staples removably stored in the staple cavities, and an anvil configured to deform the staples. The surgical stapler further comprises a firing system configured to eject the staples from the staple cavities toward the anvil during a firing stroke and cut the tissue during a cutting stroke after the firing stroke has been completed.

Example 23—The surgical stapler of Example 22, wherein the firing system comprises a firing bar, and wherein the firing bar is movable toward the end effector to perform the firing stroke and the cutting stroke.

Example 24—The surgical stapler of Examples 22 or 23, further comprising a stop configured to stop the firing bar after the firing stroke.

Example 25—The surgical stapler of Example 24, wherein the stop is manually-actuatable to release the firing member such that the firing member can perform the cutting stroke.

Example 26—The surgical stapler of Examples 22, 23, 24, or 25, wherein the firing system further comprises a staple driver configured to eject the staples from the staple cavities, and a cutting member configured to cut the tissue, wherein the cutting member moves with the staple driver during the firing stroke, and wherein the cutting member does not cut the tissue during the firing stroke.

Example 27—The surgical stapler of Example 26, wherein the cutting member is coupled to the staple driver during the firing stroke, and wherein the cutting member is uncoupled from the staple driver during the cutting stroke.

Example 28—The surgical stapler of Examples 26 or 27, further comprising a clamp which releasably holds the cutting member to the staple driver during the firing stroke of the firing member, wherein the clamp is configured to release the cutting member from the staple driver when a force transmitted through the firing member exceeds a threshold force.

Example 29—The surgical stapler of Examples 26 or 27, further comprising a clamp which releasably holds the staple driver to the cutting member during the firing stroke of the firing member, and a clamp restraint configured to releasably hold the clamp in a clamped state during the firing stroke and allow the clamp to bias open to disengage the firing member from the firing bar during the cutting stroke.

Example 30—The surgical stapler of Examples 22, 23, 24, 25, 26, 27, 28, or 29, wherein the handle comprises a firing trigger operably coupled with the firing member, wherein the firing trigger is rotatable through a first range of motion and a second range of motion, wherein the firing trigger moves the firing member through the firing stroke when the firing trigger is moved through the first range of motion, and wherein the trigger moves the firing member through the cutting stroke when the firing trigger is moved through the second range of motion.

Example 31—The surgical stapler of Example 30, wherein the first range of motion is discrete with respect to the second range of motion.

Example 32—The surgical stapler of Examples 30 or 31, wherein the first range of motion and the second range of motion occur during a single actuation of the firing trigger.

Example 33—The surgical stapler of Examples 22, 23, 24, 25, 26, 27, 28, 29, 30, 31, or 32, further comprising an indicator configured to provide a first indication when the firing stroke has been completed and a second indication when the cutting stroke has been completed, and wherein the first indication is different than the second indication.

Example 34—The surgical stapler of Example 33, wherein the first indication comprises one of a visual indication, an auditory indication, and a haptic indication, and wherein the second indication comprises one of a visual indication, an auditory indication, and a haptic indication.

Example 35—The surgical stapler of Example 30, wherein the first range of motion occurs during one actuation of the firing trigger, and wherein the second range of motion occurs during another actuation of the firing trigger.

Example 36—The surgical stapler of Example 30, further comprising an indicator configured to provide a first indication when the one actuation of the firing trigger has been completed and a second indication when the another actuation of the firing trigger has been completed, and wherein the first indication is different than the second indication.

Example 37—The surgical stapler of Examples 22, 23, 24, 25, 26, 27, 28, 29, 30, 31, 32, 33, 34, 35, or 36, wherein the firing system comprises a firing bar configured to eject the staples from the staple cavities during the firing stroke, and a knife bar configured to cut the tissue during the cutting stroke.

Example 38—The surgical stapler of Example 37, wherein the firing system further comprises a firing trigger, wherein the firing bar is driven toward the end effector during an actuation of the firing trigger, and wherein the knife bar is driven toward the end effector during the actuation of the firing trigger.

Example 39—The surgical stapler of Example 38, wherein the firing trigger is shiftable between a first position in which the firing trigger is operably engaged with the firing bar and a second position in which the firing trigger is operably engaged with the knife bar.

Example 40—The surgical stapler of Examples 38 or 39, further comprising a switching mechanism configured to automatically shift the firing trigger out of engagement with the firing bar and into engagement with the knife bar after the firing stroke.

Example 41—The surgical stapler of Examples 38, 39, or 40, further comprising a switching mechanism configured to permit the firing trigger to be manually shifted out of engagement with the firing bar and into engagement with the knife bar after the firing stroke.

Example 42—The surgical stapler of Example 37, wherein the firing system further comprises a firing trigger, wherein the firing bar is driven toward the end effector during a first actuation of the firing trigger, and wherein the knife bar is driven toward the end effector during a second actuation of the firing trigger.

Example 43—The surgical stapler of Example 37, wherein the firing system further comprises a firing trigger operably engaged with the firing bar, wherein an actuation of the firing trigger moves the firing bar through the firing stroke, and a cutting trigger operably engaged with the knife bar, wherein an actuation of the cutting trigger moves the knife bar through the cutting stroke.

Example 44—The surgical stapler of Examples 22, 23, 24, 25, 26, 27, 28, 29, 30, 31, 32, 33, 34, 35, 36, 37, 38, 39, 40, 41, 42, or 43, wherein the firing system is further configured to pause the operation of the surgical stapler after the firing stroke is completed so as to permit the user of the surgical stapler to optionally elect whether to perform the cutting stroke with the surgical stapler.

Example 45—A surgical stapler for treating the tissue of a patient comprising a handle, a shaft extending from the handle, and an end effector extending from the shaft comprising a first jaw, a second jaw, wherein one of the first jaw and the second jaw is movable relative to the other of the first jaw, a cartridge body including staple cavities, staples removably stored in the staple cavities, and an anvil configured to deform the staples. The surgical stapler further comprises a firing bar configured to eject the staples from the staple cavities during a firing stroke, a knife bar configured to cut the tissue during a cutting stroke, a firing trigger operably engaged with the firing bar, wherein an actuation of the firing trigger moves the firing bar through the firing stroke, and a cutting trigger operably engaged with the knife bar, wherein an actuation of the cutting trigger moves the knife bar through the cutting stroke.

Example 46—A surgical stapler for treating the tissue of a patient comprising a handle, a shaft extending from the handle, and an end effector extending from the shaft comprising a first jaw, a second jaw, wherein one of the first jaw and the second jaw is movable relative to the other of the first jaw, a cartridge body including staple cavities, staples removably stored in the staple cavities, and an anvil configured to deform the staples. The surgical stapler further comprises a firing system configured to eject the staples from the staple cavities toward the anvil during a firing stroke, a cutting system configured to cut the tissue during a cutting stroke, and means for preventing the cutting system from performing the cutting stroke until the firing system has completed the firing stroke.

Example 47—A surgical stapler for treating the tissue of a patient comprising a handle, a shaft extending from the handle, and an end effector extending from the shaft. The end effector comprises a first jaw, a second jaw, wherein one of the first jaw and the second jaw is movable relative to the other of the first jaw, a cartridge body including staple cavities, staples removably stored in the staple cavities, and an anvil configured to deform the staples. The surgical stapler further comprises a firing system configured to eject the staples from the staple cavities toward the anvil during a firing stroke and cut the tissue during a cutting stroke after the firing stroke has been completed, and means for permitting the user of the surgical instrument to elect whether to perform the cutting stroke with the surgical stapler after the firing stroke.

Example 48—The surgical stapler of Example 47, further comprising feedback means for indicating when the firing stroke has been completed.

Example 49—The surgical stapler of Examples 47 or 48, further comprising feedback means for indicating when the firing system is nearing the end of the firing stroke.

Example 50—The surgical stapler of Examples 47, 48, or 49, further comprising feedback means for indicating when the cutting stroke has been completed.

Example 51—The surgical stapler of Examples 47, 48, 49, or 50, further comprising feedback means for indicating when the firing system is nearing the end of the cutting stroke.

Example 52—The surgical stapler of Examples 47, 48, 49, 50, or 51, further comprising a visual indicator bar including a first range and a second range, wherein the first range demonstrates the progression of the firing stroke and the second range demonstrates the progression of the cutting stroke.

Example 53—The surgical stapler of Examples 47, 48, 49, 50, 51, or 52, wherein the means comprises a stop configured to stop the firing system after the firing stroke, and wherein the stop is selectively releasable by the user of the surgical stapler.

Example 54—A surgical stapler for treating the tissue of a patient comprising a handle, a shaft extending from the handle, and an end effector extending from the shaft comprising a first jaw, a second jaw, wherein one of the first jaw and the second jaw is movable relative to the other of the first jaw, a cartridge body including staple cavities, staples removably stored in the staple cavities, and an anvil configured to deform the staples. The surgical stapler further comprises a firing system configured to eject the staples from the staple cavities toward the anvil during a firing stroke, a cutting system configured to cut the tissue during a cutting stroke after the firing stroke has been completed, and means for pausing the surgical stapler to allow the user of the surgical stapler to elect whether or not to perform the cutting stroke with the surgical stapler.

Example 55—The surgical stapler of Example 54, further comprising feedback means for indicating when the firing stroke has been completed.

Example 56—The surgical stapler of Examples 54 or 55, further comprising feedback means for indicating when the firing system is nearing the end of the firing stroke.

Example 57—The surgical stapler of Examples 54, 55, or 56, further comprising feedback means for indicating when the cutting stroke has been completed.

Example 58—The surgical stapler of Examples 54, 55, 56, or 57, further comprising feedback means for indicating when the cutting system is nearing the end of the cutting stroke.

Example 59—The surgical stapler of Examples 54, 55, 56, 57, or 58, further comprising a visual indicator bar including a first range and a second range, wherein the first range demonstrates the progression of the firing stroke and the second range demonstrates the progression of the cutting stroke.

Example 60—The surgical stapler of Examples 54, 55, 56, 57, 58, or 59, wherein the firing system comprises a firing trigger, a firing bar operably engaged with the firing trigger, wherein an actuation of the firing trigger advances the firing member toward the end effector during the firing stroke, and a tactile feedback generator engaged with the firing bar.

Example 61—The surgical stapler of Example 60, wherein the tactile feedback generator is configured to generate a series of sounds which become increasingly louder as the firing stroke progresses.

Example 62—The surgical stapler of Examples 60 or 61, wherein the tactile feedback generator is silent during a first portion of the firing stroke and audible during a second portion of the firing stroke.

Example 63—The surgical stapler of Examples 60, 61, or 62, wherein the tactile feedback generator is configured to generate a series of sounds at a rate which increases as the firing stroke progresses.

Example 64—The surgical stapler of Examples 60, 61, 62, or 63, wherein the tactile feedback generator generates haptic feedback when the firing bar reaches the end of its firing stroke.

Example 65—The surgical stapler of Examples 54, 55, 56, 57, 58, 59, 60, 61, 62, 63, or 64, wherein the means comprises a stop configured to stop the firing system after the firing stroke, and wherein the stop is selectively releasable by the user of the surgical stapler.

Example 66—A surgical stapler for treating the tissue of a patient comprising a handle, a shaft extending from the handle, and an end effector extending from the shaft comprising a first jaw, a second jaw, wherein one of the first jaw and the second jaw is movable relative to the other of the first jaw, a cartridge body including staple cavities, staples removably stored in the staple cavities, and an anvil configured to deform the staples. The surgical stapler further comprises a firing system configured to eject the staples from the staple cavities toward the anvil during a firing stroke, a cutting system configured to cut the tissue during a cutting stroke after the firing stroke has been completed, and a feedback generator configured to indicate a shift between the firing stroke and the cutting stroke.

Example 67—A surgical stapler for treating the tissue of a patient comprising a handle, a shaft extending from the handle, and an end effector extending from the shaft, wherein the end effector is configurable in an open configuration and a closed configuration. The end effector comprises a first jaw, a second jaw, wherein the second jaw is movable toward the first jaw to place the end effector in the closed configuration, a cartridge body including staple cavities, staples removably stored in the staple cavities, and an anvil configured to deform the staples. The surgical stapler further comprises a closure system configured to move the second jaw toward the first jaw, and a firing system comprising a staple driver, wherein the firing system is configured to push the staple driver toward the anvil during a firing stroke and retract the staple driver during a retraction stroke, and a cutting member configured to cut the tissue during a cutting stroke, wherein the cutting member comprises a cutting edge which is exposed from the cartridge body during the cutting stroke. The surgical stapler further comprises a lockout configured to prevent the staple driver from being retracted during the firing stroke and a bypass configured to overcome the lockout such that the staple driver can be retracted during the firing stroke.

Example 68—A surgical stapler for treating the tissue of a patient comprising a handle, a shaft extending from the handle, and an end effector extending from the shaft, wherein the end effector is configurable in an open configuration and a closed configuration. The end effector comprises a first jaw, a second jaw, wherein the second jaw is movable toward the first jaw to place the end effector in the closed configuration, a cartridge body including staple cavities, staples removably stored in the staple cavities, and an anvil configured to deform the staples. The surgical stapler further comprises a closure system configured to move the second jaw toward the first jaw, and a firing system comprising a staple driver, wherein the firing system is configured to push the staple driver toward the anvil during a firing stroke and retract the staple driver during a retraction stroke, and a cutting member configured to cut the tissue during a cutting stroke, wherein the cutting member comprises a cutting edge which is exposed from the cartridge body during the cutting stroke. The surgical stapler further comprises a lock configured to prevent the staple driver from being retracted prior to the completion of the cutting stroke and a bypass configured to overcome the lock such that the staple driver can be retracted prior to the completion of the cutting stroke.

Example 69—A surgical stapler for treating the tissue of a patient comprising a handle, a shaft extending from the handle, and an end effector extending from the shaft, wherein the end effector is configurable in an open configuration and a closed configuration. The end effector comprises a first jaw, a second jaw, wherein the second jaw is movable toward the first jaw to place the end effector in the closed configuration, a cartridge body including staple cavities, staples removably stored in the staple cavities, and an anvil configured to deform the staples. The surgical stapler further comprises a closure system configured to move the second jaw toward the first jaw and a firing system comprising a staple driver, wherein the firing system is configured to push the staple driver toward the anvil during a firing stroke and retract the staple driver during a retraction stroke, and a cutting member configured to cut the tissue during a cutting stroke, wherein the cutting member comprises a cutting edge which is exposed from the cartridge body during the cutting stroke. The surgical stapler further comprises a lockout configured to prevent the cutting member from being retracted during the cutting stroke and a bypass configured to overcome the lockout such that the cutting member can be retracted during the cutting stroke.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Patent Application Publication No. 2013/0334278;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical stapler for treating the tissue of a patient, comprising:
   a handle;
   a shaft extending from said handle;
   an end effector extending from said shaft, comprising:
     a first jaw;
     a second jaw, wherein one of said first jaw and said second jaw is movable relative to the other of said first jaw and said second jaw;
     a cartridge body including staple cavities;
     staples removably stored in said staple cavities; and
     an anvil configured to deform said staples;
   a firing system comprising a firing bar, wherein said firing system is configured to:
     eject said staples from said staple cavities toward said anvil during a firing stroke; and
     cut the tissue during a cutting stroke after said firing stroke has been completed, wherein said firing bar is movable toward said end effector to perform said firing stroke and said cutting stroke; and
   a switch configured to stop said firing bar after said firing stroke, wherein said switch is operable independently of said firing system, wherein said switch is movable between a first position and a second position, and wherein said switch is manually-actuatable to release said firing bar such that said firing bar can perform said cutting stroke.

2. The surgical stapler of claim 1, wherein said firing system further comprises:
   a staple driver configured to eject said staples from said staple cavities; and
   a cutting member configured to cut the tissue, wherein said cutting member moves with said staple driver during said firing stroke, and wherein said cutting member does not cut the tissue during said firing stroke.

3. The surgical stapler of claim 2, wherein said cutting member is coupled to said staple driver during said firing stroke, and wherein said cutting member is uncoupled from said staple driver during said cutting stroke.

4. The surgical stapler of claim 3, further comprising a clamp which releasably holds said cutting member to said staple driver during said firing stroke of said firing bar, wherein said clamp is configured to release said cutting member from said staple driver when a force transmitted through said firing bar exceeds a threshold force.

5. A surgical stapler for treating the tissue of a patient, comprising:
   a handle;
   a shaft extending from said handle;
   an end effector extending from said shaft, comprising:
     a first jaw;
     a second jaw, wherein one of said first jaw and said second jaw is movable relative to the other of said first jaw and said second jaw;
     a cartridge body including staple cavities;
     staples removably stored in said staple cavities; and
     an anvil configured to deform said staples; and
   a firing system comprising a firing bar, wherein said firing system is configured to:
     eject said staples from said staple cavities toward said anvil during a firing stroke; and
     cut the tissue during a cutting stroke after said firing stroke has been completed, wherein said firing bar is movable toward said end effector to perform said firing stroke and said cutting stroke, wherein said firing system further comprises:
       a staple driver configured to eject said staples from said staple cavities; and
       a cutting member configured to cut the tissue, wherein said cutting member moves with said staple driver during said firing stroke, wherein said cutting member does not cut the tissue during said firing stroke, wherein said cutting member is coupled to said staple driver during said firing stroke, and wherein said cutting member is uncoupled from said staple driver during said cutting stroke, wherein said surgical stapler further comprises:

a clamp which releasably holds said staple driver to said cutting member during said firing stroke of said firing bar; and a clamp restraint configured to releasably hold said clamp in a clamped state during said firing stroke and allow said clamp to bias open to disengage said staple driver from said cutting member during said cutting stroke.

6. The surgical stapler of claim 1, wherein said handle comprises a firing trigger operably coupled with said firing bar, wherein said firing trigger is rotatable through a first range of motion and a second range of motion, wherein said firing trigger moves said firing bar through said firing stroke when said firing trigger is moved through said first range of motion, and wherein said firing trigger moves said firing bar through said cutting stroke when said firing trigger is moved through said second range of motion.

7. The surgical stapler of claim 6, wherein said first range of motion is discrete with respect to said second range of motion.

8. The surgical stapler of claim 7, wherein said first range of motion and said second range of motion occur during a single actuation of said firing trigger.

9. The surgical stapler of claim 6, further comprising an indicator configured to provide a first indication when said firing stroke has been completed and a second indication when said cutting stroke has been completed, and wherein said first indication is different than said second indication.

10. The surgical stapler of claim 9, wherein said first indication comprises one of a visual indication, an auditory indication, and a haptic indication, and wherein said second indication comprises one of a visual indication, an auditory indication, and a haptic indication.

11. The surgical stapler of claim 6, wherein said first range of motion occurs during one actuation of said firing trigger, and wherein said second range of motion occurs during another actuation of said firing trigger.

12. The surgical stapler of claim 11, further comprising an indicator configured to provide a first indication when said one actuation of said firing trigger has been completed and a second indication when said another actuation of said firing trigger has been completed, and wherein said first indication is different than said second indication.

13. The surgical stapler of claim 1, wherein said firing system comprises:
a firing bar configured to eject said staples from said staple cavities during said firing stroke; and
a knife bar configured to cut the tissue during said cutting stroke.

14. The surgical stapler of claim 13, wherein said firing system further comprises a firing trigger, wherein said firing bar is driven toward said end effector during an actuation of said firing trigger, and wherein said knife bar is driven toward said end effector during said actuation of said firing trigger.

15. The surgical stapler of claim 14, wherein said firing trigger is shiftable between a first position in which said firing trigger is operably engaged with said firing bar and a second position in which said firing trigger is operably engaged with said knife bar.

16. The surgical stapler of claim 14, further comprising a switching mechanism configured to automatically shift said firing trigger out of engagement with said firing bar and into engagement with said knife bar after said firing stroke.

17. The surgical stapler of claim 14, further comprising a switching mechanism configured to permit said firing trigger to be manually shifted out of engagement with said firing bar and into engagement with said knife bar after said firing stroke.

18. The surgical stapler of claim 13, wherein said firing system further comprises a firing trigger, wherein said firing bar is driven toward said end effector during a first actuation of said firing trigger, and wherein said knife bar is driven toward said end effector during a second actuation of said firing trigger.

19. The surgical stapler of claim 13, wherein said firing system further comprises:
a firing trigger operably engaged with said firing bar, wherein an actuation of said firing trigger moves said firing bar through said firing stroke; and
a cutting trigger operably engaged with said knife bar, wherein an actuation of said cutting trigger moves said knife bar through said cutting stroke.

20. The surgical stapler of claim 1, wherein said firing system is further configured to pause the operation of said surgical stapler after said firing stroke is completed so as to permit the user of said surgical stapler to optionally elect whether to perform said cutting stroke with said surgical stapler.

21. A surgical stapler for treating the tissue of a patient, comprising:
a handle;
a shaft extending from said handle;
an end effector extending from said shaft, comprising:
a first jaw;
a second jaw, wherein one of said first jaw and said second jaw is movable relative to the other of said first jaw and said second jaw;
a cartridge body including staple cavities;
staples removably stored in said staple cavities; and
an anvil configured to deform said staples;
a firing system configured to eject said staples from said staple cavities toward said anvil during a firing stroke;
a cutting system configured to cut the tissue during a cutting stroke; and
means for preventing said cutting system from performing said cutting stroke until said firing system has completed said firing stroke, wherein said cutting system cannot be actuated prior to the completion of said firing stroke by said firing system.

* * * * *